US011634725B2

(12) United States Patent
Wang

(10) Patent No.: US 11,634,725 B2
(45) Date of Patent: Apr. 25, 2023

(54) METHODS AND COMPOSITIONS FOR PLANT PATHOGEN RESISTANCE IN PLANTS

(71) Applicant: UNIVERSITY OF FLORIDA RESEARCH FOUNDATION, INC., Gainesville, FL (US)

(72) Inventor: Nian Wang, Auburndale, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 3 days.

(21) Appl. No.: 16/761,409

(22) PCT Filed: Nov. 5, 2018

(86) PCT No.: PCT/US2018/059269
§ 371 (c)(1),
(2) Date: May 4, 2020

(87) PCT Pub. No.: WO2019/090261
PCT Pub. Date: May 9, 2019

(65) Prior Publication Data

US 2021/0155952 A1 May 27, 2021

Related U.S. Application Data

(60) Provisional application No. 62/627,496, filed on Feb. 7, 2018, provisional application No. 62/581,491, filed on Nov. 3, 2017.

(51) Int. Cl.
*C12N 15/82* (2006.01)

(52) U.S. Cl.
CPC .............................. *C12N 15/8281* (2013.01)

(58) Field of Classification Search
CPC .............................................. C12N 15/8281
See application file for complete search history.

(56) References Cited

U.S. PATENT DOCUMENTS

2011/0119788 A1 5/2011 Rodriguez Baixauli et al.

FOREIGN PATENT DOCUMENTS

WO 2019090261 A1 5/2019

OTHER PUBLICATIONS

Wang et al (The Candidatus Liberibacter-Host Interface: Insights into Pathogenesis Mechanisms and Disease Control. Annu. Rev. Phytopathol. 55:451-82, Jun. 2017). (Year: 2017).*
Friedberg (Automated protein function prediction—the genomic challenge. Brief. Bioinformatics. 7:225-242, 2006) (Year: 2006).*
Wang et al (From Protein Sequence to Protein Function via Multi-Label Linear Discriminant Analysis. IEEE/ACM Transactions on Computational Biology and Bioinformatics, vol. 14, No. 3, 503-513, 2017) (Year: 2017).*
Pang et al (Citrus CsACD2 Is a Target of Candidatus Liberibacter Asiaticus in Huanglongbing Disease. Plant Physiology, vol. 184, pp. 792-805, 2020) (Year: 2020).*
Akpata et al (Chemical composition and selected functional properties of sweet orange (*Citrus sinensis*) seed flour. Plant Foods for Human Nutrition 54: 353-362, 1999). (Year: 1999).*
Wang et al (The Candidates Liberibacter-Host Interface: Insights into Pathogenesis Mechanisms and Disease Control. Annu. Rev. Phytopathol.55:451-482, 2017). (Year: 2017).*
Fu et al (Transcriptome analysis of sweet orange trees infected with 'Candidates Liberibacter asiatices' and two strains of Citrus Tristeza Virus. BMC Genomics 17:349, 1-18, 2016). (Year: 2016).*
Mach et al (The *Arabidopsis*-accelerated cell death gene ACD2 encodes red chlorophyll catabolite reductase and suppresses the spread of disease symptoms. PNAS vol. 98:771-776, 2001) (Year: 2001).*
Zhang et al (A Sec-Dependent Secretory Protein of the Huanglongbing-Associated Pathogen Suppresses Hypersensitive Cell Death in Nicotiana benthamiana. Frontiers in Microbiology. 1-11, 2020) (Year: 2020).*
PCT/US20108/05269 Search Report and Written Opinion, dated Mar. 11, 2019, 17 pages.
Clark, Kelley et al., "An effector from the Huanglongbing-associated pathogen targets citrus proteases", Nature Communications, 2018, vol. 9, pp. 1718.
Fu, Shimin et al., "Transcriptome analysis of sweet orange trees infected with 'Candidatus Liberibacter asiaticus' and two strains of Citrus Tristeza Virus", BMC Genomics, 2016, vol. 17, No. 349, 18 pages.
Ma, W, "Effectoromics of the Huanglongbing (HLB)-associated pathogen", University of California, Riverside,2016, 7 pages.

(Continued)

*Primary Examiner* — Charles Logsdon
*Assistant Examiner* — Wayne Zhong
(74) *Attorney, Agent, or Firm* — Timothy H. Van Dyke; Wolter, Van Dyke, Davis, PLLC

(57) ABSTRACT

The disclosure relates to a plant that is tolerant or resistant to species of *Ca. Liberibacter*. Specifically exemplified are citrus and solanaceous plants. Provided by the disclosure is a modified citrus or solanaceous plant that is resistant or tolerant to Sec-dependent effectors secreted by bacteria. Also provided by the disclosure are methods of modifying a plant genome plant to provide tolerance or resistance to species of *Ca. Liberibacter*. Still further provided by the disclosure are methods conferring a population of plants with tolerance or resistance to species of *Ca. Liberibacter* and screening that population for the plants that are tolerant or resistant to species of *Ca. Liberibacter.*

13 Claims, 11 Drawing Sheets

Specification includes a Sequence Listing.

(56) References Cited

OTHER PUBLICATIONS

Pitino, Marco et a.,"Transient Expression of Candidatus Liberibacter Asiaticus Effector Induces Cell Death in Nicotiana benthamiana", Frontiers in Plant Science, Jul. 2016, vol. 7, Article 982, 13 pages.

Wang, Nian et al., "The Candidatus Liberibacter-Host Interface: Insights into Pathogenesis Mechanisms and Disease Control", Annual Review of Phytopathology, Jun. 2017, vol. 13, No. 36, pp. 20.1-20.32.

* cited by examiner

| BD | AD | Mating control (DDO) | Selection (DDO/X) | Selection (DDO/X/A) | Selection (QDO) | Selection (QDO/X) | Selection (QDO/X/A) |
|---|---|---|---|---|---|---|---|
| 4025 | RLK2 | | | | | | |
| EV | RLK2 | | | | | | |
| 4025 | PR10 | | | | | | |
| EV | PR10 | | | | | | |
| 4025 | PP2B2 | | | | | | |
| EV | PP2B2 | | | | | | |
| Positive | | | | | | | |
| Negative | | | | | | | |

Figure 6A
A
MTISKNQAILFFITGMILSSCGDTLSDSKQHNKINNTKNHLDLLFPIDDSHNQKPTEKKPN
TSSIKIKNNIIEPQPGPSRWEGGWNGERYVREWER
B
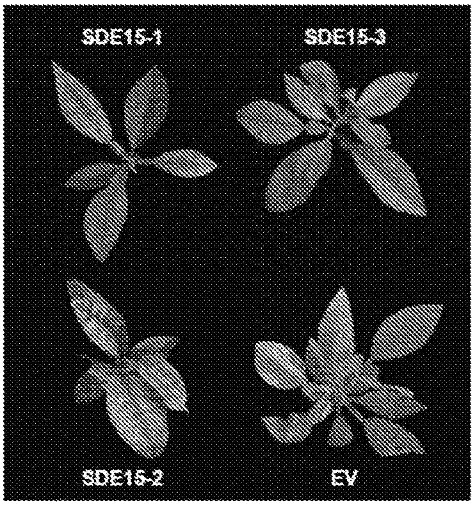
Figure 6B
C
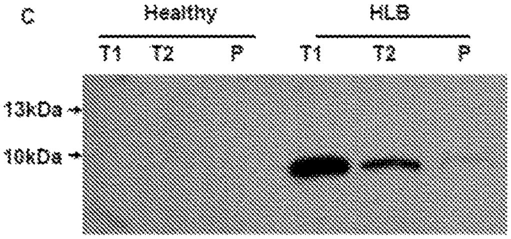
Figure 6C
D
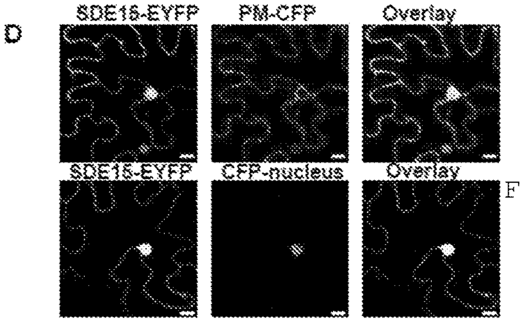
Figure 6D
E
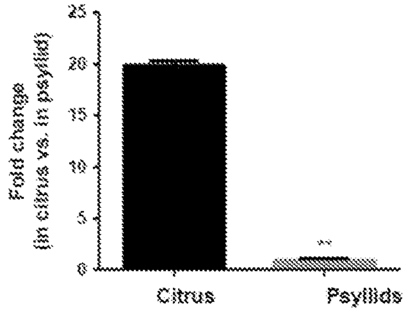
Figure 6E
F
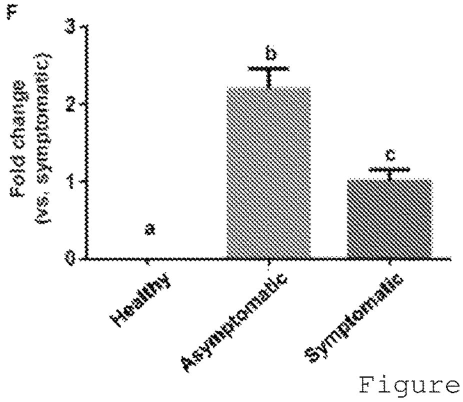
Figure 6F Las Ct Value (per 100ng DNA)

| | 0 mpi | 1 mpi | 2 mpi | 3 mpi | 4 mpi |
|---|---|---|---|---|---|
| SDE15 | 37.17±0.46 | 37.43±0.53 | 35.38±2.09 | 32.54±1.38** | 32.11±0.68** |
| EV | 36.51±0.50 | 37.06±0.73 | 36.60±0.66 | 34.88±1.05 | 34.17±0.90 |

Figure 10A
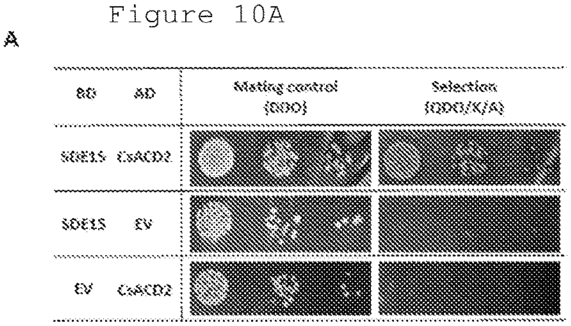
Figure 10B
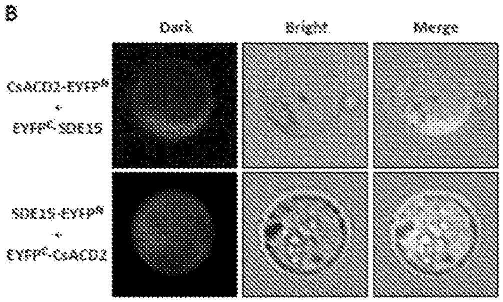
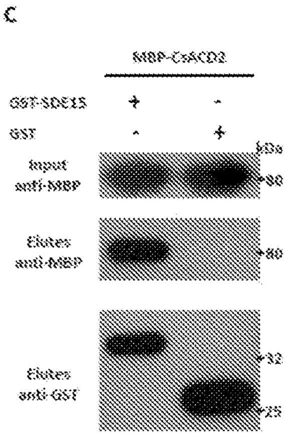
Figure 10C
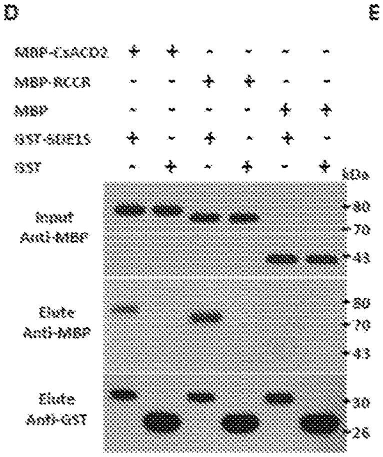
Figure 10D
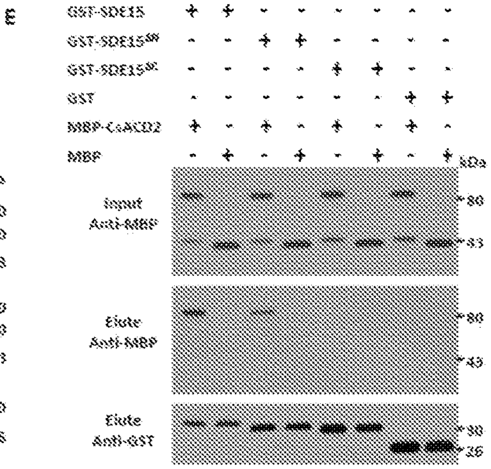
Figure 10E Figure 12A
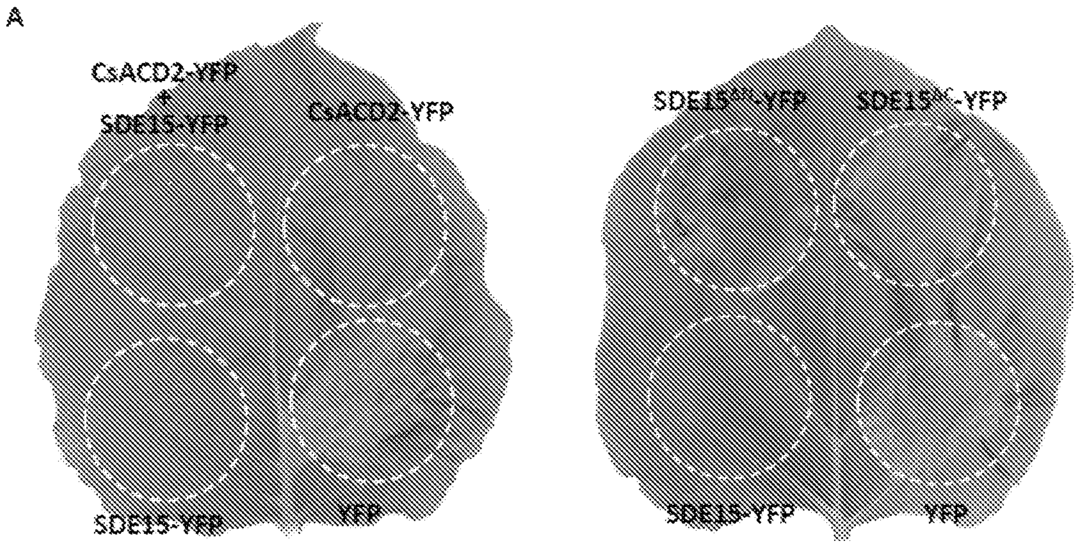
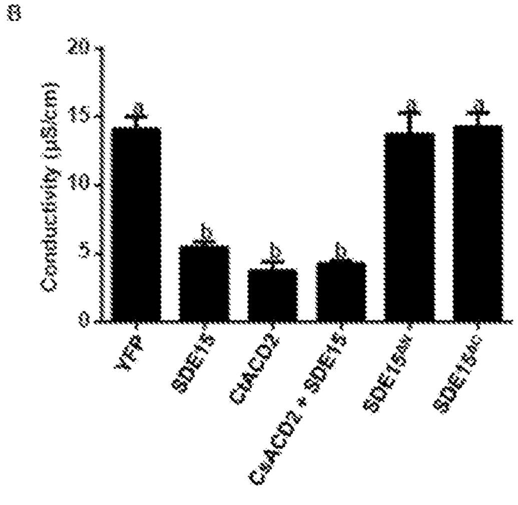
Figure 12B
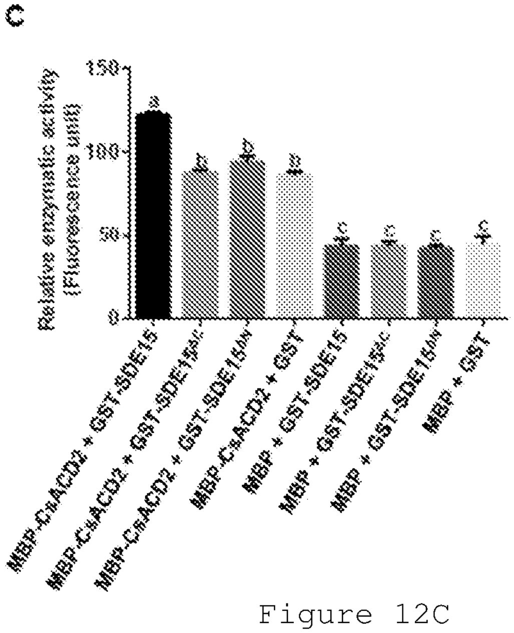
Figure 12C

SEQUENCE LISTING

```
<160> NUMBER OF SEQ ID NOS: 51

<210> SEQ ID NO 1
<211> LENGTH: 14
<212> TYPE: PRT
<213> ORGANISM: Liberobacter asiaticum

<400> SEQUENCE: 1

Asp Asp Ser His Asn Gln Lys Pro Thr Glu Lys Lys Pro Asn
1               5                   10


<210> SEQ ID NO 2
<211> LENGTH: 291
<212> TYPE: DNA
<213> ORGANISM: Liberobacter asiaticum

<400> SEQUENCE: 2

atgacaatat caaaaaatca agccattctt ttctttatta caggcatgat actttcttct      60
```

```
tgtggtgata ctctctctga ctctaagcaa cataataaaa tcaacaatac aaaaaatcat    120
cttgatcttc ttttcccaat agacgactcc cataatcaaa agcctacgga aaaaaaacca    180
aatacatcat ccataaagat aaagaacaat ataatagaac cacaacccgg ccctagtcgc    240
tgggaaggag gatggaatgg tgaaagatac gttagagaat gggaaagata a             291
```

<210> SEQ ID NO 3
<211> LENGTH: 156
<212> TYPE: DNA
<213> ORGANISM: Liberobacter asiaticum

<400> SEQUENCE: 3

```
atgtatacca aaagtttgtt aatggtagct tatttgttat cttcggttgc aatatcgggt     60
gggctatgct ttaaccgccc aaaaggcccg tctaaagaag aacaagcacg aatagaacaa    120
atacgagcag aagcaagaga aaggcgctac caataa                              156
```

<210> SEQ ID NO 4
<211> LENGTH: 1227
<212> TYPE: DNA
<213> ORGANISM: Liberobacter asiaticum

<400> SEQUENCE: 4

```
atgtttcaaa ataagaattt tttattaggc gttttgcgtc taaaaaagtg cacgcgtggt     60
gtttttttag ttattacagc tattttattg tcttcttttg tcgccatagt agatgttgtg    120
gtagatcagg tgacggtgat gcagaaaaca gcttggcttc aagaggtctt ggatcatgtt    180
atttatcgca cttctccaaa aaatttatat gatttaaggg aagcgggtag agataatttt    240
ataagacatc aaattgaaaa ggctttaaat acttataatt ccagagatct ttcaaatatt    300
gggagtatag aatcaatcgt taaagatgct gttattttaa cgaaaaatgt taattctttg    360
cctttacaat ttactgtcga catcgccctt tcgacaacgg ttcaattgcg aggatctctt    420
ttgcagatgt tttcgcaatc gaagggtaaa gttgatattt ctcgtcgaaa aaaagttatg    480
tataaacaaa atattggttt aatgattatg ccttttgcat gggatggcta ttggctagct    540
tcaagaggaa aggttgcaga ctcaaaagta catcctccaa agtatttgga gtattctcat    600
tattatcagc agtatcttaa tagaaatacg cttgtgaaaa attttctctc acaaattcct    660
tataaaaatt tctgtatggc tccttatcat tattcttcta ttctttattg ggcagtcgga    720
accttgacgt atagcgtgga taacaagacg actacgcgcg aatattataa ggatccttac    780
tatgctacat gggatcattt tccttattca tttatcaaga acgtatttga catgacttcc    840
aatcaatttg gagatgggca ggtattgact aataccaatc attgctttcc tcatggagca    900
agtcagaata aatatatgtt gatgcttgcg ataggaaatc agctatctcg aagttcagta    960
gagaaagaaa aaatagaaaa ggttctgcaa gactgccatt acatgcataa gcgtcataga   1020
actggaagag atgcaattac catattttct gtaggatttt ctccggatca agatacgcga   1080
tatactttaa gacaatgtgc aagtgatcca tctaaatatt atgaaattaa ttctgacgag   1140
aatgtcatgc ctatagccaa aagtcttgca cgtaatgtta taactaattg gtttagtcag   1200
tttacaatta ctgtggtcga tagctag                                        1227
```

<210> SEQ ID NO 5
<211> LENGTH: 678
<212> TYPE: DNA
<213> ORGANISM: Liberobacter asiaticum -continued

<400> SEQUENCE: 5
atgagagata taagaaaaat tagaaattat tttaggaata ctgctaaaat tatattgagt 60
gggttatttc tagggttttt ttcttctgct gcaatggcag actatgggta ttctccccag 120
tttcagccga ctataatggt gtccaatttt gcaaaattta aagggttata tgttgctgct 180
gatttttcca aaatagatca tcagtcgcct gttcgtttgc aaaatctttc tttaaatggg 240
gtgtccattg gtcttgatgg tcaagatgga acccttgttt atggtgcttc tttgggtgtc 300
gagggatttc atcttgaacc acgaggggga attgatgggg ataaggtagc gggaacactc 360
ttgtttcgta ccggttttac gtttgataat aataattctt ctattctcca aaatactctt 420
atttatgggt ttggtggagc tcgtataaga aatattatgt ctgttgaatc tgctgacaca 480
gcaaaatcca caatacgaaa cattgtagca aacggttttt tagataaagt tattggtgtg 540
gggattgaaa agaaacttgc tagcatgctc tcgattcgtg gtgagtatcg ttatgtcgct 600
tgttatgacc agccttggga tgtcagcaag tggagagaaa aaggtgactt cacagctggt 660
gtggttttac gcttttaa 678

<210> SEQ ID NO 6
<211> LENGTH: 150
<212> TYPE: DNA
<213> ORGANISM: Liberobacter asiaticum

<400> SEQUENCE: 6
atgaatacaa gaataatagg aaccgtatta atgcttgcta ttagtcctct tttatttagc 60
tgttcttcta aaaaaggagg tgaaaaaaaa ggtgcggaga aaaaaacttc tgctccgttg 120
aaaaatggta aaaatcaatc cagaagatag 150

<210> SEQ ID NO 7
<211> LENGTH: 1607
<212> TYPE: DNA
<213> ORGANISM: Citrus sinensis

<400> SEQUENCE: 7
ataagcaagt ggccaagtag tgatttgacg gagtgattaa gaacgaatgg ctgtgaacca 60
cttatgccag tggcagtatt tacgcttcca gctctctcat ccatcggctc cggcttgcag 120
atatttatct ccttcgagac caaagtcctc aacgtcgtca accgccaaag tcaattgttc 180
tgccgcacca tcgtcgtctc cgatggactc gcacaacgaa ggccgtaaga agttcatgga 240
attcccctac gcttcaggcc ctgttaggca gctgatggtt gatctcgtat caacggtgga 300
gaataccctc gattcgcagc tactcccttg cactctgcca ccagatgtac agtattacga 360
gaaccaaaat ggcactgctc aagcttctct tcaaatcaga tccgggctca agtcctcact 420
ggtagttctt tcttttacat aattggcgtt tgtttaattg cgagttgcaa cttgagtgaa 480
tttgtctcat aacttgattt aacctgaaac taggcgcctc tcttaaacat tggaactgaa 540
cgcatttatg tctgaaatag attttctttt cttagcctag gattgcacta ctctgcttag 600
ttgcctaagc ataagaaaca aatgattcaa aatttactag gctctagtgt gacattcaag 660
ttcgaggcgt acatggtctt caataatttg atgataatgg atgcgtgtca gattgatttc 720
atactgggaa gttgggtaca cagtgagcta ccaacaggag cagcattgaa cataacaagc 780
ctttcagcat atctaaactc ttccactgat gcaccaaact tgctaattga gctcatccag 840
agtagcccta cttctctagt cctcatcctt gacttgcctc ctcgaaagga tcttgtcctc 900
catcccgact atcttcacac tttctatgaa agcacacggt tggatgaata taggcaaatg 960

```
cttgagaaag tacctgaagt tagaccctac ttctcttctt ccctttactt aagatgtgtc   1020

gtctctcctt cagcaattat ggtccgtgta gatactgaaa ctgaaactgg ggcaggtgaa   1080

tcaacacgtt tggactatat tataacaaat catgtgcatc ctgttgctaa gcaagttatt   1140

ggaatctggc taaatcagtg tgcttgtgga gggagacatg taggggagtc agacaaggct   1200

tatctggaaa agagggatgg gttgattaag aacaaaacta ttgagattga tctcggctct   1260

agctttccga gattgtttgg accgcaggta gcaagccggg tattaggcga gatacagaag   1320

gtttttactg cctgaggttg gtatttgaat ttgaggttgg gaatgtacaa agaattggag   1380

ttgattgacc ttaattttag tgtgtgtatg aacatcattg tccccctttt tatgcacaag   1440

ttctttgatt tcttcctgta attgatatgg cacttaaatt actgttgctt tctaatctta   1500

ttcgaattgg ttaaaatttc gtgcatgtat ggtgtttcta atcttgtaaa gcatgaagaa   1560

aggaacttac aacaatctca attaggaatg gaattgaatc ccttgaa                 1607
```

<210> SEQ ID NO 8
<211> LENGTH: 1434
<212> TYPE: DNA
<213> ORGANISM: Citrus sinensis

<400> SEQUENCE: 8

```
atttgacgga gtgattaaga acgaatggct gtgaaccact tatgccagtg gcagtattta     60

cgcttccagc tctctcatcc atcggctccg gcttgcagat atttatctcc ttcgagacca    120

aagtcctcaa cgtcgtcaac cgccaaagtc aattgttctg ccgcaccatc gtcgtctccg    180

atggactcgc acaacgaagg ccgtaagaag ttcatggaat tcccctacgc ttcaggccct    240

gttaggcagc tgatggttga tctcgtatca acggtggaga ataccctcga ttcgcagcta    300

ctcccttgca ctctgccacc agatgtacag tattacgaga accaaaatgg cactgctcaa    360

gcttctcttc aaatcagatc cgggctcaag tcctcactga ttgatttcat actgggaagt    420

tgggtacaca gtgagctacc aacaggagca gcattgaaca taacaagcct ttcagcatat    480

ctaaactctt ccactgatgc accaaacttg ctaattgagc tcatccagag tagccctact    540

tctctagtcc tcatccttga cttgcctcct cgaaaggatc ttgtcctcca tcccgactat    600

cttcacactt tctatgaaag cacacggttg gatgaatata ggcaaatgct tgagaaagta    660

cctgaagtta gaccctactt ctcttcttcc ctttacttaa gatgtgtcgt ctctccttca    720

gcaattatgg tccgtgtaga tactgaaact gaaactgggg caggtgaatc aacacgtttg    780

gactatatta taacaaatca tgtgcatcct gttgctaagc aagttattgg aatctggcta    840

aatcagtgtg cttgtggagg gagacatgta ggggagtcag acaaggctta tctggaaaag    900

agggatgggt tgattaagaa caaaactatt gagattgatc tcggctctag ctttccgaga    960

ttgtttggac cgcaggtagc aagccgggta ttaggcgaga tacagaaggt ttttactgcc   1020

tgaggttggt atttgaattt gaggttggga atgtacaaag aattggagtt gattgacctt   1080

aattttagtg tgtgtatgaa catcattgtc cccctttttta tgcacaagtt ctttgatttc   1140

ttcctgtaat tgatatggca cttaaattac tgttgctttc taatcttatt cgaattggtt   1200

aaaatttcgt gcatgtatgg tgtttctaat cttgtaaagc atgaagaaag gaacttacaa   1260

caatctcaat taggaatgga attgaatccc ttgaacatct tgttgaactg ttggtagatt   1320

aattaactcg ctagaatggg tgtgattgat gcactgaaga atatgaaatt tatttctgca   1380

tgattctact ctcatctcat cataatggtt tgatcactct gctgagcctt aaag         1434
```

<210> SEQ ID NO 9
<211> LENGTH: 960
<212> TYPE: DNA
<213> ORGANISM: Arabidopsis thaliana

<400> SEQUENCE: 9
atggcgatga tattttgcaa cactctctac tcttcttctt ctccatcata tctctcgccg 60
ttaacttcaa aaccgtcgcg attctcaaag aatctcagac ctcgagctca attccagtcc 120
atggaagacc acgacgatca cctccgccga aaatttatgg agttcccgta tgtgtcaccc 180
acgcggaagc agctcatggt tgatctcatg tcgacggtgg agaatcgcct ccaatcacaa 240
ctccttccct gtaacctccc tccagatgta cgaaacttca ataaccctaa cggttccgcc 300
gaagcatctc ttcatatcag atccggcgac aaatcttctc cgattgattt tgttatagga 360
agttggatac attgcaagat cccaacagga gtatctttga atataacaag catctctgga 420
ttcttaaact catcaacaaa agctccaaac tttgtggtcg aactaataca gagcagttcc 480
aagtcgcttg tgctaatcct tgacctccca catcgtaaag atcttgttct taacccggat 540
tatctcaagg agtattacca agacactgct cttgattctc atcgacaatc tctccttaag 600
ctacctgaag ttaaccctta tgtgtctcct tctctctttg tccgttctgc tttctctcct 660
actgcttcga tgcttaagat tgatgcggag gaagaggata agttggagga gatattgaga 720
gatcatgtta gtccagctgc taaggaggtt ctcgaggttt ggttggagcg gtgtgtgaag 780
gaagaagaag agaagattgt ggttggggaa gaagagagaa tggagttgga gagaagagat 840
aaaagcttta gaaggaagag catagaggac gatttggatt tgcagtttcc gagaatgttt 900
ggtgaagaag tttcctcccg tgttgtacac gctattaaag aagctttcgg tgttctctag 960

<210> SEQ ID NO 10
<211> LENGTH: 318
<212> TYPE: PRT
<213> ORGANISM: Arabidopsis thaliana

<400> SEQUENCE: 10

Met Ala Met Ile Phe Cys Asn Thr Leu Tyr Ser Ser Ser Ser Pro Ser
1 5 10 15

Tyr Leu Ser Pro Leu Thr Ser Lys Pro Ser Arg Phe Ser Lys Asn Leu
20 25 30

Arg Pro Arg Ala Gln Phe Gln Ser Met Glu Asp His Asp Asp His Leu
35 40 45

Arg Arg Lys Phe Met Glu Phe Pro Tyr Val Ser Pro Thr Arg Lys Gln
50 55 60

Leu Met Val Asp Leu Met Ser Thr Val Glu Asn Arg Leu Gln Ser Gln
65 70 75 80

Leu Leu Pro Cys Asn Leu Pro Pro Asp Val Arg Asn Phe Asn Asn Pro
85 90 95

Asn Gly Ser Ala Glu Ala Ser Leu His Ile Arg Ser Gly Asp Lys Ser
100 105 110

Ser Pro Ile Asp Phe Val Ile Gly Ser Trp Ile His Cys Lys Ile Pro
115 120 125

Thr Gly Val Ser Leu Asn Ile Thr Ser Ile Ser Gly Phe Leu Asn Ser
130 135 140

Ser Thr Lys Ala Pro Asn Phe Val Val Glu Leu Ile Gln Ser Ser Ser
145 150 155 160

Lys Ser Leu Val Leu Ile Leu Asp Leu Pro His Arg Lys Asp Leu Val

-continued

```
                165                 170                 175

Leu Asn Pro Asp Tyr Leu Lys Glu Tyr Tyr Gln Asp Thr Ala Leu Asp
            180                 185                 190

Ser His Arg Gln Ser Leu Leu Lys Leu Pro Glu Val Asn Pro Tyr Val
        195                 200                 205

Ser Pro Ser Leu Phe Val Arg Ser Ala Phe Ser Pro Thr Ala Ser Met
    210                 215                 220

Leu Lys Ile Asp Ala Glu Glu Glu Asp Lys Leu Glu Glu Ile Leu Arg
225                 230                 235                 240

Asp His Val Ser Pro Ala Ala Lys Glu Val Leu Glu Val Trp Leu Glu
                245                 250                 255

Arg Cys Val Lys Glu Glu Glu Glu Lys Ile Val Val Gly Glu Glu Glu
            260                 265                 270

Arg Met Glu Leu Glu Arg Arg Asp Lys Ser Phe Arg Arg Lys Ser Ile
        275                 280                 285

Glu Asp Asp Leu Asp Leu Gln Phe Pro Arg Met Phe Gly Glu Glu Val
    290                 295                 300

Ser Ser Arg Val Val His Ala Ile Lys Glu Ala Phe Gly Val
305                 310                 315


<210> SEQ ID NO 11
<211> LENGTH: 3154
<212> TYPE: DNA
<213> ORGANISM: Citrus sinensis

<400> SEQUENCE: 11

cagtgtgctc tctccaaaca aagcagacac aatcattagg catggctcgc cccgtacagt      60

tggtctcgtc cgtcatcttg ttgctttgct gcgctgccgc agcatcagca tcagcatcaa     120

gcttcgacga ctccaatccg atcagattgg tatcatcgga cggtctccgt gacttcgaga     180

cctccgtcct ccaggtgatc ggccaagccc gccatgctct ctcctttgcc cgttttgctc     240

gcaggtatgg gaagatttac gagtccgttg aggagatgaa gctccggttc gcgactttct     300

ccaagaactt ggatttaatc agatctacca attgtaaagg cctatcttac aggctcgggt     360

tgaacagtaa gtttttcatt ttgaatattg gtctgtagct caggaggcca gtcaagccat     420

ctgattgcct agattcctga ttggtctgta gttcacgtta gtcacgtgct ttcctataac     480

aatctacgca ctagaaatga atttttacga ttttattatt attactgtta ttgttatgcc     540

catattttta ccaaaactca acttcgatga cataaaatga aagtgtgagg gcccaattta     600

attaggataa aacaatacaa actctaactc tcatcaaatt cagtattacg cgataagaga     660

taaaaatttt ctaattaatt atactgttta cttcaattat atatattttt tttttcatat     720

acgcgtgttc ttagttattc tatttgattt gtatagggat tttgtacaaa tatattattt     780

ctcatcatag taactagtat tttgtgatct tcatttcttg ggaaccaatc atggattgat     840

gatgctttag cttatgtagt gattctgtag ttccctcagt agattaatca cggatggtta     900

taggttataa ttggataatc aagcttcaaa cttatatttt tgcattcatt tgtgtatctc     960

gtgcaatcta gtagtaaata tttatagtga aaatgaaaga ggtattaaaa ctgtcttatt    1020

tctactattg gattgtacaa aataacgaga atttgtataa aaaatttaag atcgtattta    1080

ctaaagttac actagtatta ttgattgcta attaactcta tacaattgtt gttgatggcg    1140

tttaaatgta attaacataa cacgcagagt ttgctgactg gagctgggaa gagttccaaa    1200

ggcacaggtt gggagctgcg caaaactgct ctgccactac aaaaggaaat cacaagctta    1260
```

```
ctgctgatgt gcttccagaa acggtaattc tacgaaatac tattctcgat tgaacaacca   1320

agatgaccat cagtttctat aagcttgtat tttgtattac atagagagga aaagactgat   1380

ttttctgctg ctatatgtgt agaaagactg gagggaatct ggcatagtaa gcccagttaa   1440

agaccaaggt cactgtggat cttgctggac tttcaggtca gcttgatttg gaatgaaatc   1500

agaatttcta aactgagttt tcaattttag tgctaaataa ttaccttttg cagcacgact   1560

ggatctcttg aggctgctta ccaccaggcc tttggaaagg gtatctcttt gtcagaacag   1620

cagcttgtag actgtgccca agctttcaac aaccagggat gcaatggtgg gttgccatcc   1680

caagcctttg aatacatcaa gtacaatggt ggccttgata ctgaggaagc atatccctac   1740

accggaaaag atggtgtctg caaattctca tctgaaaatg ttggcgtcca agtcctggac   1800

tcagtcaaca ttaccttggt gagttttatg ctgaattttc attttaaatg agagtagagt   1860

ctgcagtact ggactcacta catgccaaac aaatgaaaat caaccataaa taaatcaatc   1920

ataatctaga aactctggat atgtatatgt ttcaagtttc atgacttgta agacaatgca   1980

gggtgctgaa gatgaattac agcatgcagt tggtcttgtt cgacctgtga gtgtggcatt   2040

tgaagtagta gatggattcc gattttacaa gagtggagtt tacagcagca ctaaatgtgg   2100

aaatactccc atggtgagtc ttattgactt ggaaaacgat acattatttt gataggcatt   2160

gaatgcaaat ctgttaaaaa atgttttgat ttatgttcaa aatcaaaatt taacagggca   2220

ttcaagtttt gaagttttgc aaaacaaata aatgcctaac attatggtcc aaactctcca   2280

aacaacattt ctcattttct tttctgaact tctcagttgg tcaacatgtt actcacgcaa   2340

ggaatgctta atgtagacgt tgtgtaaatg atccttcact tggaattatc acccaagcat   2400

taaccactca tccgatgcat ttattgcatt tctaactttc gggattttat ggcaggatgt   2460

gaaccatgcc gtcgttgctg ttgggtacgg agttgaagat ggtgttccat attggctgat   2520

taagaactct tggggagaga actggggcga tcatggctac tttaagatgg agatggggaa   2580

gaacatgtgt ggtaagttac tgttacatct agattgtcag taccagatca ttgctcacaa   2640

cttaaattat cagtcatcgt caattttcgt catcatcaat tttcagtatg acctaagata   2700

tgatgtcaat aaaagaaaca gaataatgta gtatacatcc gataagtctt gataagttaa   2760

cagagtagta acagatctac gcatgaaatt tgaaacattt aaataggtga tatatatttg   2820

tgtttgctga ttttactgat ttgattgtag gtattgcaac ttgtgcatca tacccagttg   2880

tggcttagtc tgctcctgaa gaaatagttg gatctggcta tcagcaagtc atttgctcat   2940

aaaacttata ttatttcact caagaatgat agcagaatgg ttggctttat gtacgaaata   3000

aattcggaga ttaatgtcca tataatctac aatagcaatg catggctgct tgatgttcaa   3060

aataaattct gagatctatg tccatgtaaa cagtcattgt gactaggaca ccaacgatgt   3120

tatatatatt ttgtcaatgc aaggtagttg ttat                               3154
```

<210> SEQ ID NO 12
<211> LENGTH: 2059
<212> TYPE: DNA
<213> ORGANISM: Citrus sinensis

<400> SEQUENCE: 12

```
cctcttttgt gataaaaatg taagtaaaat attttgtacg attacaaatc attcctatat     60

taacagaaat gaacgctata acggcagaga aaaaaaccgt tacgacgacg tgaaggaatt    120

tcacgagaac gtcatcgcgc gcgtcagagt tagttcctat cgtctacgat acgacaaagc    180

cagcttagac gcccgttcta atctacaaat ttccaatcca tccctcagac tgaaaatgat    240
```

```
acggaatctt gagtcttgac ttatcttgca cccgacgagg catctcataa taataataat    300

aataataata ataataataa taataataca caactcattt caaccacata aattatgaat    360

ctcataattt tatataattg agatgaatta tgtaagttac attgaagata acttagcact    420

tgccgaataa taatagtgtt catagactgc attcatttaa tccgaagccc ttgagtgcag    480

tgtgctctct ccaaacaaag cagacacaat cattaggcat ggctcgcccc gtacagttgg    540

tctcgtccgt catcttgttg ctttgctgcg ctgccgcagc atcagcatca gcatcaagct    600

tcgacgactc caatccgatc agattggtat catcggacgg tctccgtgac ttcgagacct    660

ccgtcctcca ggtgatcggc caagcccgcc atgctctctc ctttgcccgt tttgctcgca    720

ggtatgggaa gatttacgag tccgttgagg agatgaagct ccggttcgcg actttctcca    780

agaacttgga tttaatcaga tctaccaatt gtaaaggcct atcttacagg ctcgggttga    840

acaagtttgc tgactggagc tgggaagagt tccaaaggca caggttggga gctgcgcaaa    900

actgctctgc cactacaaaa ggaaatcaca agcttactgc tgatgtgctt ccagaaacga    960

aagactggag ggaatctggc atagtaagcc cagttaaaga ccaaggtcac tgtggatctt   1020

gctggacttt cagcacgact ggatctcttg aggctgctta ccaccaggcc tttggaaagg   1080

gtatctcttt gtcagaacag cagcttgtag actgtgccca agctttcaac aaccagggat   1140

gcaatggtgg gttgccatcc caagcctttg aatacatcaa gtacaatggt ggccttgata   1200

ctgaggaagc atatccctac accggaaaag atggtgtctg caaattctca tctgaaaatg   1260

ttggcgtcca agtcctggac tcagtcaaca ttaccttgca tgcagttggt cttgttcgac   1320

ctgtgagtgt ggcatttgaa gtagtagatg gattccgatt ttacaagagt ggagtttaca   1380

gcagcactaa atgtggaaat actcccatgg atgtgaacca tgccgtcgtt gctgttgggt   1440

acggagttga agatggtgtt ccatattggc tgattaagaa ctcttgggga gagaactggg   1500

gcgatcatgg ctactttaag atggagatgg ggaagaacat gtgtggtatt gcaacttgtg   1560

catcataccc agttgtggct tagtctgctc ctgaagaaat agttggatct ggctatcagc   1620

aagtcatttg ctcataaaac ttatattatt tcactcaaga atgatagcag aatggttggc   1680

tttatgtacg aaataaattc ggagattaat gtccatataa tctacaatag caatgcatgg   1740

ctgcttgatg ttcaaaataa attctgagat ctatgtccat gtaaacagtc attgtgacta   1800

ggacaccaac gatgttatat atattttgtc aatgcaaggt agttgttata tggaagcttt   1860

aggcaaatat caatgcattg cttaaaaaat ttggttgtct tctgccctaa aaaggaactg   1920

agaacttgct gtgagaatga tcgtgtgttc attgtgacat ctgcctacta gatgccattc   1980

aattcatgct ctctacaggc cttttcatta tcataatttg ttgctgaaaa ataagggcac   2040

ttagcagctt aacctctta                                                2059


<210> SEQ ID NO 13
<211> LENGTH: 2080
<212> TYPE: DNA
<213> ORGANISM: Citrus sinensis

<400> SEQUENCE: 13

cctcttttgt gataaaaatg taagtaaaat attttgtacg attacaaatc attcctatat     60

taacagaaat gaacgctata acggcagaga aaaaaaccgt tacgacgacg tgaaggaatt    120

tcacgagaac gtcatcgcgc gcgtcagagt tagttcctat cgtctacgat acgacaaagc    180

cagcttagac gcccgttcta atctacaaat ttccaatcca tccctcagac tgaaaatgat    240
```

-continued

```
acggaatctt gagtcttgac ttatcttgca cccgacgagg catctcataa taataataat    300

aataataata ataataataa taataataca caactcattt caaccacata aattatgaat    360

ctcataattt tatataattg agatgaatta tgtaagttac attgaagata acttagcact    420

tgccgaataa taatagtgtt catagactgc attcatttaa tccgaagccc ttgagtgcag    480

tgtgctctct ccaaacaaag cagacacaat cattaggcat ggctcgcccc gtacagttgg    540

tctcgtccgt catcttgttg ctttgctgcg ctgccgcagc atcagcatca gcatcaagct    600

tcgacgactc caatccgatc agattggtat catcggacgg tctccgtgac ttcgagacct    660

ccgtcctcca ggtgatcggc caagcccgcc atgctctctc ctttgcccgt tttgctcgca    720

ggtatgggaa gatttacgag tccgttgagg agatgaagct ccggttcgcg actttctcca    780

agaacttgga tttaatcaga tctaccaatt gtaaaggcct atcttacagg ctcgggttga    840

acaagtttgc tgactggagc tgggaagagt tccaaaggca caggttggga gctgcgcaaa    900

actgctctgc cactacaaaa ggaaatcaca agcttactgc tgatgtgctt ccagaaacga    960

aagactggag ggaatctggc atagtaagcc cagttaaaga ccaaggtcac tgtggatctt   1020

gctggacttt cagcacgact ggatctcttg aggctgctta ccaccaggcc tttggaaagg   1080

gtatctcttt gtcagaacag cagcttgtag actgtgccca agctttcaac aaccagggat   1140

gcaatggtgg gttgccatcc caagcctttg aatacatcaa gtacaatggt ggccttgata   1200

ctgaggaagc atatccctac accggaaaag atggtgtctg caaattctca tctgaaaatg   1260

ttggcgtcca agtcctggac tcagtcaaca ttaccttggg tgctgaagat gaattacagc   1320

atgcagttgg tcttgttcga cctgtgagtg tggcatttga agtagtagat ggattccgat   1380

tttacaagag tggagtttac agcagcacta aatgtggaaa tactcccatg gatgtgaacc   1440

atgccgtcgt tgctgttggg tacggagttg aagatggtgt tccatattgg ctgattaaga   1500

actcttgggg agagaactgg ggcgatcatg gctactttaa gatggagatg gggaagaaca   1560

tgtgtggtat tgcaacttgt gcatcatacc cagttgtggc ttagtctgct cctgaagaaa   1620

tagttggatc tggctatcag caagtcattt gctcataaaa cttatattat ttcactcaag   1680

aatgatagca gaatggttgg ctttatgtac gaaataaatt cggagattaa tgtccatata   1740

atctacaata gcaatgcatg gctgcttgat gttcaaaata aattctgaga tctatgtcca   1800

tgtaaacagt cattgtgact aggacaccaa cgatgttata tatattttgt caatgcaagg   1860

tagttgttat atggaagctt taggcaaata tcaatgcatt gcttaaaaaa tttggttgtc   1920

ttctgcccta aaaaggaact gagaacttgc tgtgagaatg atcgtgtgtt cattgtgaca   1980

tctgcctact agatgccatt caattcatgc tctctacagg ccttttcatt atcataattt   2040

gttgctgaaa aataagggca cttagcagct taacctctta                         2080
```

```
<210> SEQ ID NO 14
<211> LENGTH: 2243
<212> TYPE: DNA
<213> ORGANISM: Citrus sinensis

<400> SEQUENCE: 14

caaactcacc gaaaattaat taaatctaat ctataataca aatacaaaaa cattaactac     60

cacgattgta taatgatatt tttgaatatt ccttcccact gaaagctctg tgcgaaaggg    120

ggaagtcaaa agtgttattc gttgttgtct atggctatga gttcgccact ttgggtagcc    180

ccaactttc tttctcgtcc atcgtcaaat atatcgagat caattactta caaacgttgc    240

aggtcttcgg caagtaactt tttctcacaa tcagacatgg agcagccgct gatgaagggg    300
```

-continued cagaagctga tggaattccc tcacctgacg gcggcgcaca aagatctgat ggttagctta 360
atctcagcct tggagactag gcttgactct catcttcttg cttcttcggt agtccctcct 420
gatgttgagt tttatcagaa tgaccaaggc acttctcagg gttctcttca tatcagacgt 480
ggccttcctt cctctcatgt actcgcttcc tctccctctc gtgtccagat tcaaattcac 540
tgttgcttat tcatatttat attattggtc attttaatct cgttaaatct ggatatatat 600
atatatatat atatatatat agggcactgt tccaatccgg attggaacag cctccgggaa 660
tggtttgggg atcattatat atatatatat atataattat ttttaagtgt ggacgctcgt 720
tttttttgtt tttttataca gacactacgg tacagcagtt tttatacaga cactcttaaa 780
tcgtgtggtt taaaaaatta gtttttaaat aaactatata tatatatata tatattttat 840
tgcgaccgtc cttatttttt ttattcatgc tgatatactt taaaattaca gggtttaaga 900
gagttagttt ttaacacttt aaaactgcac ggttttataa ttcattcaat atatataaaa 960
ttatttttag gtgcggacat ccgcattttt ttaatcatga acacactttt aaaccgaaaa 1020
gattagttat tgaatgaact ataaaatcat gtaattttta agagtgtccg cgtaaaaaaa 1080
aaaataaagg catcctctag agaatgacta tatatatata taatggtttt tggaatttga 1140
atgattaata accaccatgg agtcaattat caatcttaat gttaattggg atactgctga 1200
tcgcttttct cagcatgctt atagtagcta gctacatctt tccaaaactt atgtaaacat 1260
cctcctcttt tatgaacaat atactaggaa gtggtactag tgtactactc taaataattg 1320
actacctata tttttttcca aaaattctat caaaatcctc ctctttcatg aacaatttaa 1380
atgggttaat attacgagag cccacttgtt ttcaagtgac gcttgctgga tattacactt 1440
tgtataataa atgcttgtgg gaatgggaat ctttttttctt ttttttttta acttttgctt 1500
ttggcatggt aacagattga tttcgtatta gcaagttggc ttcacttgaa ggtaccaacg 1560
ggaagtgcca tgaacataac caatcttcaa gcttacctaa aatcatcaac cgatgtacca 1620
cattttcaat tcgagcttgt ccaatgcagc cccacatatt tcattctctt cctagatata 1680
actcctagaa aagaccttgt tctataccca aattacctca aaacatttta cgaagaagct 1740
cagcttgaaa cattgagaca gagacttgag caagtcccag aaaccaaacc ctacttgagt 1800
tcctctcttt actttcgtgg tgtggtctcc ccaactggga ttttggtcag cataaaaatgt 1860 gaggaagttg gtggaacgga tcgctgtgaa gagattatac gtgaacatgt gagccctata 1920
gctcatgatg tgatggtgat ttggttggag aagtattttt ctggagcaac tgttggggta 1980
actgagagag ctgaattgga gaagagagat cttttggtta agactagagc catagagatg 2040
gacctgagtt ccagtctgcc cttgcagttt ggacaagaag tggcaaatcg agttttgagt 2100
gttattaaag gtgttttggg tgtgtagggt agaaaagtgg ggagctccag attgcaagga 2160
attatagaat atattaaggt ggtgtttggt tgggaagaga gactagagga aatgaaagta 2220
atttaaattc tcgttttttt tta 2243

<210> SEQ ID NO 15
<211> LENGTH: 1085
<212> TYPE: DNA
<213> ORGANISM: Citrus sinensis

<400> SEQUENCE: 15
tgcgaaaggg ggaagtcaaa agtgttattc gttgttgtct atggctatga gttcgccact 60
ttgggtagcc ccaacttttc tttctcgtcc atcgtcaaat atatcgagat caattactta 120

-continued

```
caaacgttgc aggtcttcgg caagtaactt tttctcacaa tcagacatgg agcagccgct    180
gatgaagggg cagaagctga tggaattccc tcacctgacg gcggcgcaca aagatctgat    240
ggttagctta atctcagcct tggagactag gcttgactct catcttcttg cttcttcggt    300
agtccctcct gatgttgagt tttatcagaa tgaccaaggc acttctcagg gttctcttca    360
tatcagacgt ggccttcctt cctctcatat tgatttcgta ttagcaagtt ggcttcactt    420
gaaggtacca acgggaagtg ccatgaacat aaccaatctt caagcttacc taaaatcatc    480
aaccgatgta ccacattttc aattcgagct tgtccaatgc agccccacat atttcattct    540
cttcctagat ataactccta gaaaagacct tgttctatac ccaaattacc tcaaaacatt    600
ttacgaagaa gctcagcttg aaacattgag acagagactt gagcaagtcc cagaaaccaa    660
accctacttg agttcctctc tttactttcg tggtgtggtc tccccaactg ggattttggt    720
cagcataaaa tgtgaggaag ttggtggaac ggatcgctgt gaagagatta tacgtgaaca    780
tgtgagccct atagctcatg atgtgatggt gatttggttg gagaagtatt tttctggagc    840
aactgttggg gtaactgaga gagctgaatt ggagaagaga gatcttttgg ttaagactag    900
agccatagag atggacctga gttccagtct gcccttgcag tttggacaag aagtggcaaa    960
tcgagttttg agtgttatta aaggtgtttt gggtgtgtag ggtagaaaag tggggagctc   1020
cagattgcaa ggaattatag aatatattaa ggtggtgttt ggttgggaag agagactaga   1080
ggaaa                                                               1085
```

<210> SEQ ID NO 16
<211> LENGTH: 3474
<212> TYPE: DNA
<213> ORGANISM: Citrus sinensis

<400> SEQUENCE: 16

```
agaaaacaac aaataaaaat tgcgtcattc cttcatgttg ggcaatttgc agcctcaagc     60
tcacggttcc ctgatcatga ctcatggcat gactcgtgtt cgtttcacaa ctatcaataa    120
ttgcctcaag ttttaatctt gcttgatctc tagtttgtgt tgagaacggt gctgcatgca    180
gccatggaag ctcttagact ctcctcggtt tcaccttttt gtaacgctac attcaaactt    240
gagtacaata agacccactt cactaagccc aagttcttaa gctttcagtt cagttccctg    300
tccactttat catctttctc atcaaaacca tacaaaatct tcaccacctt atcaccatcg    360
tcacaagttt caactgaagc cacagaccca ccagaaagag agcttgaaac taactcacaa    420
gaggagaaat ttgattggtt ctcacagtgg tatccattga tgccggtgtg tgatttggac    480
aagagagtcc ctcatgcaaa gaaagtgttg gggcttgatg tcgtggtttg gtgggacagg    540
aatgagaatg aatggagagt ctttgctgat gcttgtcctc acagattggc tcctttgtca    600
gaaggaagaa ttgatcaatg gggaaggctt cagtgtgtgt atcatggctg gtgcttcagt    660
ggctcgggtg actgtaaatt tatccctcag gctcccccag acggcccccc ggtaacatct    720
attgcttcac ttttgcatca cattcatatg ttttattatg ttttgtgttg ctatagatgc    780
ttttgcggtt gtctcgctta tgtgtagagt gagatgctat agttttgtcc aattagaatc    840
tcttctaggc atagagtttg tttgtttata attgttgcgc ttcagcgcgt tttttgcccg    900
aaagctatcc cggaaggact tacagactgg aagtaataaa ataggtcaag ggtctaattc    960
caaggggata cgtttaattc tgaaagagca gtagctaatt aaatgtttgg taaagccgcc   1020
acacctctca tcttcagttt aattgtgaag gaacaatgaa agataagggg aatacatgaa   1080
ttatgattcc attgcttgct tgataaaatt ttgttttgat ttttctgcaa tctagttttg   1140
```

-continued

```
atttttgtt cttgcatgca gttgttgtta agatttctac tttgctgggt ggctgattgc   1200
tttaattttt accaacttat ttgtcaaaat atgtaggtcc acacattcga gaaagcatgt   1260
gcagcagttt atccaagtac cgtccagcat gacatcgtat ggttttggcc aaatattgct   1320
cctcggtaca aggatattat caagactaag aaacctcctc acatcccgga actagatgac   1380
ccgtcattca caaaattgtt tggaacaga gatatacctt atgggtatgc aatgatccag   1440
tcttccattt taatttgagc gagttagcac acgaaattct agattgaatt tgtactatac   1500
tgatatttgg caagagtcat taagaaaact agttgaactt aagtgtaatg acaacctggt   1560
caatgcaagt taacaacttt ttctaattgc aagtaagttg cattttcagt tatgaggtct   1620
tattggaaaa tcttatggac cctgctcatg ttccatatgc acattacgga ttgatgcgta   1680
caaggaaacc caaaggttga taaattccta gataaacctt gttctacgtt taagtcattt   1740
atattctctt cgtgaataaa acctattagt taatactaaa ttttctttac agtgaagctc   1800
gatagagaag ggggaagacc agttgaaatg agtgtcaata aaatagacat aaatggtttc   1860
attggaaagc aggagtgggg aagtagcaaa tttttggcac cttgtatctt ttttgcttat   1920
actgatctta tgaaggatca agaaaatgga tctgcatcat cagcaggagc cgaaaaggta   1980
aaggtcaata tgtttcatta tgctcagctg acagtagaat tttgcactct tttcagttct   2040
tattctatgc tgtttgggct ttcttttatc catatacatt tcggttggtg cagaagctgg   2100
agcaacaaag agcagctctg atttttattt gtgttccagt tagtcctggt cacagcagat   2160
taatatgggc gttcccaaga aactttcaaa cttggataga caaagttgtt ccgcggtgga   2220
tatttcatat tggacagaat ctaattcttg attcagattt atacctgctt cacgttgagg   2280
tgattcctgt ctctgtatgc taaaataatt ttaacctaaa gttttttgaa aatgctgagt   2340
ggattggcgt tcaagtctac tgctagtcta ggcctcaaac tcagatttga gactcgtcga   2400
ccatttcatt ttactagatt ggttgtgaca ccatccaaaa agcatatttt tgtttttctt   2460
ctcaatagaa ggtattcact taaatactac tctcctacaa tagaagaatt taatagattc   2520
tttcttgttt ctggctgtga attacctgac ttctgtttct ctctgcagga gcgaaagata   2580
atggatgttg gccctgctaa ttggcagaaa gcttgttttg tgccaacaaa agccgatgcc   2640
ctggtagttg gtttcaggag gtggttaaaa aaatatgccg gtggccaatt caattgggga   2700
gggaaattca atgcgactct tccaccaaca ccgcccaggg aacagctcat ggacaggtat   2760
ctgggcttca cttttataaa cttgaacccc ttaacaccat gtcatgggat tttacagtag   2820
ttcccagttt tgaaactcat ataaagagca gaggtttatg gatatttaaa agaagcatta   2880
tttgtttctt caagcttgag aaacattttc ttttgtgttt tgccaaattt cttatgcaat   2940
gccttgaaaa cgggaacact gtgaagtttg ttgtgacccc attaaaacat aagatttcgt   3000
acttaattaa aggaatttta ttcaaatttg caggtactgg tctcatgtgg tgaattgcaa   3060
aagttgcaat gcggcacaca agagtctcag cgcacttgag gtcacgctac aagtcgtctc   3120
cattgcttca attgggattg ttgctacaac caagcagaat gccatgtcaa tggctacaag   3180
aactacaatc atctcatttg cagtaatctg ctttgcggct tcaaaatggt tgtctcactt   3240
catctacaaa acctttcatt atcatgacta caatcatgcc cttcgctgag cttagcattt   3300
aacgtcgaaa attagaatat gtaaatacaa cttatttttc tgtacgtaaa tactggaatg   3360
tagcttgtat gcaaacattt tgatcaagtg aaattagaaa gtgcagttgt aatagaaaac   3420
atataattat catcaccatt agcagttgta attgtaagta cattatcatc acca         3474
```

<210> SEQ ID NO 17
<211> LENGTH: 2093
<212> TYPE: DNA
<213> ORGANISM: Citrus sinensis

<400> SEQUENCE: 17

```
atgcttcaga aaacaacaaa taaaaattgc gtcattcctt catgttgggc aatttgcagc      60
ctcaagctca cggttccctg atcatgactc atggcatgac tcgtgttcgt ttcacaacta     120
tcaataattg cctcaagttt taatcttgct tgatctctag tttgtgttga gaacggtgct     180
gcatgcagcc atggaagctc ttagactctc ctcggtttca cctttttgta acgctacatt     240
caaacttgag tacaataaga cccacttcac taagcccaag ttcttaagct ttcagttcag     300
ttccctgtcc actttatcat ctttctcatc aaaaccatac aaaatcttca ccaccttatc     360
accatcgtca caagtttcaa ctgaagccac agacccacca gaaagagagc ttgaaactaa     420
ctcacaagag gagaaatttg attggttctc acagtggtat ccattgatgc cggtgtgtga     480
tttggacaag agagtccctc atgcaaagaa agtgttgggg cttgatgtcg tggtttggtg     540
ggacaggaat gagaatgaat ggagagtctt tgctgatgct tgtcctcaca gattggctcc     600
tttgtcagaa ggaagaattg atcaatgggg aaggcttcag tgtgtgtatc atggctggtg     660
cttcagtggc tcgggtgact gtaaatttat ccctcaggct cccccagacg gccccccggt     720
ccacacattc gagaaagcat gtgcagcagt ttatccaagt accgtccagc atgacatcgt     780
atggttttgg ccaaatattg ctcctcggta caaggatatt atcaagacta agaaacctcc     840
tcacatcccg gaactagatg acccgtcatt cacaaaattg tttgggaaca gagatatacc     900
ttatggttat gaggtcttat tggaaaatct tatggaccct gctcatgttc catatgcaca     960
ttacggattg atgcgtacaa ggaaacccaa agtgaagctc gatagagaag gggaagacc     1020
agttgaaatg agtgtcaata aaatagacat aaatggtttc attggaaagc aggagtgggg    1080
aagtagcaaa tttttggcac cttgtatctt ttttgcttat actgatctta tgaaggatca    1140
agaaaatgga tctgcatcat cagcaggagc cgaaaagaag ctggagcaac aaagagcagc    1200
tctgattttt atttgtgttc cagttagtcc tggtcacagc agattaatat gggcgttccc    1260
aagaaacttt caaacttgga tagacaaagt tgttccgcgg tggatatttc atattggaca    1320
gaatctaatt cttgattcag atttatacct gcttcacgtt gaggagcgaa agataatgga    1380
tgttggccct gctaattggc agaaagcttg ttttgtgcca acaaaagccg atgccctggt    1440
agttggtttc aggaggtggt taaaaaaata tgccggtggc caattcaatt ggggagggaa    1500
attcaatgcg actcttccac caacaccgcc cagggaacag ctcatggaca ggtactggtc    1560
tcatgtggtg aattgcaaaa gttgcaatgc ggcacacaag agtctcagcg cacttgaggt    1620
cacgctacaa gtcgtctcca ttgcttcaat tgggattgtt gctacaacca agcagaatgc    1680
catgtcaatg gctacaagaa ctacaatcat ctcatttgca gtaatctgct ttgcggcttc    1740
aaaatggttg tctcacttca tctacaaaac ctttcattat catgactaca atcatgccct    1800
tcgctgagct tagcatttaa cgtcgaaaat tagaatatgt aaatacaact tatttttctg    1860
tacgtaaata ctggaatgta gcttgtatgc aaacattttg atcaagtgaa attagaaagt    1920
gcagttgtaa tagaaaacat ataattatca tcaccattag cagttgtaat tgtaagtaca    1980
ttatcatcac cattaacaat tgcaagagaa aacgtataca caactgaacc acggcttcag    2040
aatgaacaca agaagaacat ttttactagt tttcacaatg gtatctagtg atg           2093
```

<210> SEQ ID NO 18
<211> LENGTH: 4930
<212> TYPE: DNA
<213> ORGANISM: Citrus sinensis
<220> FEATURE:
<221> NAME/KEY: misc_feature
<222> LOCATION: (2243)..(2277)
<223> OTHER INFORMATION: n is a, c, g, or t

<400> SEQUENCE: 18

```
ccttgcttga tctcgatttt tgtgcagagt aaggtgttgc atgcagccat ggaagctctc     60
ttactctcct cagtttcacc attttataac actccattaa aacttaagta caacagaacc    120
cacttcactg ctaagcccaa gctcttaagc ttccacttca gtccactatc cactttatca    180
tctttctcat caaaaccatc caaactcttc accaccttat caccatcatc tcaagtttca    240
actgaagcca cagacccacc agagacagag cctgaaacta actcacaaga ggaaaaattt    300
gattggttct cacagtggta tccattgatg ccggtgtgtg atttggacaa gagagtcccc    360
catgcaaaga aagtgttggg gcttgatgtc gtggtttggt gggacaggaa tgagaatgaa    420
tggagagtct ttgccgatgc ttgtcctcac agattggctc ctttgtcaga aggaagaatt    480
gatcaatggg gacggcttca gtgtccgtat catggctggt gcttcagtgg ctcgggtgac    540
tgtaaattta tccctcaggc tcccccagac ggcccccccgg taacatcgat tgcttcactt    600
ttgcatcaca ttcatatgtt ttattatttt ttatgctgct atgtatgctt ttgcggtttt    660
cttgattacg tctagagtga gatgctactt ccttgctata ttttggtcta attagattcc    720
ctgaaggact aaaagactgg aagtaataaa ataggtcaag ggcctaattc caatgggata    780
cgtttaattc tgaaagaact gtagctaatt taatgtttga taaagccacc acacctctcg    840
tcttcagttt gattgtgagg aaacaacgaa agataagcag aatacatgag ttatgattcc    900
atttcctgct tgataaaatt ttgtagtgat ttttctgcaa tctagtattg attttcgttc    960
ttgcatgcag aagttgttaa gaattctact ttgctgggtg gctgattgct ttaattttta   1020
ctgacttatt tatcaaaata cgcaggtcca cacatccaag aaagcatgtg cagctgttta   1080
tccaagtgcc gtacagaatg gcatcctatg gttttggcca gatattgctc ctcagtgcaa   1140
ggatattatc aagactaaga aacctcctca catcccggaa ctcgatgacc cgtcatttac   1200
aaaaatgttt ggaagcaggg atgttcctta tgggtatgca gtgatccggt tttccatttt   1260
taatttgaaa ttccagtttg aatttgtacc atattgatat ttggcaacaa tcattaagaa   1320
aactagttga actcaagtgt aatgacagcc gggtaaatgc aagttaacag ctttttctaa   1380
gtgtaagtaa attgcatttt cagatatgag gtcctaatgg aaaatcttat ggatcctgct   1440
catcttacat atgcacatta cggaatgatg cgtacgagga aacccaaagg ttgataaatt   1500
cctggataaa ccttgtttta cgtttacgtc aactatatta ataaaaccca ttagctaatg   1560
ctaaattttc tttacagtga tgctcgatag agaaggggga agaccaatca aaataagttt   1620
cgagaaaata gacataaatg gtttcattgc aaagcaggat tcggaaagtg ccaaattttt   1680
ggcaccttgt gtctttgttg tttattttga tcttctggag aatcaggaaa atggatctgc   1740
atcatcggga ggagccgaag aggtaagagt caatatgttt cgtaatgctc agctgacgga   1800
tagaattttg cactcttttc accccctatt ctatgttgct cccgcattgt ttgtccatat   1860
aaatttcgat cggtgcagaa gctgaagcaa cgaagagtag ctatgatttt tatttgtgct   1920
ccagtaagtc cgggtaacag cagagtaatc tgggccttcc caagaaactt ccagatttgg   1980
atagacaaag ttgttccgcg gtggatattt catattggac agaacctaat tctggattca   2040
```

-continued

```
gatttatgcc tgcttcacgt tgaggtgatt cctatctctg tatgctaaaa taattttaat   2100
ctaaagtttt tggaacatgc cgggtggatt ggcgttaaat tggagtgcta ggtagcattt   2160
atttattttg tctgaaattt caatgagtga ataaatctct ctctctctct ctctctctct   2220
ctctctatat atatatatat atnnnnnnnn nnnnnnnnnn nnnnnnnnnn nnnnnnncat   2280
atatatgaat aacatgttta tttttcttat tttgatatat gaatataagt gttattaaaa   2340
aaaaaaatga catcttctat atctatagag aagccaattt cgttgtagat tatatggcga   2400
acctcacttt ttctcttcct tttggccttc ttgtgtacac tgccccacct ctaggtgtta   2460
ggtctctttt gcttcataac ttttacgggg tttctcaccc ccgttctgtt cttctttagc   2520
tctttttaga gccccagttc aataaataaa taaataaata aaatatgata ttttgaaata   2580
tataacatca taaatattaa caatacttat attttttttt attaaacaca tgacaagttg   2640
taaataaatt atttgattag taaaaaaaat ttaataatgt tttccttaac agagcacgaa   2700
aaataaaata tgtatctaac acacaatata tgatacttat gttgttattt ttagtatatt   2760
atattgattt ttttaattac atatgtcaat taaagattgt ttaatcattt gaattaaatt   2820
taatgtatta aataaaattc aaaatctatt ataaaaatgg caaatataaa taccaagaga   2880
taggtccagt ggcggattta aaaaaataat ttaccggggg ctaaattaga taataataaa   2940
atatgaaaaa ttaaaatttt aaatatataa aatatttgct agtacattta taattattct   3000
ctgcgcattt ttatatttta aaaatgttat acaattgact cattatcaat attattaaat   3060
ttattgtttc gtatataaac aatcaagttc aaatttaaat tttatggaga tttataattt   3120
atagtgatta ttttaataaa ttttttatgg gggttaatta aaaaactaaa atatttttct   3180
tttttaattt taatttttta ttttgccagt gggggctcaa gcccccacta gtcacatgct   3240
agatccgccc ctggataggt ctattataaa acacactcat ctaaagttcg attatgttca   3300
aaattctaat tcacaatata tatatatata tagttgaata catgtatata accaaaaaaa   3360
ggtaaataaa aaataataaa attatttata tgatagggaa taaatttatt taatatgaat   3420
attaacgaga gagaatatta aaattacatt taaatatttt acaatttaga taaaagttgt   3480
agtatttaac tttttgtatt tagatctaaa catcttataa ttagatataa gtaataaaaa   3540
aaagacagta aatatcataa aacaattaag attcaaactg agaaaaaaaa aatcaaacaa   3600
cccctgctcc tccagtctag gcctcaaact cagatattag actcgtcaac catttcattt   3660
tactagattg attgtgacac catccgaaaa gcatattttt gtttttcttc tcaatagaaa   3720
gtgttgatta aaataacact ttgttgattt aaatactact ttcctacgat aaaagaaatg   3780
aatagcttct ccgttgtttc tagccgcgaa taaaattctc tgcaacatat tgttacctga   3840
ctttggtttc tccctgcagg agcgaaagat aatggctgtt ggccctgcta attggcagaa   3900
agcttgtttt gtgccaacaa aatccgataa cctggtagtt ggtttcagga tgtggttaaa   3960
aaaatattcc ggtggccaat tcaattgggg aggaaaattc gatgcaactc ttccaccaac   4020
actgccaaga gaacagctca tggacaggta tttgggcttc acttcaataa acttgaatcc   4080
cttaacgccc tgtagttctt ggttttgaag aaagagcagg gatttatgga tttttaaaag   4140
aagcattatt tatttcttca ggcttgggaa acattttctc ttgtgttttt gccaaaattc   4200
ttatgcaatg ccttgaaaac gggaacaata taaagtttgc tgtgacccca ttaaaacgta   4260
agatcttgtg cttaattaaa ggaactttat tcaaattttc aggtactggt ctcatgtggt   4320
gaactgcaaa agttgcaatg ctgcacacaa gagtctcaat gcacttgagg tcatactgca   4380
agtcgtctct gttgtttcag ttgggattgt tgctgcaacc aagcagaacg ccatgtcaat   4440
```

ggctacaaga gctacgatcg tgtcatttgc agtaatctgc tttgcagctt caaaatggtt 4500
gtctcacttt gtctacaaaa cctttcatta tcatgactac aatcatgctc ttcgctaagt 4560
ttagcattgg taatactgta acttttaaaa taattgctat tacttatagc gttgaaataa 4620
tctgccgtga gcaaaatcaa tttaaaaact gataaatttt attttaaaaa atattgtgtc 4680
ttaaaaaata gtcgtatata agtttacatt ggtcataatg ttgaataaaa tttaggaaaa 4740
ttatcattcg tgtaccctaa agatgcactt ttatcaaaca tattacaaca ctttcaaggt 4800
gtatcactca tccacccaaa aataccaaaa tatatctacc caccactatt ccgttagcca 4860
ccgtttgcaa actaacagaa ttgttgcgaa atgacaaata tgcccttaaa actaaaaaaa 4920
aacgcaaaaa 4930

<210> SEQ ID NO 19
<211> LENGTH: 2237
<212> TYPE: DNA
<213> ORGANISM: Citrus sinensis

<400> SEQUENCE: 19
cacaaacata agagacgcat taatttatgt tggacttttc agcgtcacgg tcagagtcca 60
ctgatcatga ctcatgtggc gcacgttcat tcgcaattag ctataattat ctcgagttct 120
aaccttgctt gatctcgatt tttgtgcaga gtaaggtgtt gcatgcagcc atggaagctc 180
tcttactctc ctcagtttca ccattttata acactccatt aaaacttaag tacaacagaa 240
cccacttcac tgctaagccc aagctcttaa gcttccactt cagtccacta tccactttat 300
catctttctc atcaaaacca tccaaactct tcaccacctt atcaccatca tctcaagttt 360
caactgaagc cacagaccca ccagagacag agcctgaaac taactcacaa gaggaaaaat 420
ttgattggtt ctcacagtgg tatccattga tgccggtgtg tgatttggac aagagagtcc 480
cccatgcaaa gaaagtgttg gggcttgatg tcgtggtttg gtgggacagg aatgagaatg 540
aatggagagt ctttgccgat gcttgtcctc acagattggc tcctttgtca gaaggaagaa 600
ttgatcaatg gggacggctt cagtgtccgt atcatggctg gtgcttcagt ggctcgggtg 660
actgtaaatt tatccctcag gctcccccag acggcccccc ggtccacaca tccaagaaag 720
catgtgcagc tgtttatcca agtgccgtac agaatggcat cctatggttt tggccagata 780
ttgctcctca gtgcaaggat attatcaaga ctaagaaacc tcctcacatc ccggaactcg 840
atgacccgtc atttacaaaa atgtttggaa gcagggatgt tccttatgga tatgaggtcc 900
taatggaaaa tcttatggat cctgctcatc ttacatatgc acattacgga atgatgcgta 960
cgaggaaacc caaagtgatg ctcgatagag aaggggggaag accaatcaaa ataagtttcg 1020
agaaaataga cataaatggt ttcattgcaa agcaggattc ggaaagtgcc aaatttttgg 1080
caccttgtgt ctttgttgtt tattttgatc ttctggagaa tcaggaaaat ggatctgcat 1140
catcgggagg agccgaagag aagctgaagc aacgaagagt agctatgatt tttatttgtg 1200
ctccagtaag tccgggtaac agcagagtaa tctgggcctt cccaagaaac ttccagattt 1260
ggatagacaa agttgttccg cggtggatat ttcatattgg acagaaccta attctggatt 1320
cagatttatg cctgcttcac gttgaggagc gaaagataat ggctgttggc cctgctaatt 1380
ggcagaaagc ttgttttgtg ccaacaaaat ccgataacct ggtagttggt ttcaggatgt 1440
ggttaaaaaa atattccggt ggccaattca attggggagg aaaattcgat gcaactcttc 1500
caccaacact gccaagagaa cagctcatgg acaggtactg gtctcatgtg gtgaactgca 1560
aaagttgcaa tgctgcacac aagagtctca atgcacttga ggtcatactg caagtcgtct 1620
ctgttgtttc agttgggatt gttgctgcaa ccaagcagaa cgccatgtca atggctacaa 1680
gagctacgat cgtgtcattt gcagtaatct gctttgcagc ttcaaaatgg ttgtctcact 1740
ttgtctacaa aacctttcat tatcatgact acaatcatgc tcttcgctaa gtttagcatt 1800
ggtaatactg taacttttaa aataattgct attacttata gcgttgaaat aatctgccgt 1860
gagcaaaatc aatttaaaaa ctgataaatt ttattttaaa aaatattgtg tcttaaaaaa 1920
tagtcgtata taagtttaca ttggtcataa tgttgaataa aatttaggaa aattatcatt 1980
cgtgtaccct aaagatgcac ttttatcaaa catattacaa cactttcaag gtgtatcact 2040
catccaccca aaaataccaa aatatatcta cccaccacta ttccgttagc caccgtttgc 2100
aaactaacag aattgttgcg aaatgacaaa tatgccctta aaactaaaaa aaaacgcaaa 2160
aagacataaa taccccacaa accaagcaaa gaaaaataga tccgttagag acaataacag 2220
ttgtattttt tggctat 2237

<210> SEQ ID NO 20
<211> LENGTH: 4421
<212> TYPE: DNA
<213> ORGANISM: Citrus sinensis

<400> SEQUENCE: 20
ccggtttttc ttctttttc cgttttctga attctggaag cgtgaataca gacagacagc 60
tgggagaatt ggaggggcaa attgcaaact tgcacgcaaa gtcctcttct ttttctgtct 120
ctctctcgaa agctcacttt attttcgctt cactagaatt ggaaaaatca tacaaaaatt 180
ttcattaaac tcaaagcaaa aggacatggc gctacttctt tctactactg ctaatatcac 240
cacatcacca agaaaaaccc ttccattttt ggccacagga accccgaagc gacaaatcac 300
ggtaaaaagc ttgcaaaaga gaagcaagaa tttgtctcca ctacgagtgg cagctcctcc 360
ttcagaccct gcagcatcag atgaagaaac gatgagaaaa gatgagaaag aagattatgg 420
atcattggtc gatgatgagt atggtaaaga gagttcggat tctaagtttt cttggaggga 480
tcattggtac ccagtttctt tagttgaaga tttggacccg aacttgccta caccgtttca 540
gcttcttggg agagacttag ttctttggtt tgataacaat tctaataaat gggttgcatt 600
tgatgataaa tgccctcata gactcgcccc attatcggta atctattcta ttgttcctct 660
tgatctctgt aattttgtga tcgaggtgaa acatagaaga taaaattgta atttgctcat 720
tttttattta attttcgata ttatagtggt aatggaagaa gtaatatctg ttgttgtatc 780
ttattttctt tttaagaaat gaaatttgaa tggaggtttt tctaggatct agagtgaagg 840
atatgaaatc taatttacaa attcatatct tgttctgttc ttgatcagtt tatccaagga 900
aagcctcaca tatagtcata tgaatgacca attttttgtc gttttcgata tagaatccga 960
aattcagaat tttgggagct gtttgtttga ccattgatgt ttaatcttgg tagctaagtt 1020
gggaattatg tttcttagat catgtgattg atgggttcct taaaatttta taggaagggc 1080
ggatcgatga aaatgggcat ttgcagtgtt cataccatgg atggtctttt gacgggtgtg 1140
gatcttgcac tcgcattccc caagcagcat ctgaaggtcc tgaagctcgt gcaattcagt 1200
ctcccagagc gtgtgctacg aggtttccta caatggtgtc tcaaggtctg ctattcgttt 1260
ggccagatga gaatggtcag gaaagagcca atgccaccaa gccaccaatg taattgactc 1320
tatttctctc ttctgttttt agattatgca ttgactgaat taccgacttt gccggttcat 1380
taaacctgtg tggtaatgtt taggttgcct gatgactttg acaaacctga gttctcatcg 1440

-continued

```
gtcacaattc agcgggatct attttatggc tatgacactc tcatggaaaa tgtctcagat   1500
ccttcccaca ttgattttgc acatcacaag gtacatactg aatttcaatg gtagtgtcgc   1560
tgggtgcaag atggaaatgt catttgaaca atagctggtt ggtttaagat aattttgata   1620
tgaattaaat atggtagtca gctcttggtc gatatgtctc attaactaaa ctagaaacac   1680
agttatcgtc tcttgtcaag ttctttggtt ttcagtagtg tcaggaagtg cctgcaggta   1740
ttgttttctt agtggactga ttgaacacat agtggcgcag ctttttgttt acttggccat   1800
gttgtgcttt ccttctcagt cacttggaat ctcgtaacat cctagtactc atatacaggt   1860
catgttgttc tcattcatgg atatgtcctt gaacaaggag taaagtagtg aattctatac   1920
ccctatctcc tcattagatt gctataggaa tgtgacacta attgctctct ctgtggaaac   1980
aaatctccat gtaccttatt gagagacatc gtttgcaggt taccggcaga agggacaggg   2040
ccaagccttt accgtttaag ttggagtcta gtggacattg gggatttgct ggagccaatg   2100
atggaaaccc aaggataagt gctaaatttg ttgctccttg ttattacatg aacaagtaag   2160
ttctccactg tctggaccag caaaattaat acgtctagat agactatctc ctttcctgct   2220
tatgctctct cagtgatact taaaattgtt gattttttca agaactggag atttgaataa   2280
tttcccaaac ttacttcaaa agcgtttagt attcctgatg aaaacattgt gtgataaagt   2340
gtgaacctta accatcaaat atttcctcct accaagactc aagttcattt tgttaagcca   2400
atcaatggag gcttgtattt caaagttaga ggttgacttt tggttaactg gaggatttat   2460
gcacaaacgt agaactgagt tgttttgaca tcagctgtag ttcaaggaag ccgatgaaac   2520
atcatttcat gtcttaattg tgtttaaaat tgaatacaac tgttgacgaa ctttctgctg   2580
agttaggtga tagttttagt tgattgagta ctatatttgt ttatcagttc attctgcttc   2640
cgaaacttaa ctatccgtgt attgcttttc ttccaggata gagatagata caaaacttcc   2700
tgtagttggt gataaaaaat ggataatatg gatttgttcc ttcaacgtac caatggcacc   2760
agggaaaacc cgctcaattg tttgtagtgc acgaaacttc ttccagttca ctatgccagg   2820
acctgcctgg tggcaggtaa gaacatctca gttgtgtttc tgatgaaatt tgtataatgt   2880
gacacttgca tggaaacttt agtctaaaga gaacactcaa atgctgttga catgttcaag   2940
catacggaaa gtttatcttg ttaacacgct tgtgctagtg tgcacacaca tggttttagc   3000
ttccaattca ggtagttgat tgttcttatc ttggatacca tactgtccca tttgggaagg   3060
ggaagttttg gatgtctggc tgaaatgtgg agagaaaact ccttgatttg gagaagaaaa   3120
cttagttgag atgtatgctt aaaagttttc tccctgtttg agggcctttt cttagatatt   3180
ggcatccgtg tcttgtaaac tttctaaata atattattca tatttttcat gttgatgcca   3240
aagttccaat ctaaggggtt tgctgtcaga tttgataaga ctttgttgag ctgtattgtt   3300
gatgattttc ctccacatga aattagtttt ttaacggagt tatgtcctat ctccacctta   3360
gaaaactaga aatttaatat ttttacttcg taaattggtg aattatctac aaaatggctt   3420
ccgattttac caggtggttc ctagatggca cgagcattgg acttcaaata aggtctatga   3480
tggagacatg attgtcctcc aaggtcaaga gaagatcttt ctttcaaaat tgatggaagg   3540
ttctgaagat gttaacaagg agtacacaaa aattacgttt acacccacac aggcagatcg   3600
gcttgtgttg gcatttagaa attggctgag gcgacacggc aacagccaac ctgaatggtt   3660
cggcttcagc agccaacaac cttccccttc aacagtcttg tcgaaatgtc aggtacgaaa   3720
ccccttctcc attatttcaa gaaataaaaa atgaatattg ggattgaatt tagattttta   3780
```

-continued

```
aagtagatgg attcataatt tgtgttaagt gggacaatgt cacatttata ataagctcga   3840
ttaatatgtt attacacctt ctgggtttga tttcttcctt acgttttagt ttttctgttg   3900
ttgggttttg tttcagatgc tcgatagatt tgagcagcac accctcaagt gttcatcatg   3960
tagagaagct tattcagcat tccagacggg ccaaaagttt ctcattggcg cgaccgttgc   4020
attctgcgca acagctggga ttccttcaga tttgcaatca cggattgttt tggctgggct   4080
tgcactagtg agcgctgcct tggcttatgc tttgcatgaa ctacaaaaga attttgtgtt   4140
tgttgattat gtgcatgctg aaatcgatta gagagggagt agatatgctg ctgaaagaat   4200
caatgtgtcc agaggtataa gaaagatatg gtgataaatc ttgtcaaaat ttgcgagttt   4260
gtatatatct attagataga aatcagtgtg atagctaagc ttagagtgtt tcctcagtat   4320
tccctttgtt tttgtgccaa atgaatgtca tcagataaat atgtgcagac atgcatccaa   4380
attcatgagt aaatggatta aacaatatac actttgtcaa a                       4421
```

<210> SEQ ID NO 21
<211> LENGTH: 2334
<212> TYPE: DNA
<213> ORGANISM: Citrus sinensis

<400> SEQUENCE: 21

```
cacgaaacac gccattgcca aagggcatta cgggaatttt gtgccagaaa atgtgacagt     60
aaatgaccag cagccccttg actttctatt ctgttagaac ctttaattgg tgagaccaat    120
catacaaact aaaccacaaa gtacttgatc gcaaatcgga caatcagaaa aatcgagcta    180
accggttttt cttcttttt ccgttttctg aattctggaa gcgtgaatac agacagacag    240
ctgggagaat tggaggggca aattgcaaac ttgcacgcaa agtcctcttc tttttctgtc    300
tctctctcga aagctcactt tattttcgct tcactagaat tggaaaaatc atacaaaaat    360
tttcattaaa ctcaaagcaa aaggacatgg cgctacttct ttctactact gctaatatca    420
ccacatcacc aagaaaaacc cttccatttt tggccacagg aaccccgaag cgacaaatca    480
cggtaaaaag cttgcaaaag agaagcaaga atttgtctcc actacgagtg gcagctcctc    540
cttcagaccc tgcagcatca gatgaagaaa cgatgagaaa agatgagaaa gaagattatg    600
gatcattggt cgatgatgag tatggtaaag agagttcgga ttctaagttt tcttggaggg    660
atcattggta cccagtttct ttagttgaag atttggaccc gaacttgcct acaccgtttc    720
agcttcttgg gagagactta gttctttggt ttgataacaa ttctaataaa tgggttgcat    780
ttgatgataa atgccctcat agactcgccc cattatcgga agggcggatc gatgaaaatg    840
ggcatttgca gtgttcatac catggatggt cttttgacgg gtgtggatct tgcactcgca    900
ttccccaagc agcatctgaa ggtcctgaag ctcgtgcaat tcagtctccc agagcgtgtg    960
ctacgaggtt tcctacaatg gtgtctcaag gtctgctatt cgtttggcca gatgagaatg   1020
gtcaggaaag agccaatgcc accaagccac caatgttgcc tgatgacttt gacaaacctg   1080
agttctcatc ggtcacaatt cagcgggatc tattttatgg ctatgacact ctcatggaaa   1140
atgtctcaga tccttcccac attgattttg cacatcacaa ggttaccggc agaagggaca   1200
gggccaagcc tttaccgttt aagttggagt ctagtggaca ttggggattt gctggagcca   1260
atgatggaaa cccaaggata agtgctaaat ttgttgctcc ttgttattac atgaacaaga   1320
tagagataga tacaaaactt cctgtagttg gtgataaaaa atggataata tggatttgtt   1380
ccttcaacgt accaatggca ccagggaaaa cccgctcaat tgtttgtagt gcacgaaact   1440
tcttccagtt cactatgcca ggacctgcct ggtggcaggt ggttcctaga tggcacgagc   1500
```

```
attggacttc aaataaggtc tatgatggag acatgattgt cctccaaggt caagagaaga   1560
tctttctttc aaaattgatg gaaggttctg aagatgttaa caaggagtac acaaaaatta   1620
cgtttacacc cacacaggca gatcggcttg tgttggcatt tagaaattgg ctgaggcgac   1680
acggcaacag ccaacctgaa tggttcggct tcagcagcca acaaccttcc ccttcaacag   1740
tcttgtcgaa atgtcagatg ctcgatagat ttgagcagca caccctcaag tgttcatcat   1800
gtagagaagc ttattcagca ttccagacgg gccaaaagtt tctcattggc gcgaccgttg   1860
cattctgcgc aacagctggg attccttcag atttgcaatc acggattgtt ttggctgggc   1920
ttgcactagt gagcgctgcc ttggcttatg ctttgcatga actacaaaag aattttgtgt   1980
ttgttgatta tgtgcatgct gaaatcgatt agagagggag tagatatgct gctgaaagaa   2040
tcaatgtgtc cagaggtata agaaagatat ggtgataaat cttgtcaaaa tttgcgagtt   2100
tgtatatatc tattagatag aaatcagtgt gatagctaag cttagagtgt ttcctcagta   2160
ttccctttgt ttttgtgcca aatgaatgtc atcagataaa tatgtgcaga catgcatcca   2220
aattcatgag taaatggatt aaacaatata cactttgtca aatggaaagg agcgcatttc   2280
ctttaggaac aagcaaccac aaagtttagt catgaatcag tttgaaaaaa caat         2334
```

<210> SEQ ID NO 22
<211> LENGTH: 2321
<212> TYPE: DNA
<213> ORGANISM: Citrus sinensis

<400> SEQUENCE: 22

```
cgtcatgcaa tgaggagaaa ttaggtgtcg aaatctcata cgcggaccca accacaagtt     60
tcttctgtct ttttggaaac atttattatc tgcttcatcc tgctttgcag tccactgaaa    120
caaatcgaaa atggagcgcc ttattctctc ctctctcctc ctcctcctcc tatcttctgt    180
gcttgcgtcc gctgtagctg tcaacgacga cgatgctatg atcagacagg tcgtgccgtc    240
agacggcgaa caatccgaag atcatctcct gaacgcggag caccacttct ccctcttcaa    300
gtccaaattc tccaagactt acgccaccca ggaggagcac gattaccgat tccgcgtgtt    360
caaggctaat ctgcgccgag caaagcgacg ccagctcctg gaccccactg ctgtccacgg    420
tgtcaccaag ttctccgact taacgccgtc tgaattccgc cgtcagttcc ttggcttgaa    480
taggcggctt cggctgccag ctgacgctca aaaggctcct attctcccca ccaacgatct    540
tcctactgac tttgactggc gtgatcacgg cgccgttact ggcgtcaaag accaggtacg    600
ttagagaaag tgcttttttt ttttttcaaa aataaattg aaaaaaaataa ttgatttttg    660
ttgatatttt tttattaatg tatgtagggc gcatgtggat cgtgctggtc gtttagtgca    720
accggcgctt tggagggagc gcacttctta tcgacgggcg agcttgtcag cctcagtgag    780
caacagcttg tggactgtga tcacgaggtt tgttcaattg tttgttatat ttttaacgtt    840
agttaaatga tgaaaattac agattttgac tgattttgtt tgatagctag gatgagttgt    900
ataatttcta atcccaaaca gttagttatg acggtaaatc tcaaagttag attgggttct    960
cactctctga atttatgata aagaatttat atgtcagttt ccttttttct tttaatttct   1020
aatgttggtt cttcattatg ttaatctctt ttttttgttg gtttgatatt gttggatgcc   1080
ataatttgaa gttttgtggt gatatataat atcatataac tatccacaat atgttgggct   1140
tgtgcttttt gtattctcaa tattgactgt ttgagttgtt tggacgtttc cctctcaagt   1200
ctgaactcac atctcacatg atcaaagtgt atgatttgac aaatataatt atgtttatta   1260
```

-continued

```
atgcaagttt tgtttcattt ttcagtgtga tccagaggaa tctggttcat gtgactctgg   1320

gtgcaatggt gggctaatga actctgcctt tgagtacata ctcaaggctg gtggggttga   1380

gcgagagaag gactaccctt acactgggac cgacggtggt tcctgcaaat ttgacaaaag   1440

caaaattgct gcagctgtat ctaatttcag tgttatttcc tctgatgaag atcaaatggc   1500

tgcaaatttg gtgaaacatg gccctctggc aggtaatgta gcttcgatac aattacctca   1560

tatttcgttt tccgtttctt ggcttttctc ttcactgtga gctctccaaa ataacatttg   1620

gaaaagttag ttaattaatt aatttctttt gagatgttgg taattttttt attaaacgga   1680

atggatagaa tgatgacaga atttgtgctg atcttgctgt ttgcttttgc agtgggtatc   1740

aatgccgttt ggatgcaaac atatattgga ggagtttcat gcccatacat ttgcgggaag   1800

tatttggatc atggagtgct tatcgtgggc tatggatctt caggtttcgc cccgatccgt   1860

ttcaaggaga agccttactg gatcataaag aactcctggg gagagaactg ggagagagaat   1920

ggatattata agatctgcat gggtcgcaat gtctgtgggg tcgactccat ggtctcatct   1980

gtagctgctg tccatacaac ctcaagctag acattatgga ggttgtgcta ggcaagtgga   2040

gcttatatac gaagatatta taggatatcc ttttaaatag ccgtctgcaa ttataaggat   2100

gcctacatgc gtgggctgag gcatgaactt tatatgctct tgtaatattt aagcatatgt   2160

catgtcagaa tgtaatattt atccatttta tagttaacca tgctacagaa ttgttattga   2220

agatggtatt aatattttct ttttatattg ggcaggcttg tagaaatatt ataatgttat   2280

attttctttt tatgtaactc aaaatagtag aacttcacgt a                       2321
```

<210> SEQ ID NO 23
<211> LENGTH: 1890
<212> TYPE: DNA
<213> ORGANISM: Citrus sinensis

<400> SEQUENCE: 23

```
atttattata ataaaaaatt gttaccaata aattaataac ctaaaaaaaa aaattccaat     60

ggatgtatgg taaaggtgag tacgatcgat gcagtcatcc gtgacgccgg tttcttttgt    120

tttatagttc caatttgcag acttatatga ctaatcaaat ccgtcatgca atgaggagaa    180

attaggtgtc gaaatctcat acgcggaccc aaccacaagt ttcttctgtc tttttggaaa    240

catttattat ctgcttcatc ctgctttgca gtccactgaa acaaatcgaa aatggagcgc    300

cttattctct cctctctcct cctcctcctc ctatcttctg tgcttgcgtc cgctgtagct    360

gtcaacgacg acgatgctat gatcagacag gtcgtgccgt cagacggcga acaatccgaa    420

gatcatctcc tgaacgcgga gcaccacttc tccctcttca agtccaaatt ctccaagact    480

tacgccaccc aggaggagca cgattaccga ttccgcgtgt tcaaggctaa tctgcgccga    540

gcaaagcgac gccagctcct ggaccccact gctgtccacg gtgtcaccaa gttctccgac    600

ttaacgccgt ctgaattccg ccgtcagttc cttggcttga ataggcggct tcggctgcca    660

gctgacgctc aaaaggctcc tattctcccc accaacgatc ttcctactga ctttgactgg    720

cgtgatcacg gcgccgttac tggcgtcaaa gaccagggcg catgtggatc gtgctggtcg    780

tttagtgcaa ccggcgcttt ggagggagcg cacttcttat cgacgggcga gcttgtcagc    840

ctcagtgagc aacagcttgt ggactgtgat cacgagtgtg atccagagga atctggttca    900

tgtgactctg ggtgcaatgg tgggctaatg aactctgcct ttgagtacat actcaaggct    960

ggtggggttg agcgagagaa ggactaccct tacactggga ccgacggtgg ttcctgcaaa   1020

tttgacaaaa gcaaaattgc tgcagctgta tctaatttca gtgttatttc ctctgatgaa   1080
```

```
gatcaaatgg ctgcaaattt ggtgaaacat ggccctctgg cagtgggtat caatgccgtt   1140
tggatgcaaa catatattgg aggagtttca tgcccataca tttgcgggaa gtatttggat   1200
catggagtgc ttatcgtggg ctatggatct tcaggtttcg ccccgatccg tttcaaggag   1260
aagccttact ggatcataaa gaactcctgg ggagagaact ggggagagaa tggatattat   1320
aagatctgca tgggtcgcaa tgtctgtggg gtcgactcca tggtctcatc tgtagctgct   1380
gtccatacaa cctcaagcta gacattatgg aggttgtgct aggcaagtgg agcttatata   1440
cgaagatatt ataggatatc cttttaaata gccgtctgca attataagga tgcctacatg   1500
cgtgggctga ggcatgaact ttatatgctc ttgtaatatt taagcatatg tcatgtcaga   1560
atgtaatatt tatccatttt atagttaacc atgctacaga attgttattg aagatggtat   1620
taatattttc tttttatatt gggcaggctt gtagaaatat tataatgtta tattttcttt   1680
ttatgtaact caaaatagta gaacttcacg tatgcttaga cgcttgtatt ttcttattat   1740
atttgaagtt agctctattt agctctgttc atattaagaa atttcacaca actgccaagt   1800
ttgtgactgc ctgaccagtg tcactggttt aatagtctta tatgcttcta agtagcctaa   1860
gattacttag acttctcttt ataaactggt                                    1890
```

<210> SEQ ID NO 24
<211> LENGTH: 1977
<212> TYPE: DNA
<213> ORGANISM: Citrus sinensis

<400> SEQUENCE: 24

```
gaaattgatt tcagaaccag taaccaatat tcttcccaaa tatatcagtg ttaagttaca     60
aacacttctt gaaggatggg catttgcact ccgacaataa atactatcca tggaagcaca    120
atcacaagaa aagcaaaacc tggagcctgg taaaatgcca tcaagcatca tttctagtta    180
tcatttacaa gaactggctt ctgcttttta tctaacagat caatgtttct ttggatttca    240
tcaaaatcaa cacaaaaata atgaagttat agaagcttca ttaccaccat caaatcaatt    300
ttccggggat aatttttcca agaagttgtc tgagctagac actttggaat cattggtatt    360
atcgagcaac cgcaacagta aatttcccag aaaaaatagc agctttccca ctccttctga    420
gagcagccaa aatactaaag taagtttctt gtgttacctt acattatata atatatgtaa    480
ttattacatc aatcgattat tttcttttct gaattttgac ctgtgtatat aaccttttttt   540
tttttttgc atcactatag aatatgtctg aattttgacc tgtgtatata accttctttt    600
ctgaattttg acctgtgtat ataacctttt tttttttttt gcatcactat agaatatgag    660
catttttctt tcagaagaaa agcattcttg tgggttgatt tctgattctt atcgacacat    720
tttgtcgaat aaaaaaagaa ttacgtggac taaggatctg catgaacatt ttgtcgagtg    780
tgttaatcgc cttggaggtt ctgagagtga gtaaattgat atgatcaata atttatatag    840
gatctagcta atgattttat gtacttactt attttaattt ttgatgatca ttgtttgtga    900
attgattaat cctagaggca acaccaaagg cgatactgaa actgatgaaa tcgaaagaat    960
tgagtatcct acaagtaaaa agtcatttgc aggtttctat taattaatta aacaactgct   1020
attgctgttt tttttttct ttttacttca tgaaatttta attgtgattt atctcaacat   1080
gagatctgat atttcttgtt ttatttctct cttgctgctt gtcagaaata tcgatccgag   1140
aagctcatat cagaccagtc tttacaaggt aattaatcaa ttcttgttta aaaaatatat   1200
ttctatttaa tttgaatatc tgttaattaa aaaaaaaaaa ttgcaggatt tcccgagaaa   1260
```

acagtttgta tcaatgatat acctcagctt tacatgaaaa tgtacgcaaa ctcttcttga 1320
ttaatttcct tctacattct tgatattgtt cataacaatt ccagaaatta tgtgcttaaa 1380
ttaattttat gcaggggcat gcaaataaga gaggcacttc aattgcagct agaactcgag 1440
aagcatcttc atgatcaatt agaggcatgt atttctatag aactttaatt tctattataa 1500
acttttaact ttttggtacg atattttttt tcaaaaaaga aaaaagagtt aaaatcgtct 1560
tactacttta aaaattgtaa aataatagtg tccaatttat tattatattt tacaaaataa 1620
tttactactt ttctgttaat gccataaatt gacctgtaaa atactaatac taaaaaaaat 1680
tgggttattt tgtggaacaa ttaacaatga ttatcatctt catgaaaatg attaatttga 1740
ttcacctcac gtttaattta ttactttctt gctacagatg caaatgaatt tacaaaagct 1800
gattgaggat caagggaagc aggtgaagat gatgttagag aagcaattaa aatcaaacca 1860
gaaataattt gagctttacg attataatta tgtcgacaga gatcatgtta gaaaaggatt 1920
aattgtagtt tattgacaac ataatcacaa gaaaaacaaa aatgattgta gtaataa 1977

<210> SEQ ID NO 25
<211> LENGTH: 693
<212> TYPE: DNA
<213> ORGANISM: Citrus sinensis

<400> SEQUENCE: 25
atggaagcac aatcacaaga aaagcaaaac ctggagcctg gtaaaatgcc atcaagcatc 60
atttctagtt atcatttaca agaactggct tctgcttttt atctaacaga tcaatgtttc 120
tttggatttc atcaaaatca acacaaaaat aatgaagtta tagaagcttc attaccacca 180
tcaaatcaat tttccgggga taatttttcc aagaagttgt ctgagctaga cactttggaa 240
tcattggtat tatcgagcaa ccgcaacagt aaatttccca gaaaaaatag cagctttccc 300
actccttctg agagcagcca aaatactaaa aaatatcgat ccgagaagct catatcagac 360
cagtctttac aaggatttcc cgagaaaaca gtttgtatca atgatatacc tcagctttac 420
atgaaaatgg gcatgcaaat aagagaggca cttcaattgc agctagaact cgagaagcat 480
cttcatgatc aattagagat gcaaatgaat ttacaaaagc tgattgagga tcaagggaag 540
caggtgaaga tgatgttaga gaagcaatta aaatcaaacc agaaataatt tgagctttac 600
gattataatt atgtcgacag agatcatgtt agaaaaggat taattgtagt ttattgacaa 660
cataatcaca agaaaaacaa aaatgattgt agt 693

<210> SEQ ID NO 26
<211> LENGTH: 1001
<212> TYPE: DNA
<213> ORGANISM: Citrus sinensis

<400> SEQUENCE: 26
aacataaacg aatttactct ctgataacac tttttaatat atattttcac ttacctgcag 60
ttgtagcgct atctgctgac tgctgctgct gctgctactc aaaatggctg aaaggatcca 120
ccccgaaacg acaccgcgca acgaacaaga gccctctcat ccgccggcgc ccgcggccgc 180
aggaacctac gtcatccaaa tcccgaagga tcaaatctac cgagttccgc cccccgagaa 240
cgccgaccgc atcaagggcc tctcccgccg ccgcaagtcc cgcagcacta cctgctgctg 300
cttccgtttc tgctgctgct cgctgcttct cctcgtcctc ctcttggcca tcgccgccgg 360
cgtcttctac ctcgtcttcc gtcccgaatc ccccaactac tccgtcgacg gcgtctccat 420
cgccggcctc aacctcacct cgccgtcctc cgtcgtctct ccccggttcg acgtctccgt 480

```
caccgccgac aatccgaacg acaagatcgg aatctactac gagagaggca gctcggtgga    540

ggtctcctac aaggacgtcg ccttatgcga cggcgaatgg cctcagtttt accagccgag    600

caacaatgtc acggttttca agacctcgct gaaaggatcg tccatcgagt tgaccagcgc    660

tatgcgcaaa gacctggttg ctgctcagac gagtggcaag acggtgccgt ttaaggtgaa    720

cttaagagtg ccggttaaaa taaaagtggg gtcggttaag acgtggacga ttaaggtaaa    780

agtgagatgt gatctgacgg tggataagct gacgtctcag tcgaagatcg tatctaagga    840

ctgtgattac tctgtcaaac tttggtaaaa aaagttaaaa aaatttcaaa tcaaaaggat    900

tcattgtaat tgtaggatta gattatacaa ttaattatta taatttgtgg tgtatttgtt    960

acaaatacac acttattatt atacttgtta ttagtctgtt t                       1001
```

<210> SEQ ID NO 27
<211> LENGTH: 1141
<212> TYPE: DNA
<213> ORGANISM: Citrus sinensis

<400> SEQUENCE: 27

```
gtcagacaca cacggccaaa gtttaggcat acgcgttagc gcgtacgcgg tttctttatc     60

aaaatatatg ctatgctgca tgcatatgat ataataacat aaacgaattt actctctgat    120

aacacttttt aatatatatt ttcacttacc tgcagttgta gcgctatctg ctgactgctg    180

ctgctgctgc tactcaaaat ggctgaaagg atccaccccg aaacgacacc gcgcaacgaa    240

caagagccct ctcatccgcc ggcgcccgcg gccgcaggaa cctacgtcat ccaaatcccg    300

aaggatcaaa tctaccgagt tccgcccccc gagaacgccg accgcatcaa gggcctctcc    360

cgccgccgca agtcccgcag cactacctgc tgctgcttcc gtttctgctg ctgctcgctg    420

cttctcctcg tcctcctctt ggccatcgcc gccggcgtct tctacctcgt cttccgtccc    480

gaatccccca actactccgt cgacggcgtc tccatcgccg gcctcaacct cacctcgccg    540

tcctccgtcg tctctccccg gttcgacgtc tccgtcaccg ccgacaatcc gaacgacaag    600

atcggaatct actacgagag aggcagctcg gtggaggtct cctacaagga cgtcgcctta    660

tgcgacggcg aatggcctca gttttaccag ccgagcaaca atgtcacggt tttcaagacc    720

tcgctgaaag gatcgtccat cgagttgacc agcgctatgc gcaaagacct ggttgctgct    780

cagacgagtg gcaagacggt gccgtttaag gtgaacttaa gagtgccggt taaaataaaa    840

gtggggtcgg ttaagacgtg gacgattaag gtaaaagtga gatgtgatct gacggtggat    900

aagctgacgt ctcagtcgaa gatcgtatct aaggactgtg attactctgt caaactttgg    960

taaaaaaagt taaaaaaatt tcaaatcaaa aggattcatt gtaattgtag gattagatta   1020

tacaattaat tattataatt tgtggtgtat ttgttacaaa tacacactta ttattatact   1080

tgttattagt ctgttttgta aaattcttgt gtggaaacaa gatatacaat taattaatta   1140

a                                                                   1141
```

<210> SEQ ID NO 28
<211> LENGTH: 1380
<212> TYPE: DNA
<213> ORGANISM: Citrus sinensis

<400> SEQUENCE: 28

```
caaggttttc aaaggagagt gacctttaaa aaaaaatgtc accgacacac aagaaaaaaa     60

taattaaaat aaataaataa aaaaatgtct aagtccccta tataataagt gcatgtgaag    120
```

-continued

```
ctgagcgatg ccattcaata agtagccctc gcagaacaaa aaatgatttt cctactactc    180
ctctcagttt ttcttcgcgg agcttcttca tcaatccttt ccgaagacac acctattagc    240
ttctcatttc cctcattcgc caaagacagt tgtgacaata agaccctcat ttgctacgga    300
gcgattgaaa gttccggcgc cttaagcatc acaccaggcc ctccaccaaa cctgccgatc    360
agaaaggttg gacgggtttt atacggcaag cctctgagtt tacagcgatc ttttattgat    420
accaccatca ccattaagat ctcacgccat cagaattaca ctgatcgtgc cggagatggc    480
atgacgttca tttttgcaag cgataaaaac ggtccatcag caaagggcgt cggcgaatat    540
cttggactgc agtcttcacc aggtatgatt atcaatgtga agaattaaga atttatgcag    600
ataccattga aagtactgac aaatgcatgc atgggcgcat tttatttata atggcagtca    660
aatgataaac aatatgatga tatatcatat gttctatata taacacttat acatatatat    720
tcatgatcat gcatgtaaat tatgcaggcg ataaatttcc tccattagcc gtggagctgg    780
acacatgcct gaacaagaac ctgaatgatc cagatgataa ccatattggc atcgacataa    840
acggaatcga atcaaatcca gttaatagtc tgcttgacgt tgatctcaaa agtggacgag    900
caatccaggt tcgaatttat tacaatccag actttggaca actctctatt tatgcggcat    960
attcggggga aacacttgtg aaggtgattg aaaaacccat taacctgtca gatataattc   1020
caacgcccgt ctatgttgga ttcacagcag ctacggggga ctttttagaa agccatgagg   1080
ttataaattg gaccttcaac tcgttcccag tgccgccttc tctcaaggag aaaaacctgg   1140
tgatgccaat ataattctaa accgtccttg aaaaaccatg tcacataaat tataatcaat   1200
aataattaat atcaccaata aagtgacatg gctcttgcat taaaatattg aataaaatga   1260
tagcagcgac taggattaat actgtttgct tgctgtctga gatgtactgt atgtgcttat   1320
gtagaaatgc tcatattcag cttctattga ttacgttgca gctttgagct tctgatgttt   1380
```

<210> SEQ ID NO 29
<211> LENGTH: 1512
<212> TYPE: DNA
<213> ORGANISM: Citrus sinensis

<400> SEQUENCE: 29

```
acacaaggtt ttcaaaggag agtgaccttt aaaaaaaaat gtcaccgaca cacaagaaaa     60
aaataattaa aataaataaa taaaaaaatg tctaagtccc ctatataata agtgcatgtg    120
aagctgagcg atgccattca ataagtagcc ctcgcagaac aaaaaatgat tttcctacta    180
ctcctctcag tttttcttcg cggagcttct tcatcaatcc tttccgaaga cacacctatt    240
agcttctcat ttccctcatt cgccaaagac agttgtgaca ataagaccct catttgctac    300
ggagcgattg aaagttccgg cgccttaagc atcacaccag gccctccacc aaacctgccg    360
atcagaaagg ttggacgggt tttatacggc aagcctctga gtttacagcg atcttttatt    420
gataccacca tcaccattaa gatctcacgc catcagaatt acactgatcg tgccggagat    480
ggcatgacgt tcatttttgc aagcgataaa aacggtccat cagcaaaggg cgtcggcgaa    540
tatcttggac tgcagtcttc accaggcgat aaatttcctc cattagccgt ggagctggac    600
acatgcctga acaagaacct gaatgatcca gatgataacc atattggcat cgacataaac    660
ggaatcgaat caaatccagt taatagtctg cttgacgttg atctcaaaag tggacgagca    720
atccaggttc gaatttatta caatccagac tttggacaac tctctattta tgcggcatat    780
tcgggggaaa cacttgtgaa ggtgattgaa aaacccatta acctgtcaga tataattcca    840
acgcccgtct atgttggatt cacagcagct acgggggact tttagaaag ccatgaggtt    900
```

ataaattgga ccttcaactc gttcccagtg ccgccttctc tcaaggagaa aaacctggtg 960
atgccaatat aattctaaac cgtccttgaa aaaccatgtc acataaatta taatcaataa 1020
taattaatat caccaataaa gtgacatggc tcttgcatta aaatattgaa taaaatgata 1080
gcagcgacta ggattaatac tgtttgcttg ctgtctgaga tgtactgtat gtgcttatgt 1140
agaaatgctc atattcagct tctattgatt acgttgcagc tttgagcttc tgatgttttc 1200 ttacccttt cctcgttctc ttctttaagt ttatcggaac aaaattctct tctcacggtg 1260
gatatcatag cataaaattt aaccatagga aacaatgcat gcatcgctat agatattaat 1320
tacatgtgga gtccttttct cctgcgaacg tctgtacgaa tttttgtgcg atggaactca 1380
gatttttaga acgtcgtaca tttgcctcta gatgtatatg acaatataaa ctctattaga 1440
aatctgaatt catacattta ttgcgtagtc catagttcta tcgataataa atatgaaata 1500
tgtgaaaaga at 1512

<210> SEQ ID NO 30
<211> LENGTH: 7810
<212> TYPE: DNA
<213> ORGANISM: Citrus sinensis

<400> SEQUENCE: 30
atggagaaat taattaagca aatcatgaat caaatacgag aagaatcgaa agaaattcaa 60
gaaccgttcc aacaatcacc tccactggta agtgattcta ttttttcact tttactccct 120
ccttcctttt acctcatata atttcaggta aacgctaatt tggtccatat aatttaagag 180
aattattccc tataaatttt gtcttattag ataaactctt acaatcagaa cactaggcca 240
agaagacaaa ggcttcagcg aaatggacaa atatggccag gtcaattctt ttttgttttt 300
tttttggctt ctttttttcac aattaatacg gtacagcagt cagagtcatg tgatgagatc 360
ttgcatttta catcttttgc tttaagcaca tggaatggaa ttgttggtat atgaatttta 420
gaattttctg ctgtaccgta catccgcctt ggccgtacag cagaaggtga gtacaaaatt 480
ccaatccatt gattatatat atactataat ttatggatgc catttaatta attcacgtag 540
gaaacagaag atttgaggct gaagattgat gaattggcag aggaagtaaa gaatggagaa 600
attaattaag caaatcatga atcaaatacg agaagaatcg aaagaaattc aagaaccgtt 660
ccaacaatca cctccactgg taagtgattc tattttttca cttttactcc ctccttcctt 720
ttacctcata taatttcagg taaacgctaa tttggtccat ataatttaag agaattattc 780
cctataaatt ttgtcttatt agataaactc ttacaatcag aacactaggc caagaagaca 840
aaggcttcag cgaaatggac aaatatggcc aggtcaattc ttttttgttt ttttttggc 900 ttcttttttc acaattaatg ctttcttttt ctcgttgttt tagctgtttt agttgattaa 960
gttgtattca ttatttattt tatagttttt cttttccttt agtgagtcgg ccgacagctt 1020
atttactcgg ttgagctttt aataaataaa ttttatttct ttttgttaaa aaaattgccc 1080 caaccccccca agggtttcac caagtagttt ttttaattga tcaccagaac ttaaattttg 1140
agcaggttgg agggctaaaa aaaaaaatta atttaaactt ttaaaattaa tttatttgta 1200
aattaatttg tgaggtgtac tcagaaatca gggttttcag aaaattttta ggggtgccag 1260
tagcaccaat cttaattttt agagtttttc tctgacgaag atatcgaaag agtttataag 1320
cagactaaaa tatatacctg atttagcttg aaaactttga attaaactca ctagcgagaa 1380
aattctaaat taactattta agatccgata cttatgaaga cagtaattaa ccaaacatgt 1440

-continued

```
cttggccttt ctatttttta tatccttttt gtttaatcag tttttctcac tctcctttct   1500
ggtttatagg ttatgaggtg atcggtgagg taaggaacaa atgttgactg aaaagtctat   1560
caaatttttg tttctctctc tctctctctc tattttcttc ttctaagaca ctgtcttata   1620
accagaaaac taatctagga cgacaaaggc ttcaacgaaa ggaaaaaatt tggccaggtc   1680
aagatacata ttttgtgttc tttgttttcc cgttaatcac aatattttta ttctaaattc   1740
gaattttgta aaatctggat gttcaaacct gacaacaata tatatatata tattatttat   1800
ttctttttat taaaataaaa atactcttat aaatagaaaa agaactccaa tgtattgaaa   1860
atttttattt tttatatttc agtacattgg agtttcgcat ttttttaaat tttcaaattg   1920
gagactaagg tggcgtttgt tttttaactt aataacttaa agtgacttaa cttaattaat   1980
taagttaatt agaggtgttt gtttttataa cttaatgaga ctttttagat aactttgact   2040
taataaaata agttaatttt tttgactttt tacttaatgg agaaatctga attaagtcaa   2100
ttacttgcta atgtcaaaaa tatccctatt ttataattta tttttcatgt atatcccaaa   2160
actcacccat agatatttac cccacataaa aatatccctg ttttttcttt cttatattat   2220
atacgataaa atttgaaatt tatggtattt tatatattaa attctaaaat aattatgtat   2280
tcacttgaat atagttttac ttataaatat taaaatattg tggtatttaa tatattattt   2340
atttgacatt caaatttaat aaggatataa atgtaaaagt acatattttc aactttttaa   2400
gttgaaaaaa ataaacaact taatacttat tttccgagat tcagacgaaa aaataaatat   2460
attatttaga ttcagacatt cagacctatt cagaatttag acctattcag gtttattcag   2520
atttcagaca aaaaaacaaa cgtcacctaa gtctggagat agtctttttt attttcgcat   2580
ttttttataa aataaaaaaa ttttattttt tgttcatctt ttttcacatt ttttttataa   2640
acaaatattt accctttttc atttgtcctc ctatattttc attcttttat gtttaattta   2700
tccttttttc tccttttttgg tttctaggat ctgaagaggt aattggtgac ggttgtcatg   2760
tttcgattcg tacggaaact aggaaaaaac ttaaagatgt agggatttgt gctcttcata   2820
attcaaaata taatttctcc taaaaaaaga aaaaatttct ctttataatt cataatataa   2880
atttattttt tctaataata taccagattc gcggaaacaa tccataccca ggatccatgg   2940
tcaaggataa agcaaaagaa attgttgatg acaataaggt cagtacaaaa ttatttgcaa   3000
acatcaatcc aaaacaaaat tcattactgt cttatatgtg ttatttttatt attataggaa   3060
acagttgcta attcaattag tgaaggcttt gaagtgattg gcgacgaggt agatccagga   3120
ttaaatttat ttttatttta aattattagg taggaaaaag aacacttaca tccctaaggt   3180
cggagaaata attaaataga ccccaaattt tctaatccca agatattttt tttatatcat   3240
aatatctttt tatttttgtt aactcaaaaa atattgacaa aataaaaata taattttaaa   3300
ataaatgtaa taataaatac attttaaaat aactttaata ttaaaaaata ttttaatact   3360
taacaatcta ttagacattt tttattatat caaaataaaa ttttatacta aatagaaaca   3420
taatgtttaa acaaatatat taaaatctaa attattttaa atattatgta aaataataat   3480
tgggatattt taatttttcc actagaagtt ttttaatata tcacgttatt atcaagattt   3540
cttgaaagtt gcattttact acctaatgtt taggctatta tcctttaacc accaaaatgt   3600
taatatagtt aaaaatttac tgatgtcata agggctttaa agaaattttc attaaaacca   3660
atatgcatcg ttctcaatta tgaaataaac tgctaaataa taaaaaaatt aaaaaattcc   3720
taacccgaaa tgaaaattaa atggaaattt gaagaaattg agagtgaaga gaggaagaaa   3780
ggcaaatgct cttgagaatt tgaagaaggg agttcttagt tgagaatctg aagatgaagg   3840
```

```
agaaatggaa aagcagaaga aacgaagaag aagacaaaaa gggggaaaaa agttaaggaa   3900
aaaaaaaaga agaataaacg aagagggaaa gaaaaagaaa aggaaaaatg agagacattt   3960
gaagatgaag aagaaacaga gaagccggag aaatgaagaa gaagagaaaa aagggggaaa   4020
aaaaaaatca gaaacacatt aaagccctac ccgcctcagc tgccgcaacc atccatcttc   4080
ttttcctcga tcatcaccac tagaaaacac tggccatcat aacccagcaa tcaacaccat   4140
gaaccgccgc cttaatgacc ataaatacca tcaaacagct acgcagccaa acaacacaac   4200
tcgggtttgt tatttctttt ttttttcaaa ggacaagatt gtcttttgta ctctagggac   4260
aaaattgaat tttaacttat attctgttaa atatttactt attttttaat ggaatagtgg   4320
tacagtaata accgcataaa tattaagtgg taaaatgcag ttttcacgaa tccttaatgt   4380
taacttttgg tagaaaaatg ataatgtccc taataattta agcaccatta gtaagtaaga   4440
tattttacta attgtaaaat atatttaatc taaagattta tataaaatgt ctgtaataaa   4500
tacaaatata tttttcaata aatataatac ttttatatat tcaaaattat tttagatact   4560
acaaatattt taatattatt cgtcaactat attcaaagag tattatggta aaaaaatatc   4620
ttagtgttct tttctaaaaa cgtgagcatc tacatgtcta tttccaaaaa cttggatata   4680
actatccatt tctcctatta ggtcctaaaa aatataattt tgatagttaa atatgctagg   4740
ttacattgta atataccta catcaattgc aaaaggatct gattagctcc aagctcatgt   4800
catttttttt attcttttaa actcttttgt tcttagacaa gctctatcaa ccaagaaatt   4860
aggccacgac gacaaaggct tcagcgaaac ggaaacattt ggccaggtca attcgttttt   4920
tttccctttt attatttcct ttcttttttg ttttcccttt tctaattaat catatctttt   4980
cccattctta gtttcatttt attacggtct aacatttgaa tttatttttt gtgtgtgtgt   5040
atgtatgtgt gtgtatatag agttctgcca tcattttact ttaatgcaga cttaattaag   5100
tagtaactaa gtgtttttta atagtgataa aaaaatcaca aactctcatg tatatttatt   5160
taatggatta tgatgacaaa tgctactttg agtgaaaaaa agtgactgag aattttagtg   5220
agtttagaaa gagaccaaac tacctttact gattcttttg ttattattat tatttttaaa   5280
aggtaagggt ggataaagat aaaatttatt tttaatctat acttctttta aaatttaaac   5340
tcatgtagtc agttaaagaa tattaattaa aaaccattta aaaaaatacc attaatgatt   5400
tcaacttcta attaaagtaa ttaataatta aattctgagt tagctgttta tgaatggaga   5460
cgtgcatgaa ggctgtaatc aaccaaaatt tgtcttggtc ctcctgtttt tactcatgca   5520
gtctcctttt cggtttctag gctctgaggt gattgttgac gatgttcaag attcggttcc   5580
tgtggattct gggaccaaca atgtagggac gtgacctctt ttccatacga cattatatgc   5640
atacgtgtca tttttcactt tttcggcact gggatttatt taattttttc gattatttta   5700
tttctgatta gacaccgaaa aaaaaaaata caatcatttt gccagttaaa taaaattgga   5760
aaagaaacaa atattaactc caaaatctgt cttttttttt tttctttttg tctttttgtt   5820
ttaatctttt tttttttttt tctattttct tcttcttaga tgagctctta cggccagaaa   5880
actaagccag gacggcaaag gcttaagcga aaagaataca tttggccagg tcaatatata   5940
tatttttctt tcataactaa tctcatgttt tctcagtatg caggtttatt ttttaattta   6000
ttttaatcct tagttaaaca taatgtcagc accttcacta gaaaatataa taaaaatatc   6060
catatatgta agaatgaaaa attaaatcac gaactaatat gtatgctgat ttaattcaga   6120
gtgatgctac ttgacggaac aaaaagtagg aaaaaaatct aacttcgatt ttgaaagagt   6180
```

ttgtataata ccgtgcttaa tttgggtaac tttttttttt tttttttggg tgaggatcac 6240
tgtatttcac ctcatttccc ccactaaggc tcgaacttag tacttggccc taagaagaca 6300
atgctcttac tatatgaact aagtcttcgc atccacttaa tttggatact taggtaggat 6360
atctactgat gtgtcaccaa ttatttaata ttatgtatat ggtattaatt aattttatta 6420
tcaattatta acctactact tttaaaattt ctcaataaat gatatataag atgctatatc 6480
agtaagtatc tcaattgagt atccaaagtg aataagcaca atattactgc tttaatttat 6540
atatcttgat ctttaatttt ttctttcttt tctgtttaac ccatttttct tattctcctt 6600
tttggtttct aggttctgag gtgattggtg agagtggttc gattcttact tatcaaaaga 6660
aaaaactcga agatgtacga atttgagctc tttctattat tgatattaga tacatgtcat 6720
ttacaaattt ttaccactat gattaaatct atttttgatt ttcagattgg ttagtagtaa 6780
taaatatccc aaaattttat ccaaaaataa ttgggcatgt gatgtatgat tcatcaaaat 6840
agttgataaa tcttataggt cccaagtaaa ttagttataa tatttcacta tccaaacaaa 6900
tactacatca tttaggatca aagtttggga taggaaaaaa aaatattttg cttgaaaatt 6960
atttttgatt ttgtccagtc gggtataatt ttcggacact gttgtagtgc tctttgtgat 7020
gtattttgag ataaattcag tacattgtct tacatttgtg cagctacctg caaagtgcat 7080
ttcgcgcatc atttctctta cgacacctcg cgatgcaagt aggttggcac tggtatgtcc 7140
cgccttcaga tcggctgcgg attcagattc cgtatgggag aagtttttgc cgtccgatta 7200
cgaagggttc atttcgaact catctttgat cgacaggaag aagaaggatc tttattttca 7260
tctatgtcgc aaccccatcc tcttcgacaa taataccgcg agctttgggc tagagcaaga 7320
gagtggtaaa aaatgttaca tggctggtgc aaaatggatt tatgaaaatt cgggaatttc 7380
acaccgagat tgcgaaatga ttccttcatc agctggatct aggtttcctg aagtgattga 7440
acttaagctt atgtcgagtt tagaaatcga agcaagattt ggtacaacaa ttttttcacc 7500
caaaaccaat tatgcagctt actttgtgtt caagtttgcg gaattcagag aagggcctga 7560
aactagtcct atagattttg aagtctattt tgagggaagc cataatggca aaaagcgtag 7620
agagtttctt gatcctcaac tatctcaaga ccgaggaaat aggtggatag agattaagat 7680
gggtgagttc tctattgaaa atggagatga aggaacagta gtttgtaggc tgtccgaacc 7740
agaaccctta tctaagcgtg gcactattat tttccaaggt attgaggtta ggcctgaata 7800
tggcaggtaa 7810

<210> SEQ ID NO 31
<211> LENGTH: 1434
<212> TYPE: DNA
<213> ORGANISM: Citrus sinensis

<400> SEQUENCE: 31
atggagaaat taattaagca aatcatgaat caaatacgag aagaatcgaa agaaattcaa 60
gaaccgttcc aacaatcacc tccactgaac actaggccaa gaagacaaag gcttcagcga 120
aatggacaaa tatggccagg ttatgaggtg atcggtgaga cactgtctta taaccagaaa 180
actaatctag gacgacaaag gcttcaacga aaggaaaaaa tttggccagg atctgaagag 240
gtaattggtg acggttgtca tgtttcgatt cgtacggaaa ctaggaaaaa acttaaagat 300
attcgcggaa acaatccata cccaggatcc atggtcaagg ataaagcaaa agaaattgtt 360
gatgacaata aggaaacagt tgctaattca attagtgaag gctttgaagt gattggcgac 420
gagacaagct ctatcaacca agaaattagg ccacgacgac aaaggcttca gcgaaacgga 480
aacatttggc caggctctga ggtgattgtt gacgatgttc aagattcggt tcctgtggat 540
tctgggacca acaatatgag ctcttacggc cagaaaacta agccaggacg gcaaaggctt 600
aagcgaaaag aatacatttg gccaggttct gaggtgattg gtgagagtgg ttcgattctt 660
acttatcaaa agaaaaaact cgaagatcta cctgcaaagt gcatttcgcg catcatttct 720
cttacgacac ctcgcgatgc aagtaggttg gcactggtat gtcccgcctt cagatcggct 780
gcggattcag attccgtatg ggagaagttt ttgccgtccg attacgaagg gttcatttcg 840
aactcatctt tgatcgacag gaagaagaag gatctttatt ttcatctatg tcgcaacccc 900
atcctcttcg acaataatac cgcgagcttt gggctagagc aagagagtgg taaaaaatgt 960
tacatggctg gtgcaaaatg gatttatgaa aattcgggaa tttcacaccg agattgcgaa 1020
atgattcctt catcagctgg atctaggttt cctgaagtga ttgaacttaa gcttatgtcg 1080
agtttagaaa tcgaagcaag atttggtaca acaatttttt cacccaaaac caattatgca 1140
gcttactttg tgttcaagtt tgcggaattc agagaagggc ctgaaactag tcctatagat 1200
tttgaagtct attttgaggg aagccataat ggcaaaaagc gtagagagtt tcttgatcct 1260
caactatctc aagaccgagg aaataggtgg atagagatta agatgggtga gttctctatt 1320
gaaaatggag atgaaggaac agtagtttgt aggctgtccg aaccagaacc cttatctaag 1380
cgtggcacta ttattttcca aggtattgag gttaggcctg aatatggcag gtaa 1434

<210> SEQ ID NO 32
<211> LENGTH: 393
<212> TYPE: DNA
<213> ORGANISM: Citrus sinensis

<400> SEQUENCE: 32
atggctgaaa ggatccaccc cgaaacgaca cagcgcaacg aacaagagcc ctcacatccg 60
ccggcgcccg cggccgcaag aacctacgtc atccaaatcc cgaaggatca aatctaccga 120
gttatgcccc cgatgaacgc cgaccgcatc aagggcctct cccgccgccg caaatcccgt 180
agcactacct gctgctgctt ctgtttctgc tgctgctcgc tgcttctcct cgtcctcctc 240
ttggccatcg ccgccgacgt cttctacctc gtcttccgtc ccgaagcccc caactactcc 300
gtcgacgaca agatcggcat ctactacgag agaggcagct cgatggaggt ctactacaag 360
gacgtcggct tatgcgacgg cgtctggcct tag 393

<210> SEQ ID NO 33
<211> LENGTH: 393
<212> TYPE: DNA
<213> ORGANISM: Citrus sinensis

<400> SEQUENCE: 33
atggctgaaa ggatccaccc cgaaacgaca cagcgcaacg aacaagagcc ctcacatccg 60
ccggcgcccg cggccgcaag aacctacgtc atccaaatcc cgaaggatca aatctaccga 120
gttatgcccc cgatgaacgc cgaccgcatc aagggcctct cccgccgccg caaatcccgt 180
agcactacct gctgctgctt ctgtttctgc tgctgctcgc tgcttctcct cgtcctcctc 240
ttggccatcg ccgccgacgt cttctacctc gtcttccgtc ccgaagcccc caactactcc 300
gtcgacgaca agatcggcat ctactacgag agaggcagct cgatggaggt ctactacaag 360
gacgtcggct tatgcgacgg cgtctggcct tag 393

<210> SEQ ID NO 34

<211> LENGTH: 2434
<212> TYPE: DNA
<213> ORGANISM: Citrus sinensis

<400> SEQUENCE: 34
tggtctttgg ttttgtcaat tagatcaatg ttcatttttc caatatatat atatacatac 60
acacacacat gaagtcttac ccccgaagat ttatggaata taagagagaa ttttaaccca 120
taagtttgaa ttcaacgaca tgtctgttca ttatttatcc attcaatctg catcttcctc 180
ttttcagatt ttccgtgttt gttgcgcggt tccttctctt ttaacaaatt agggctcgaa 240
taattttgat tctaccattt aaaaactgaa tgcatagcag gctagcaaga agttcttgtt 300
cataaatttt tgcagtacct tccggaaatg aatactcaaa agcttaattt tcaggaaaca 360
tttcaaaaaa agcatttgga tttcgggcca ccatcccaat atttcggcga tatccaccac 420
cagcagccct ggatgatgag aacaaccacc cagcagcatc aaaatcttga tcatgctcga 480
tctccgagca caatcttgag ccggtttgag tctccagctt cagcttttta cgcaactgaa 540
agatacatgg ggttttgtca gtatgattcc caagctgctg gtaacaactg ctcacaattt 600
tccaggactt gtgattcttc acaacagttt catttgtatc agtcccctgg agaaaatttt 660
tctgttttat cagctgaaca agctgtccct ctagaaattc cctggaactt ttacaaatcc 720
cctgaagctt cgtgtatcaa tccccttgga aaacaatatt caggtccatt tgatgaacat 780
caagatcata gagtaagtag tttccctccc tggagacttt tcattcattt tttttctttt 840
ttttcattca gaatttgttt ttgattgtgg gtagtttttg tttttttttt ctaccttcag 900
gtctctaatg atggttatgg attaacttca ctttcacaac agggctacgc ttcacatcaa 960
gagaagcaat ctccaagatt ttcttctagt agttcttttt caactggacc tgtgatcacg 1020
aacaaaactc gaattagatg gactcaggat cttcatgaaa aatttgtcga atgtgtgaat 1080
cgactagggg gagcagacag taagtgttga tatttattga attttgtcag ttgaaggagc 1140
aaaatttttt aattatttgt ttttccactt tttttttttt ttttgaattg gttgattaat 1200
tgcagaggcg acgccgaagg caatattgaa gctgatggat tctgaaggat tgacaatttt 1260
tcatgtgaaa agtcatttgc agaaatatcg aatggccaag tacgtcccag aatttcctga 1320
aggtatatta aatctgcact ggttttgttg aaattgattt tttttctttt ttagggtcaa 1380
aattctgata ggaactctgt ttctttttgc aggaaaatta gagaaaagaa gtagcttgaa 1440
tgatttgcct caaatcgatg tcaaagcgta aattcattat attttggaat tttacagaaa 1500
taattgttta gaagtccttc taacaactcg taacttccgt ctatggcagc actctgcaaa 1560
tcaaagaggc attacaactt caattagatg tccaaaggcg actgcatgaa caactagagg 1620
tacattccag aagttttgtt taatataatt tctatgaaaa tcctcaatgc caaacattcc 1680
cttaatagcc atggtccaaa aatgtaatct ttgtttcctc catgcaattc aatgttattc 1740
ttgaatggca gagtaaattt gattgatatt ctttttgggg tcagattcag agaaaattac 1800
agttgagaat tgaagagcaa gggaagcatc tcaagatgtt gtttgatcaa caacaaaaag 1860
caagtaagga tcactcgaag cctcaaaatt tggaaaaagt accagaagat gacccccat 1920 ttaattttga agggatcgaa ttttcaactt cagagaattc gggaaactcc catttcacgt 1980
aaaagataag ttagtttcat ttaactgaag ctgaaatcgt ttgaaaattt tatacgagaa 2040
gacttggggt tgaagcaaag attattacag ttcgtgccaa tgaatcaaaa atagctgctt 2100
actgttacag agtgaagtat ttacattatg attctacaca cagaagaagt gattacaaag 2160
aagaagtaaa taattacaaa gaagaagtaa atatatattt tacttgttaa taaatcatac 2220

-continued aatggtttgt gtataaaatt tagatctaca ttattgaatc tagtacggat taattcaagc 2280
tccatcatct tgtaacagat acagtgcgac agttttgatt tttgctgctt ggtctgtgta 2340
aagtaggttt caaattttga tttcatgttt tcatcagacg atgagtaggt ggagaaacag 2400
agttgaatac catgatcatt gtatcttctc ttaa 2434

<210> SEQ ID NO 35
<211> LENGTH: 1445
<212> TYPE: DNA
<213> ORGANISM: Citrus sinensis

<400> SEQUENCE: 35
atgaatactc aaaagcttaa ttttcaggaa acatttcaaa aaaagcattt ggatttcggg 60
ccaccatccc aatatttcgg cgatatccac caccagcagc cctggatgat gagaacaacc 120
acccagcagc atcaaaatct tgatcatgct cgatctccga gcacaatctt gagccggttt 180
gagtctccag cttcagcttt ttacgcaact gaaagataca tggggttttg tcagtatgat 240
tcccaagctg ctggtaacaa ctgctcacaa ttttccagga cttgtgattc ttcacaacag 300
tttcatttgt atcagtcccc tggagaaaat ttttctgttt tatcagctga acaagctgtc 360
cctctagaaa ttccctggaa cttttacaaa tcccctgaag cttcgtgtat caatcccctt 420
ggaaaacaat attcaggtcc atttgatgaa catcaagatc atagagtctc taatgatggt 480
tatggattaa cttcactttc acaacagggc tacgcttcac atcaagagaa gcaatctcca 540
agattttctt ctagtagttc tttttcaact ggacctgtga tcacgaacaa aactcgaatt 600
agatggactc aggatcttca tgaaaaattt gtcgaatgtg tgaatcgact agggggagca 660
gacaaggcga cgccgaaggc aatattgaag ctgatggatt ctgaaggatt gacaattttt 720
catgtgaaaa gtcatttgca gaaatatcga atggccaagt acgtcccaga atttcctgaa 780
ggaaaattag agaaaagaag tagcttgaat gatttgcctc aaatcgatca ctctgcaaat 840
caaagaggca ttacaacttc aattagatgt ccaaaggcga ctgcatgaac aactagagat 900
tcagagaaaa ttacagttga gaattgaaga gcaagggaag catctcaaga tgttgtttga 960
tcaacaacaa aaagcaagta aggatcactc gaagcctcaa aatttggaaa aagtaccaga 1020
agatgacccc ccatttaatt ttgaagggat cgaattttca acttcagaga attcgggaaa 1080
ctcccatttc acgtaaaaga taagttagtt tcatttaact gaagctgaaa tcgtttgaaa 1140
attttatacg agaagacttg gggttgaagc aaagattatt acagttcgtg ccaatgaatc 1200
aaaaatagct gcttactgtt acagagtgaa gtatttacat tatgattcta cacacagaag 1260
aagtgattac aaagaagaag taaataatta caaagaagaa gtaaatatat attttacttg 1320
ttaataaatc atacaatggt ttgtgtataa aatttagatc tacattattg aatctagtac 1380
ggattaattc aagctccatc atcttgtaac agatacagtg cgacagtttt gatttttgct 1440
gcttg 1445

<210> SEQ ID NO 36
<211> LENGTH: 1309
<212> TYPE: DNA
<213> ORGANISM: Citrus sinensis

<400> SEQUENCE: 36
atgaatactc aaaagcttaa ttttcaggaa acatttcaaa aaaagcattt ggatttcggg 60
ccaccatccc aatatttcgg cgatatccac caccagcagc cctggatgat gagaacaacc 120

```
acccagcagc atcaaaatct tgatcatgct cgatctccga gcacaatctt gagccggttt    180

gagtctccag cttcagcttt ttacgcaact gaaagataca tggggttttg tcagtatgat    240

tcccaagctg ctggtaacaa ctgctcacaa ttttccagga cttgtgattc ttcacaacag    300

tttcatttgt atcagtcccc tggagaaaat ttttctgttt tatcagctga acaagctgtc    360

cctctagaaa ttccctggaa cttttacaaa tcccctgaag cttcgtgtat caatcccctt    420

ggaaaacaat attcaggtcc atttgatgaa catcaagatc atagagtctc taatgatggt    480

tatggattaa cttcactttc acaacagggc tacgcttcac atcaagagaa gcaatctcca    540

agatttctt ctagtagttc tttttcaact ggacctgtga tcacgaacaa aactcgaatt    600

agatggactc aggatcttca tgaaaaattt gtcgaatgtg tgaatcgact agggggagca    660

gacaaggcga cgccgaaggc aatattgaag ctgatggatt ctgaaggatt gacaattttt    720

catgtgaaaa gtcatttgca gaaatatcga atggccaagt acgtcccaga atttcctgaa    780

ggaaaattag agaaaagaag tagcttgaat gatttgcctc aaatcgatgt caaagccact    840

ctgcaaatca aagaggcatt acaacttcaa ttagatgtcc aaaggcgact gcatgaacaa    900

ctagagattc agagaaaatt acagttgaga attgaagagc aagggaagca tctcaagatg    960

ttgtttgatc aacaacaaaa agcaagtaag gatcactcga agcctcaaaa tttggaaaaa   1020

gtaccagaag atgacccccc atttaatttt gaagggatcg aattttcaac ttcagagaat   1080

tcgggaaact cccatttcac gtaaaagata agttagtttc atttaactga agctgaaatc   1140

gtttgaaaat tttatacgag aagacttggg gttgaagcaa agattattac agttcgtgcc   1200

aatgaatcaa aaatagctgc ttactgttac agagtgaagt atttacatta tgattctaca   1260

cacagaagaa gtgattacaa agaagaagta aataattaca aagaagaag               1309
```

<210> SEQ ID NO 37
<211> LENGTH: 4122
<212> TYPE: DNA
<213> ORGANISM: Citrus sinensis

<400> SEQUENCE: 37

```
tgaagtgtca atacttatat agttcccttt tacaggaaaa agaaatgaac atataagtaa     60

cgctagataa taaaggggaa gtgggaagag ggaatgggga actggttcag gaaaagagag    120

gattctgttc cttcaattaa atagaataag gagtccctta agcttgcaaa ttggccacca    180

aaaacccctg aaatgcaccc cccgttaata ttgaattaaa cgaaacatgc atgcttcgat    240

gagtcgatct caaactcaat ggtgccccga cattcatact ttaagctggt aaagagcatc    300

aaaatttcgg gaaaatgatg ctcattctag ctagttgctc atgcgcgtgg cgtaattaag    360

ccagaccaat ttgtagatcc tgctattgag tgctagctga tgatggcaga acttattccc    420

atataaataa ccaccaatgg caataattta tacatacagg aggtttacaa tttctggaag    480

tgataccaag cttttgattt tgaatcccat aagcatgaaa gcgataccta acggttaaaa    540

tttttgacaa agaaataacc ccatgcataa taagaaaata ggtttaatct gtgcaactaa    600

tatacatcac agtattcatc caacaataag actagtattt ttagctgctt aatatgcaaa    660

aattattgac taataatagt aagtaattgt tttgacctgc taacgtagga atttgatcgg    720

tcagcgggaa agtatcaatc taatcgcttg aggccaaatt accctttcga tacatatagc    780

ataggtgaag gcatatgtaa tatgctgtcc cttcaaactt ctaagggtca tttttagata    840

gtgtccacct aaatggaacc aaaagaaaaa cctttgttta ttagtggatc tcatgcttac    900

cctgatgcaa agagtcgtct tcatcatcac gcaagaattg tttgtttatt atcggtgtcc    960
```

```
ctcacaattg ataaagttat taaacaattt gcttgagcca ttttggaagt atcgagtact   1020
cccttgttta attagatcat gttcaatttg ccgcgtacag aatgatgatc gtaaaataca   1080
atgcttaacc tatgcattct gattaattta taatgggatt cacaatgtat gcgtaacacc   1140
gttataacta agccaacttt cccagatact actgataatg acaagaactt tcctaaaatg   1200
taaaacaacc atgaagcgtg taggatagaa aatgacttgt aacctaccaa gtgtttaaga   1260
tcagtgatga tttgatgagc aacaaagtca agatttatct tagtaaatgg ctcgttgtaa   1320
tgtatgatta tttttggaag tgatgaatga tcagttaatt atatgctgta agtgactaag   1380
taagtttgga acttcgggtg tatcaaacgc aaacaagatt aatgttacct ttctctctga   1440
cttggactga ttaaataaga tcaagcattg atgtcgacac cttatgctga agctttacac   1500
atcagatata cggagaaaga gtctcctaat ttcttttata agtaaacgaa attcatacct   1560
tactacattt tgttgctcct cctgatcaga tcatgtcttc gacatcttct atgcaataaa   1620
aataaagaaa gaaagaaaga aagaaagatt aaagttagcg ccattctgag cattcatcaa   1680
catataaatt gaaagctagc tatacaaatt tatttttggt tgcatcattt taaaatgaaa   1740
actgagaaga gaaaggtgct agaacagaga tacagttata gatcttcaca ggaacagctg   1800
ccatgcaagg tgggactcag cttccattct caattaccca acgtagaggg agaaggctca   1860
ttcaagctaa atccagggag ttgtaatgca tctggattca tttgttctag caatttcgca   1920
atgccaaatt cagtattcta tgcagctgag aattgcatgg acttttcaca agatttggac   1980
aattttgatc ttcaatcatc cgttaaagtt cacctgcaat acaatcagaa tcccagttta   2040
cctaaaaagc agccgcatca agatgcttat cgaaattcac cagcaagtgt tttctcattt   2100
atgcaggacc cggcagaaga agaagcctcc ctgaacgaaa gacaaaaatg tgttagtttc   2160
agtgaatatc agaagcatca agttagtaca taaatatgtg cccttgtttg tatatatata   2220
tgcagctgca ggttgaaggt ggtttaactc cttgcccttg aactgccaga ttctgaaacc   2280
aagctcatat catgttcaga ctcaccatga gaagcagact cccaatacta tgactagtca   2340
tagcaaaacc agaataagat ggactcagca tcttcacaac cgatttgttg aatgcgtaga   2400
gtttcttggt ggtgctgaaa gtactgcaaa accttttttt tttttcccc agtatcggac   2460
tttatttatt gtgttactac tcatcaaatt ttgggtattt gtttgtagag gctactccta   2520
agggaatcct gaaactgatg gacatcgatg gattgaccat ctttcacgtt aaaagtcact   2580
tgcaggtttg atttgttgtt taaatatttt atggctgtca aatataatca taactcaaag   2640
cccttagttt ttttcttttc tttcttctcc ttttattttt tgtatttcca gaaatatcga   2700
acggcaaggc acattccaga aggtatatta ttttcaagtc cctgataatt gatatggttc   2760
ttaaactata aatttacctg tttgcatttg atttcatcct tgtccatgcc aaatgccagt   2820
gcctaaactt catgaatttt gacgcttttg ttgttttgca tcaaatatca acattgattg   2880
gtgtcacaga caagaacaat taacctgaca tcataacgaa aatatatatt tccaaaaaat   2940
aaaaataaaa aaggccatta atatgccttt ttgaagagta ctttgtgtat acttggaccc   3000
agcatataga ttatttgatt cttatacttt atattcggaa ttcgcatagt taattcagct   3060
atcgtacgat taatgaaaca tgcttttgtc ccatgacatt ttgttggcca aatgctatat   3120
attaaatgag ctgatgtaat tgtcgatctt ccctttaatc tgaattaatt agacctcaaa   3180
agaacaggta ctcgccagtt aacgaaacta atatatcatt tctattttga gatgaccatc   3240
atgggaatag gtttcagcac aaaagggcta ctagattcta ttatgtgaag taagacatcc   3300
```

```
ataaaaatca tccattaatt accttaggcc tatcaacctg ggattttcag acacaacaat   3360
cgtcttcata ttagacccta atgtaatact aatagaatta gccgggccgc cttagaggct   3420
cagttagaaa tggggggaaa aagttacgtc tcagtaaatt tgctgtgcat tttatgcttt   3480
aattatatat gcgtgtgagt ttcgtatgca ggaaaatcaa agcgtgagag gacaaccgac   3540
ctgaatgcaa tagtaaggct cgactcagaa tcgtaagctt ccggtgctga tcatacatat   3600
attctccctt taaatatctc aatccttgca ttgacctcaa gtcatattcc tgttttcaac   3660
aaagagagct atagggaagt gatatctaca tgtatgcaat gcaaccatct aaaaattcta   3720
aatatgcatc cttgatctca gcttcattaa cagaggcatg cagcttgtgg aaacattgaa   3780
attgcagcta gatgtccaga agcgcttaca cgaccaactg gaggtaccct tttatcccta   3840
ttgtgattaa ggaattgata ctgatatatg ttcaccacat tataatccct taacagttct   3900
gtttcacttg tctgggttag gtccaaagaa atctacagtt gcagattgaa gaacaaggga   3960
agcagcttac acagatgtta gaccagcaac taaagccaaa caaatctctc gttgattcca   4020
acaacgtgga tatcgagttg caagataacc aaccaaatga tctcaaagac acgcgtccct   4080
tcaacatata aggtttcaag gatgcccttt atccttgcaa tg                      4122
```

<210> SEQ ID NO 38
<211> LENGTH: 1008
<212> TYPE: DNA
<213> ORGANISM: Citrus sinensis

<400> SEQUENCE: 38

```
atgaaaactg agaagagaaa ggtgctagaa cagagataca gttatagatc ttcacaggaa     60
cagctgccat gcaaggtggg actcagcttc cattctcaat tacccaacgt agagggagaa    120
ggctcattca agctaaatcc agggagttgt aatgcatctg gattcatttg ttctagcaat    180
ttcgcaatgc caaattcagt attctatgca gctgagaatt gcatggactt ttcacaagat    240
ttggacaatt ttgatcttca atcatccgtt aaagttcacc tgcaatacaa tcagaatccc    300
agtttaccta aaaagcagcc gcatcaagat gcttatcgaa attcaccagc aagtgttttc    360
tcatttatgc aggacccggc agaagaagaa gcctccctga acgaaagaca aaaatgtgtt    420
agtttcagtg aatatcagaa gcatcaaatt ctgaaaccaa gctcatatca tgttcagact    480
caccatgaga agcagactcc caatactatg actagtcata gcaaaaccag aataagatgg    540
actcagcatc ttcacaaccg atttgttgaa tgcgtagagt ttcttggtgg tgctgaaaag    600
gctactccta agggaatcct gaaactgatg gacatcgatg gattgaccat ctttcacgtt    660
aaaagtcact tgcagaaata tcgaacggca aggcacattc cagaaggaaa atcaaagcgt    720
gagaggacaa ccgacctgaa tgcaatagta aggctcgact cagaatcagg catgcagctt    780
gtggaaacat tgaaattgca gctagatgtc cagaagcgct tacacgacca actggaggtc    840
caaagaaatc tacagttgca gattgaagaa caagggaagc agcttacaca gatgttagac    900
cagcaactaa agccaaacaa atctctcgtt gattccaaca acgtggatat cgagttgcaa    960
gataaccaac caaatgatct caaagacacg cgtcccttca acatataa                1008
```

<210> SEQ ID NO 39
<211> LENGTH: 4640
<212> TYPE: DNA
<213> ORGANISM: Solanum tuberosum

<400> SEQUENCE: 39

```
ccaaaaagca gcgagatagg agtggacctg gcagtcctcc tgctatggcc gttccactct     60
```

-continued

```
tctctgccca atttcacact tcaattctca cacaaccact tccctcttct cgctcttttt    120
ccgtcggaaa actcttgtct tgctcgtcgt cgtcaacttc catggaacat catgaatcga    180
aattcaagga atttccttat gcatctgttc cgcatagaga gttaatggtg gaacttgtat    240
cgactgtgga gaatcgtctt ggagaatctc tacttccttg tactctgcct tctcatgtgc    300
agtattttga gaatgaatct gctactgctc atgcttctct ctatgtcaga tctggaaatt    360
cctcttctca ggtactctcc gactgattct actacttatt acctattcat tcatttctgc    420
acttgtgcca attatatgta ttagggtatg atataggaat tacttcctgt tggatgtttt    480
gttgaattag tatataggaa tgggttacat ctatgttata aaagcttcta tggaaactca    540
agcggataat ccaattcagg caactatatt tagcaagact gagattcgag tgaatatact    600
ccttctcatc ccattttatc ttaattttgt gttgttgcat cacaatgtta tgaaaaacga    660
aaagcgcaaa aaaactttaa agtaggccgg gactttaagc ctgaaataca aataaagctt    720
gagctttaat gaaaaaaaga cacaataggg aaaaaaatac aaatatatta tatgtatcca    780
agactaataa atataagcat gaataacaaa tctatggaca aagaaattga tctttttata    840
ataaagtgtg ataccaatag cttagaaccc ttattcgcaa ggaaaagatt gtcttaggga    900
ctgaatgacg acaatgaagt gcacattaag cgaggcaaag tgctcaacat attttgagcc    960
ttgcttctgg gattgagcat tcttaaagca cgcctttgac aacattgttg catcactcct   1020
acgtgagacc aaaaaaatgc gccaagaatt ttctcctaat accctccaat atgaatgatg   1080
tcactgctat cttgtacatg gtgaagataa agaaaacaag aaattattat gtactataga   1140
ataatgattg agaaagctag atcttgtcct ctaattttag tggatttggc ttatacagaa   1200
gagttaatcc attacgaatt gtgcttttgt tgattggcct ttttactatg tatgctaaat   1260
atatcagtct tttaataata gtaacatgaa ttgaaatgcc aaatacttaa ttgtataatg   1320
tgctgatggg agttaagaag atcagcagta cttgtattac tctgtgcatc tgtggttttc   1380
tccatccaat gaagtcagac aagatcttta tcaaatctgt tttttttag ctaatttcaa    1440
atttagtatt tcttgttcaa gccatatatc ttgccctttc tagtaaataa cagtcttata   1500
attcctttta attggacatg gctctaagaa aggtgtttgg attatagctt attttaagta   1560
gcttttggct tttaagttcc tttttatttt tgaggtgttt gggaaagaca aaaagtgctt   1620
ttaagcactt atttttaggc gaaaatagta caaaaataag ttaaaaacca aaaattgggc   1680
atgaccaact tatgactttt agcttttagc ttataagcta cttaaaaaaa gtcaatccaa   1740
tcaacccctc tgtagatgaa aaaaagcatc ctaattctat aataggttat tatatgggtt   1800
gttagtattc aaaatgttaa ctttctcaaa aaaaaaatga tataagccaa atggcaaatg   1860
taaaaatagg cccttaaagc aatgttgtgt ctccttttga gttttaagtc tatcaatgga   1920
ttctggtgtc tagagtctaa agggcatgtt ttgaaagaca ataaacaaaa ggggttgtca   1980
taaaaatcac ataccaaaag gggttgtttg tgaattgtac tgcaaactgc catatttttc   2040
acggacgacc cctaacgtcc atttgttaca tttaaaaaat ataaaacaaa cgcaattcgt   2100
gaaatgtggt gcgaattccc actaattttt taatagtttg tagcatgttc tgtgaactgc   2160
atctcaacta gttttgctgt gatcttgtca aagtagtttg atctctgctt gttgcccctc   2220
ccctaggttg aggagctgta aggggaaaat tcttatgatc tgcaatctca ccttctcaca   2280
taagctttcc caacttcaat atctggtggc actgagttcc catctgaata ggtgccgagg   2340
tagtttgtga actagtatct aaactggaac aatagaagtt tcttgctctg gtttaaaatt   2400
```

-continued

```
cagtgcgcat ctcaggaatt tcatagtgta tgacccaatg tgaatggatg acttgaaaat   2460
atgtgattga agtctgtttt gttacagaaa atcaatgtaa acagtgctgt agttgtagta   2520
tgcaatcttg actcttcctt tcaattgaaa ttgactcaca aaaattttcc ttagtttttt   2580
catagtaggt tcctttgatg aatttaccca caatagtcat ttgcaattat tggccgaatt   2640
cacgaaatag tcatcagcag agaaaaatat ggttggctta ccgagatgag tctcatgcct   2700
gatttcaata ggagcttcgg cggttgaggc aatcgccaaa tcagcttgaa cctttctgcg   2760
aaggttggtt tcgatggagc aacaccctta cctttccctg ctaaattggg atttttctgt   2820
tggagttgaa tattggggtt tctgatctgg gcttgaaaga ttggttatag caggattttt   2880
atcagtggca gcagggttat gatcagtttc attgatgttg gtcgcggcaa ccgatttcaa   2940
ttttgaagag ggtgtgtcga aatctgagga caattttggc tgagggggtg tatgattttg   3000
gtgggtggat ttcgaatggg cagtgttttc ctgttgaggt gttgcatggt gatcggaaaa   3060
agagtaggct gagtgttaat ggcatcttgg aggttctgga gaattgttgg gggcaagctt   3120
taggagctta ttactgtcca tgtgttgttc ctctgaagga ttggaagata taggggatga   3180
tgttttgttg ttgttgtggt tgttggtgct agaaggagtt gattttggtg agtttgggat   3240
ttctcgggtg gattggttca aactagcaat tgggggttgt aggagagcag gtgtgttttg   3300
ctgagttgtc ggtgtaggag aggctgcagt tggttgagat gagtatggat tgtggatgta   3360
taactagtgt tttaggtggg ttccgatgca ccatttgggt gtttgctgaa aagatcaata   3420
gatcttcata gagagaagct agagagaata tgcatccaaa attgaccaac caatctaaca   3480
gctcgattca agaattatcc ttgtgcataa tttgtagttt actgcatttc tgctagttgc   3540
gttcacccga tatcttcttg ggaagttat acataaggac tgcaaaagca tcatggagat   3600
agcaagtagg aagtctaatt agttcatcaa tctaatcttc ctatgcttgt tcattcttga   3660
atttggatct ggcttctgtt catttattct tgtccagttc cattcctctg cttatagtta   3720
gtagttccac tgagagttct ttgacaagtc ttgtttctct ttgagattta aagttctttt   3780
tctaacgcgt ataataaaag ataaactggg aacacacagt taacgatttc aactttctca   3840
tcaggagtat atgcaaggtt aatatttttg ccttttctaa attgtgacag gttgatttca   3900
tacttggtag ttgggttcac tgcaacctac ccacaggcgg agcgttgaat attacaagcc   3960
tttcagcata tttgagacct tcaactgatg caccaaactt cttaattgaa gttatccgca   4020
gcagtccaac aactctcatc cttattcttg atctacctcc gcgaaaggac cttgtccaac   4080
atcctgatta cctcaagacc ttttatgagg aaacacaatt agacaagcag agacaacttc   4140
tcgagaaatt acctgaggta aagccttact tctcttcgtc tctatatatt cgatccctag   4200
tctctccatt ggctatcttg gtttctatag aaaccgaacc ttcccaggcc attcgcattg   4260
atgagattat tcaggatcac ataagtcctg ttgctaaggt aatgctggat acatggttgg   4320
atctgtgtgc ttgtactgag agaagattga cagatgatga aagtgcagat ctggctaaga   4380
gggatcgaat aattaagaat aagactatcg agatagatct tgaatcaagc ttccctaggc   4440
ttttcgggca agaagtagcg aaccaggttt taggagtact aagggaaatc tacaacagtt   4500
gaatttcttg ctcctgctgc tgttttattg tgtgattatt gtatgtaatc tttataattc   4560
ttcaacatat aatacattta aaaagatgta aattgagagt aactataaaa gttgcattct   4620
tctatttaga gttcttgtca                                               4640
```

<210> SEQ ID NO 40
<211> LENGTH: 939

<212> TYPE: DNA
<213> ORGANISM: Solanum tuberosum

<400> SEQUENCE: 40
atggccgttc cactcttctc tgcccaattt cacacttcaa ttctcacaca accacttccc 60
tcttctcgct ctttttccgt cggaaaactc ttgtcttgct cgtcgtcgtc aacttccatg 120
gaacatcatg aatcgaaatt caaggaattt ccttatgcat ctgttccgca tagagagtta 180
atggtggaac ttgtatcgac tgtggagaat cgtcttggag aatctctact tccttgtact 240
ctgccttctc atgtgcagta ttttgagaat gaatctgcta ctgctcatgc ttctctctat 300
gtcagatctg gaaattcctc ttctcaggtt gatttcatac ttggtagttg ggttcactgc 360
aacctaccca caggcggagc gttgaatatt acaagccttt cagcatattt gagaccttca 420
actgatgcac caaacttctt aattgaagtt atccgcagca gtccaacaac tctcatcctt 480
attcttgatc tacctccgcg aaaggacctt gtccaacatc ctgattacct caagaccttt 540
tatgaggaaa cgcaattaga caagcagaga caacttctcg agaaattacc tgaggtctcg 600
tcttatctct cttcgcctct atatattcca cccccaacca ctccatgggt tatattgaat 660
tctatacaaa ccgaaccttc ccaggccatt cgcattgatg atattattca ggatcacata 720
agtcctgttg ctaaggtaat gctggataca tggttggatc tgtgtgcttg tactgagaga 780
agattgacag atgatgaaag tgcagatctg gctaagaggg atcgaataat taagaataag 840
actatcgaga tagatcttga atcaagcttc cctaggcttt tcgggcaaga agtagcgaac 900
caggttttag gagtactaag ggaaatctac aacagttga 939

<210> SEQ ID NO 41
<211> LENGTH: 2345
<212> TYPE: DNA
<213> ORGANISM: Solanum tuberosum

<400> SEQUENCE: 41
ctattcctac aatccttccc acattacaat aattacaatg tcaagtctct cactcctatt 60
ggttcttgtc gccggccttt tcgctgctgc acttgccgga ccggcgacct tcgccgatga 120
gaatccgatc aggcaagtag tagtttccga agagctggag aacggaattc ttcaagtcgt 180
cggccagact cgcaatgctc tctccttcgc tcgctttgct atcaggttac taaattcgaa 240
aatgagatcg atttctctat cgttttgctt ttataattaa actaatattg ttctattttt 300
gaatgtttat aaaaggcatc ggaaaaggta cgagtccgtt gaggagatca agcaaaggtt 360
cgagatattt ttggacaatc tgaagatgat ccgatcgcat aacagcaaag gactatcata 420
caaactcggt gtcaatggta tactttctta tcttcaacta ggaaaacaag ttcacactta 480
ctaattagtt atttagatta taaaaactca gtatgaacta cttattcatg atgtataaaa 540
aaaacacttt gtagaagtta agttctttct ttattttact tagtaactaa tcaagctaaa 600
tgaacaattc ttaattgaat tcttatattc atcatatatg cttggataag tgtttgcaac 660
ttatgatcaa tctaattgtt tatcgattac ttttatgttt catggcagag tttaccgacc 720
taacatggga tgagttccgt agacacaagt tgggggcatc tcaaaactgt tctgccacta 780
caaagggcaa tctcaagcta actaacgtcg ttctgccaga gacggtatat ccaatctgaa 840
tgaactccga tcctttatgg ttatatattt ctggagttac tcattagagt taattaaact 900
agtttgtatc taatgcttta ttatttccaa gatggtagag tgcactgagt tgaattttgc 960
tataataaag atagaaacac taaacatcca tccaccgtgt gctgcgttaa ttagtgtgtt 1020
caattggttg cagaaagatt attttttga tcctaacgaa caccaaattt ccaattttgt 1080
gattatagaa ggactggagg gaagtcggta ttgttagccc agtgaaggca cagggcaagt 1140
gcggatcttg ctggacattc aggtgagaat tagttagaat catgttggac tcctaaaatt 1200
gaaatctaat ggagcaggca tatatatgtg gggttttggc agcactactg gtgcactaga 1260
ggcagcatat gcccaagcat ttgggaaggg aatctctctg tcagagcagc agcttgtgga 1320
ctgtgctgga gcttttaata actttggctg caatgggggg ttgccatcac aagcctttga 1380
gtacattaaa ttcaatggtg gtcttgacac tgaagaagca tatccataca ccggcaagaa 1440
tggcatatgt aaattctcac aagcaaatat tggtgtcaaa gtcatcagtt ctgtcaatat 1500
taccctggta attaagatct ctttagtttc cttgggatgg aaccaacttt ttgccagtgt 1560
tattcagccc atttgtttaa cttattgagc tgctgctttt accaattaca catatggact 1620
cctgattaac atgtgttatt acagggtgct gaagatgaac tgaaatacgc agttgcattg 1680
gttaggcctg ttagtgttgc ttttgaggtg gtaaaaggtt tcaaacagta taagagcgga 1740
gtttacacca gcactgaatg tggcgacact cccatggtaa gtcatctgtc ccgagtaacc 1800
tgagaagatg caattatcta ttatcaccta aataggccta tatggacaat attacaaaca 1860
ctgactgttt cattggcagg acgtaaacca tgctgttctt gctgtgggtt acggtgttga 1920
aaatggcgtt ccctactggc tcataaagaa ctcatgggga gcagattggg gtgaggatgg 1980
atacttcaaa atggagatgg gaaagaacat gtgtggtgtt gcgacttgcg catcctaccc 2040
aatcgttgcc taagctttgg agttttgtga aaaaattatg cataaatccg tgttgtccca 2100
gttaatgatg cagcagcagc attcaggctc cattctcaga tttatattca gaacatgtat 2160
ggatcgttat acatacaaaa atggtttagg ctacttatat gaaagaaaca ataagatcaa 2220
aatatttagt tcacagagat tattatgcag gaaaagtccc catgtaattt atacattata 2280
agtaatgaaa gggaggaaga aattcttatt gtaagcatta ttaatccact gttgtcctta 2340
gttta 2345

<210> SEQ ID NO 42
<211> LENGTH: 1071
<212> TYPE: DNA
<213> ORGANISM: Solanum tuberosum

<400> SEQUENCE: 42
atgtcaagtc tctcactcct attggttctt gtcgccggcc ttttcgctgc tgcacttgcc 60
ggaccggcga ccttcgccga tgagaatccg atcaggcaag tagtagtttc cgaagagctg 120
gagaacggaa ttcttcaagt cgtcggccag actcgcaatg ctctctcctt cgctcgcttt 180
gctatcaggc atcggaaaag gtacgagtcc gttgaggaga tcaagcaaag gttcgagata 240
tttttggaca atctgaagat gatccgatcg cataacagca aaggactatc atacaaactc 300
ggtgtcaatg agtttaccga cctaacatgg gatgagttcc gtagacacaa gttgggggca 360
tctcaaaact gttctgccac tacaaagggc aatctcaagc taactaacgt cgttctgcca 420
gagacgaagg actggaggga agtcggtatt gttagcccag tgaaggcaca gggcaagtgc 480
ggatcttgct ggacattcag cactactggt gcactagagg cagcatatgc ccaagcattt 540
gggaagggaa tctctctgtc agagcagcag cttgtggact gtgctggagc ttttaataac 600
tttggctgca atggggggtt gccatcacaa gcctttgagt acattaaatt caatggtggt 660
cttgacactg aagaagcata tccatacacc ggcaagaatg gcatatgtaa attctcacaa 720
gcaaatattg gtgtcaaagt catcagttct gtcaatatta ccctgggtgc tgaagatgaa 780

-continued ctgaaatacg cagttgcatt ggttaggcct gttagtgttg cttttgaggt ggtaaaaggt 840
ttcaaacagt ataagagcgg agtttacacc agcactgaat gtggcgacac tcccatggac 900
gtaaaccatg ctgttcttgc tgtgggttac ggtgttgaaa atggcgttcc ctactggctc 960
ataaagaact catggggagc agattggggt gaggatggat acttcaaaat ggagatggga 1020
aagaacatgt gtggtgttgc gacttgcgca tcctacccaa tcgttgccta a 1071

<210> SEQ ID NO 43

<400> SEQUENCE: 43

000

<210> SEQ ID NO 44
<211> LENGTH: 1632
<212> TYPE: DNA
<213> ORGANISM: Solanum tuberosum

<400> SEQUENCE: 44
atgcaaacta tcaaagcttc ttccttttca ccatttcacc tcaacttgaa ctcaactagt 60
tcatttccca aaattaccaa cttgtacatt caacaaaatt atgaaaaccc catttcttgt 120
tttccctcaa ttcagagcca aaatgcaaaa ttcaaggttt ttactgctat ttccccaagt 180
gtttcaactg aatcagaaac cccatttgat gaaaggactg aaaatgaaaa tcaagaagag 240
aaatttgagt ggtatgctga gtggtaccca ataatgccaa tttgtgatct tgataagagg 300
aggccacatg ggaagaaagt gatgggtatt gatgtggttg tgtggtggga taagaatgag 360
aaagaatgga aagtaatgga tgattcttgt cctcatagat atgctccact ttctgaagga 420
agaattgatc aatggggaag attgcagtgt gtgtatcatg gttggtgctt taatggagct 480
ggtgattgta agtttatccc tcaagctcct agggatgggc ctccggttca tacgtccaaa 540
agagcttgtg caactgttta tccaagttgt gtgcaaaatg acattctttg gttttggcca 600
aactctgatc ctctatacaa ggacatatat ttgacgaaaa ggcctcctta tatacctgaa 660
cttgatgaca gttcgttttc gaaaaccttc atagtcagag atatatcata tgggtatgag 720
cttctgattg aaaaccttat ggacccagct catgtccaat attcacacta tggcattatg 780
aatgttccag tagcccccaa aagtgtgaaa gctgatagag aagggggaag accacttgac 840
ataactgtca cgaagttgga tgtaaatgtc attactgcaa accagggacc tggacggaac 900
acatttgttc cgccttgtgt gtattatagt tattttgctt tcggaggacc tcagggaaaa 960
acatctgctg tatcatctgg aactgtacag gaaaaacctt cagctgagaa gcagaaaaaa 1020
gcacttctag ttttcatctg tattccggtt agtccaggtc atagcagaat tatatttgca 1080
tctccaagaa actttgccac ttgggcagat cgaataattc cacgttggat atttcacctg 1140
ggacaaaatc taattctgga ttctgatttg tatcttcttc atgtggagga gcgcaagcta 1200
aaggaaattg gctcttacaa ttggcataaa gcttgctatg tgccaacaaa ggcagatgcc 1260
attgttgttg cttttagaag gtggctaaac aaatatgcag gtggtcaagt tgattggcgt 1320
ggaaagtaca atggggacct cccgccaact cctccaaggg agcagctgct ggacaggtat 1380
tggactcata cagtgaattg cacaagttgc aatcttgcat ataaaggtct caatgctctt 1440
gaagttgtac tgcagatcgc ctccattggt gtgctcggaa ttgttgctgc tgcaaagcag 1500
ggcacattgt cagtggtggc taggtattct ttggtcacca ttgcattact atgcttcgtg 1560
gcctcgagat ggttatctca ttttatatac aaaaatttcc atttccacga ttatgatcac 1620
gcctttcgtt ga 1632

<210> SEQ ID NO 45
<211> LENGTH: 4284
<212> TYPE: DNA
<213> ORGANISM: Solanum tuberosum

<400> SEQUENCE: 45
gattgacaca agaaaaagaa gcatacactt gaagactagc tagctatatg gaagctctta 60
aaatttctac ttgttttcca ccatttctct tcaacttgaa aacacctaga ttttcaagaa 120
ttatatgtga gaagaaacga aacttttctt tttctctaaa tcatcaacaa ccccacaagt 180
caagattcaa tcttttcact accaatattt ttaattcaac taatgaacca caacaactac 240
ttccaaatga tgaacaagaa attagtacta aaaatgaaaa aaatcaagaa aaagagaaat 300
ttgattggta tgcacaatgg tatccaataa tgccactaag tgaacttgat aagagaaggc 360
cacatgggaa aaaagtgatg ggaattgatt tagtagtgtg gtgggataaa aatttggagg 420
aatggagagt gatggatgat gcttgttctc atagattggc tccactttct caagggagaa 480
ttgatcaatg gggaagattg cagtgtgtgt atcatggttg gtgttttagt ggttctggtg 540
attgcaagtt cattcctcag gctcctagag acaagcttca tgtaattact actccttttt 600
tatctgtcgt ttaacatatt gacacatcta ttaagaaaat catttgataa tatatgtaac 660
attttttttt ttctgtttta cgttatttag ttcatttcag ctcaaggctc aaacacgaaa 720
tttctgatta gggttgaaag tattttgtcc atcctatcat aatccttgga ttttcctttt 780
agatgttttt caaagtgaat cacactttaa actttttta acttctcatt ttacatttag 840
gttaatgacg tacattattt tccattgaca ttataaataa acatgtcttt taacttggtc 900
tcagctagac acacacatcc catgtgacgt cctacatgat atttcacaac ctatgtaatg 960
tcctacttgt attatgccaa gtaggacatg tgtgtctatg tgttcctctt tatgcaagtt 1020
taagtatcta cttgtgcaca ctcaaattag ttgaagagca tagatgacaa ctgaggccaa 1080
taaaagactc atttatgcat ttacgctcag atccggaatt ccactgtccg gtacggagtg 1140
tgcataataa ttgacctggg gtatttccac cccccttcaa tcagtcccgg ggagtttcca 1200
cacacacata tccgggagcc cgcattgaat cggatatgac tctactatca tatcaaatta 1260
agatttactc ctaactcatt attgcatata ttcaaggtca atgagttttc caaataaggt 1320
tgtggtgaaa tgatcattaa ttaaatgttt cgacttttca cataattttg tacagttttt 1380
tttatttact tatgacaagg agtgactata tattaatttt ttgtaggttc acacatccaa 1440
aagagcatgt gtagcagtgt atccaagttt tgtgcaaaat gacattcttt ggttttggcc 1500
caacactgat cctttataca aggacataca cttgagcaaa accccacctt atattccacc 1560
tttagatgat ttaacttcat atgcaaaaac aacacttgtt agagacatcc catatgggta 1620
agtacccttg taaatatatt tggtgtttta ttttggcatg acaaaaaata atttttggaa 1680
aaatattttt aagaaaataa gtcatttttt tgaaaaaaga aaaagttaat aagtcatttt 1740
ctgaagtttg gttaaaatta tcataaagta ctttcaagga aaaacatttt aaaatgactt 1800
ctctcacttt aggcaaaagt cattttccta cacaattatt tcaactctag aaaagtttgc 1860
attagcctat ttattattac ttggtagaat taatatttaa tcagagtttg aaaaatttaa 1920
ttgagaaata attatttttt caggtatgag tttttgattg aaaacctcat ggacccatct 1980
catgtcaatt atgcacatca tggcataatg aaaattggga aaatagaagt tccaaacaga 2040

```
taagaaaatt aaaccttaac atatatacaa atacttgatt tgaattttta ttgtatttgg   2100
atatttttac caaactaata atatataatt aatatgtgca ctgtgaaggg tgatagagaa   2160
ggaggaaaac cacttgatat aagccttgaa aaattagaca taaatggatt tattgcaaag   2220
caaggacatg atgaacacaa atttattgcc ccttgtgtgt actatggtcc atttggtgtt   2280
caaagctatt tggataatta tgaatcaaag gtaattatct tttttcgaat tttctctata   2340
atatcatcgt ttaaccaaat accttttgat tgttataaca tgctattttg ttatagagaa   2400
catataatat aacataaaaa ttgatctaaa taaattggct gctattttaa atgtcctacc   2460
tacccaatgt attcgaggga gaggttagaa tcgaaaaaga tcaggttcca cacatataag   2520
ataggcagaa ggtatgggac gagtagtatg atgtacggag aaccaagacc agtttaatat   2580
taattaattg ctggatcaaa acaaaaatta accccccccc gccccggaag ttaaactgca   2640
ttgattatat gaagggataa gacactagta ccccattgta caccttttgg tttacgtggc   2700
acactctgtg actccacgtg gttgaggcgc gtaggatatg tttggatgcc acgtaagcca   2760
aaaagatgta caaaattaca aataaataaa taaatttaga ataatagaac cttagtttaa   2820
ttaaggtgtg cctctagatt ttgatcatga tctagaggga tacctgtgct ttatcgctaa   2880
tataaaagat ctttactatg aaagtgtact tctaagattt attttatttg tgatgtgatg   2940
caggaagaat catcatcaaa tgatacaaat agaatatttc tagtatttat atgtgttcca   3000
gtaagtccag gtaattgcag attgatgatg acatccttca gaaactttgc tggttgggag   3060
tataaactat ttccaccatg gaaatttcac cttgacaata acctaatcat tgattctgat   3120
ttatatttac ttcatcttca ggtaattaat tatcctctta caatttttttg attttactag   3180
tagtcgtaac attaatcttg ttctttgatt tttattataa ataaaatatt attttttcaa   3240
aatgatttat catgctatct ttagtatttc gtcgtgactt tttcactttt gttatgttag   3300
tttgatattt taatattaat aaaaatgtat catatgtcac gttatgtatc atcacaacct   3360
aactgattgt ttatttattt ttgtcaattt gttttcaact gtaatctatt ataatttatt   3420
gtatttatgg tatgttacac caacacttta ttatgttttt cgttgagttg agggcctagt   3480
gggaacaatc gttctacctt caaggtaggg gtaagatctg tgtatacact accttcctca   3540
atcttcactt gtggattata ctggtatata tatgttgtat ttcttaaaaa agttgattag   3600
tagaaattaa ttatgttgtt catcagactc tccaaaaata ttatcgctac aatgtgtaat   3660
atttagttcc ttttgaagga gcacaagcta agggaaaaag gtccacagaa ttggcaaaaa   3720
atttgttatg taccaacaaa ggcagatgca cttgtggttg gttttagaag atggttgacc   3780
aaatatggag gtgcccaagt tgattggggc acaaaattta ctggtgactt gcaaccaact   3840
cctgctaggg aacaactttt ggacaggtgt gtatatagct cgatcttaaa ttgtgtgaat   3900
cgtcttatct aaatattata cttgttatat gaatgcatag gtactggaca catacaataa   3960
attgtagcag ttgtagcaga gcatataaaa gtctaaatgt ccttgaaatc attatgcaaa   4020
ttatctctgt tgcttcaatt ggaattgctg ctgcagcaaa ggagagtgtc atgtcaattg   4080
ctgcaagata ttcattggtc ttcttggcat tactatgctt catggcttcc agatggttat   4140
ccaaatttat atacaaaagt ttccatttcc atgattatga tcatgccttt tgttaaatgg   4200
tgtactatgt aatagtattg gagatcctaa acattatgta ttattgagga tattgtgtta   4260
tgaataagat ttctccgtca gtaa                                          4284
```

<210> SEQ ID NO 46
<211> LENGTH: 1632

<212> TYPE: DNA
<213> ORGANISM: Solanum tuberosum

<400> SEQUENCE: 46
atggaagctc ttaaaatttc tacttgtttt ccaccatttc tcttcaactt gaaaacacct 60
agattttcaa gaattatatg tgagaagaaa cgaaactttt ctttttctct aaatcatcaa 120
caaccccaca agtcaagatt caatcttttc actaccaata tttttaattc aactaatgaa 180
ccacaacaac tacttccaaa tgatgaacaa gaaattagta ctaaaaatga aaaaaatcaa 240
gaaaaagaga aatttgattg gtatgcacaa tggtatccaa taatgccact aagtgaactt 300
gataagagaa ggccacatgg gaaaaaagtg atgggaattg atttagtagt gtggtgggat 360
aaaaatttgg aggaatggag agtgatggat gatgcttgtt ctcatagatt ggctccactt 420
tctcaaggga gaattgatca atggggaaga ttgcagtgtg tgtatcatgg ttggtgtttt 480
agtggttctg gtgattgcaa gttcattcct caggctccta gagacaagct tcatgttcac 540
acatccaaaa gagcatgtgt agcagtgtat ccaagttttg tgcaaaatga cattctttgg 600
ttttggccca acactgatcc tttatacaag gacatacact tgagcaaaac cccaccttat 660
attccacctt tagatgattt aacttcatat gcaaaaacaa cacttgttag agacatccca 720
tatgggtatg agtttttgat tgaaaacctc atggacccat ctcatgtcaa ttatgcacat 780
catggcataa tgaaaattgg gaaaatagaa gttccaaaca gtgtgaaggg tgatagagaa 840
ggaggaaaac cacttgatat aagccttgaa aaattagaca taaatggatt tattgcaaag 900
caaggacatg atgaacacaa atttattgcc ccttgtgtgt actatggtcc atttggtgtt 960
caaagctatt tggataatta tgaatcaaag gaagaatcat catcaaatga tacaaataga 1020
atatttctag tatttatatg tgttccagta agtccaggta attgcagatt gatgatgaca 1080
tccttcagaa actttgctgg ttgggagtat aaactatttc caccatggaa atttcacctt 1140
gacaataacc taatcattga ttctgattta tatttacttc atcttcagga gcacaagcta 1200
agggaaaaag gtccacagaa ttggcaaaaa atttgttatg taccaacaaa ggcagatgca 1260
cttgtggttg gttttagaag atggttgacc aaatatggag gtgcccaagt tgattggggc 1320
acaaaattta ctggtgactt gcaaccaact cctgctaggg aacaactttt ggacaggtac 1380
tggacacata caataaattg tagcagttgt agcagagcat ataaaagtct aaatgtcctt 1440
gaaatcatta tgcaaattat ctctgttgct tcaattggaa ttgctgctgc agcaaaggag 1500
agtgtcatgt caattgctgc aagatattca ttggtcttct tggcattact atgcttcatg 1560
gcttccagat ggttatccaa atttatatac aaaagtttcc atttccatga ttatgatcat 1620
gccttttgtt aa 1632

<210> SEQ ID NO 47
<211> LENGTH: 792
<212> TYPE: DNA
<213> ORGANISM: Solanum tuberosum

<400> SEQUENCE: 47
atggctgatc gcgtacatcc tcgagattca tcgccggcga gttcaccgcc atcgtcaaat 60
aactccggcg aagtagccgc gggaactaat acaaagcatg tgcggtcgcc gggaacgtat 120
gttgttcaag taccaaaaga tcaaatctac cggtatcctc caccggggaa ttctcgccgt 180
tacgaagctt tgagaaaacg aaagcctcgt cggagcttct gttgccggtg cgtttgctac 240
actttctctc tccttctaat tctcattatc gcacttggaa tcactgctgc cgttctctac 300

```
ctcgtcttcc gtcctgaagc tccaaaatac actatatcca acgtcgcgat taagaatttc    360

aacttaactt cgtcgtctcc agtatcgccg gaattcgacg ttactgtccg agctgaaaat    420

cctaacaata agatcggaat ttactaccgg aaaggtagct ccgtcaccgt attctactcc    480

gatgtccgcc tctctaacgg cgaattgccg gcgttctatc agccaacgaa taacgtaacg    540

gtttttcaga cgccgttaaa aggatcaaac gtcttgcttg gtaacgccgt taagacggcg    600

ttaaggaatg aacagttgaa agggaaagtt ccgtttaagg ttaacatcaa agcgcccgtt    660

aaagttaaag ttggcgccgt taagatgtgg gaaatcaccg ttaaggttaa gtgtgacata    720

acggtgaata cattaacggc caaatcaaaa ataatttctg aagattgtaa atatagtgtt    780

aggctttggt ag                                                        792
```

```
<210> SEQ ID NO 48
<211> LENGTH: 792
<212> TYPE: DNA
<213> ORGANISM: Solanum tuberosum

<400> SEQUENCE: 48

atggctgatc gcgtacatcc tcgagattca tcgccggcga gttcaccgcc atcgtcaaat     60

aactccggcg aagtagccgc gggaactaat acaaagcatg tgcggtcgcc gggaacgtat    120

gttgttcaag taccaaaaga tcaaatctac cggtatcctc caccggggaa ttctcgccgt    180

tacgaagctt tgagaaaacg aaagcctcgt cggagcttct gttgccggtg cgtttgctac    240

actttctctc tccttctaat tctcattatc gcacttggaa tcactgctgc cgttctctac    300

ctcgtcttcc gtcctgaagc tccaaaatac actatatcca acgtcgcgat taagaatttc    360

aacttaactt cgtcgtctcc agtatcgccg gaattcgacg ttactgtccg agctgaaaat    420

cctaacaata agatcggaat ttactaccgg aaaggtagct ccgtcaccgt attctactcc    480

gatgtccgcc tctctaacgg cgaattgccg gcgttctatc agccaacgaa taacgtaacg    540

gtttttcaga cgccgttaaa aggatcaaac gtcttgcttg gtaacgccgt taagacggcg    600

ttaaggaatg aacagttgaa agggaaagtt ccgtttaagg ttaacatcaa agcgcccgtt    660

aaagttaaag ttggcgccgt taagatgtgg gaaatcaccg ttaaggttaa gtgtgacata    720

acggtgaata cattaacggc caaatcaaaa ataatttctg aagattgtaa atatagtgtt    780

aggctttggt ag                                                        792
```

```
<210> SEQ ID NO 49
<211> LENGTH: 3380
<212> TYPE: DNA
<213> ORGANISM: Solanum tuberosum

<400> SEQUENCE: 49

gaggaggttt gactgtattt ctttgttgga aggggcaaaa tcctgttata tatagtagta     60

gtaaattgtt caccttgtaa aatgttatgg tcttatcatt tgttcattcc ttatctacgt    120

tacagaatat ttaaaatata gtcggcattt ggcacttaca tgttgacata ttcatattct    180

ttatattatg tgtatggagt catttagcat ataacaaaaa gaagaagaag aaattaggag    240

caaagattca atttttattt ttcaagaatc ttcatccttt tagtttcttg atttttcgcg    300

ctttttaatt aagacattca ttcaagaaat gcagtttgtt tgttgaaaat attaaaacag    360

aatcaccctt gtttgtgtat tttgatagaa gttgctattt tcttgatctt gatcttgact    420

agtcgttttg gcgaaaaaat gagtattcag aactatgaat tagcaagtga ttgcaactta    480

gagttcccac agatgggatt ttgtttccag cctgaaaact ctgcagaaaa tggttgtcaa    540
```

```
cagcagcagc aacagaattt ttggcctagt actgattcat catcatcgag aacgattata    600
agtcgaatag gatcatcacc ttctgctttt tttgctacag agaggtacct tggattaaca    660
caatatgaaa accaagacaa caataatagt tgttctcaac tatccaagaa tcttggtcct    720
caaactacgt cgtttactca gcaatgtgga aatggattct tggcagattc atcagcacga    780
gttgacaccg attttcctaa gatttcaatg ccatcattca tcagatcaca gttttcaagt    840
agtcaaccat ttggtcctga aggactctat ggaaatccct ttagtaatct atcagagaaa    900
gagaggattt tgcttcttaa gagcaagttg tttagagaaa ttgactcttc aaataggcag    960
cctgcttcaa tccctttca aggaaatcaa gactatggtg taagtacttg attcttgttt   1020
acataataca gtcaaatctc tctgtaacga ttttgtttct cctgatatgt tttggttgct   1080
atagctagat gttgttatcg agaacatcta atataacgta atatgaaagt ttgttccaaa   1140
gaaaacttgg ctggtataga gaggtctgac tgaagtatag tttttcaagt atttgaattt   1200
aagtactttc aattgcttgt tgtctacata atacagtcaa acctctctat aacagtgttg   1260
tttgtcctga tatgttttag ttgctatagc gagatgttat tgaaaaccat ctaatattac   1320
gtaatatgaa agtctgttcc aaagaaaact tggccgttat agagaggcct gactgtagta   1380
ttgtttttca agtttttatt ctgactcgag ttatgttcca acaggtctca aataatacat   1440
gtggttttaa cttggtacat ataaggcaac aatctggaag tcaatcagca aatagtttta   1500
acaactctgg atgttctgga ggatctttat cgagtaaggc acgaatcagg tggactcagg   1560
atcttcatga tcgatttgtt gagtgtgtaa atcgtcttgg aggagctgac agtaagtaaa   1620
tttacacatt tttttagctt ttgtttcttt ggaggtgatc attttggcta tggattaatt   1680
gttcttcact tcatttgcca gaggcgacgc caaaggcaat actaaagctg atggattcag   1740
aaggattaac aatttttcat gtaaaaagtc atttacaggt acttgttaat atgaaagaaa   1800
tactttcttg gaacactttt tgtatttaga caaaattctg aatcaaatgt tttttccttc   1860
ttgttttgac tagaaatatc gaaatgcaaa gttcatccct gaatcgacag aaggtatgta   1920
ttatccgaaa taagcttcat gtttattatg taagagatat tcatcccaca gcttgaaccc   1980
gtgacttgta gttcatacag agacaatttt atcgtttctc caaggctctc ttcattactc   2040
aagcatcagt acagatgtat gctgcttgtt ttatgctttt ttgtgttaat ttctgagcaa   2100
aaaaaaatca aatatgtttc tccaaataca agatccttaa ccacatataa gtatcctcgt   2160
cttgataaac agttaataca ccttatttcc aaacaagttg gagtccgtta tatgaatcct   2220
cacgaaccat gttctaaacc ttcttcgaaa aatcttctct gctttcattt tttatcattt   2280
acgcaacagg tagatccaac atgatgaaaa acacaagaag agactatttc cttaaacaaa   2340
tatgctatta gtaaatctgt tgaagtcttt gaaatctcag aagattgaaa gaacattttc   2400
atcttacttc ttatacaaat cactttaatt ttatttcgta tgatgatgat atgaaatgag   2460
ctttaaatga aggagtgggg gattcgtata gcggaccccca acttgtttga gactgaggcg   2520
tagttgttgt ttaaatttga tatttacagc aaactaaaaa cttaatttta actctgcttg   2580
tggaaaaatg ctctctgaga tatactcaaa tctgtcatta catgctaagt acttaatctt   2640
aaagtttcca tctctttctg gaaatgagag ttccctcctt cctatgatgc agggagatct   2700
ggaaaaacag acagcccgaa taatgtgtca cagatcgaca gcaaaacgta tgttctttgc   2760
aactatcttg acaaattttc gtgactattt tagctggaaa gttaccttaa tacagatttc   2820
ttttcagtgg aatgcaaatc aaagaagcat tgcatatgca gctagaagtc cagaggcgtc   2880
```

ttcacgagca actagaggta catttagtac atgaaaagat ataaatttaa acacttgtag 2940
gcatgcttag agctgaaaca gtatcaaggc aatctttcta aatcttattg tctttctgtt 3000
gttagattca gcggaagtta caattgagga tcgaagaaca aggggagcag ttgaagaaga 3060
tatttgaaca acaacaacaa acaactagga gtctcttgga gacacgaaat tcaagcattt 3120
cgtctcctgc tgatcagttc accccgcacg aagatgaagt tttgctgca gaaagcttca 3180 ataatactca tttccaatct aatataagtt acaatgacat gtaaacaaca ttagttttac 3240
attttttcag ctagtttttg aaagagagtc gacgttagca tttctgtaaa gataattttg 3300
cctcccaagc aaactacaca aaaaaaaaat gtatattaca aagtgaagac ataaatatca 3360
tgcaaaaact taaagtactt 3380

<210> SEQ ID NO 50
<211> LENGTH: 1209
<212> TYPE: DNA
<213> ORGANISM: Solanum tuberosum

<400> SEQUENCE: 50
atgagtattc agaactatga attagcaagt gattgcaact tagagttccc acagatggga 60
ttttgtttcc agcctgaaaa ctctgcagaa aatggttgtc aacagcagca gcaacagaat 120
ttttggccta gtactgattc atcatcatcg agaacgatta taagtcgaat aggatcatca 180
ccttctgctt tttttgctac agagaggtac cttggattaa cacaatatga aaaccaagac 240
aacaataata gttgttctca actatccaag aatcttggtc ctcaaactac gtcgtttact 300
cagcaatgtg gaaatggatt cttggcagat tcatcagcac gagttgacac cgattttcct 360
aagatttcaa tgccatcatt catcagatca cagttttcaa gtagtcaacc atttggtcct 420
gaaggactct atggaaatcc ctttagtaat ctatcagaga aagagaggat tttgcttctt 480
aagagcaagt tgtttagaga aattgactct tcaaataggc agcctgcttc aatccctttt 540
caaggaaatc aagactatgg tgtctcaaat aatacatgtg gttttaactt ggtacatata 600
aggcaacaat ctggaagtca atcagcaaat agttttaaca actctggatg ttctggagga 660
tctttatcga gtaaggcacg aatcaggtgg actcaggatc ttcatgatcg atttgttgag 720
tgtgtaaatc gtcttggagg agctgacaag gcgacgccaa aggcaatact aaagctgatg 780
gattcagaag gattaacaat ttttcatgta aaaagtcatt tacagaaata tcgaaatgca 840
aagttcatcc ctgaatcgac agaagggaga tctggaaaaa cagacagccc gaataatgtg 900
tcacagatcg acagcaaaac tggaatgcaa atcaaagaag cattgcatat gcagctagaa 960
gtccagaggc gtcttcacga gcaactagag attcagcgga agttacaatt gaggatcgaa 1020
gaacaagggg agcagttgaa gaagatattt gaacaacaac aacaaacaac taggagtctc 1080
ttggagacac gaaattcaag catttcgtct cctgctgatc agttcacccc gcacgaagat 1140
gaagtttttg ctgcagaaag cttcaataat actcatttcc aatctaatat aagttacaat 1200
gacatgtaa 1209

<210> SEQ ID NO 51
<211> LENGTH: 144
<212> TYPE: DNA
<213> ORGANISM: Solanum tuberosum -continued

```
<400> SEQUENCE: 51

aagattttta gtatttgatt tatgaatgaa ttttttttt tgagaaatat tttttatttt     60

tactagagta gaaaataatt tttgaaattg aaaatagttt ttaaaaacaa acttaaattt    120

ttttattttt ttttgggggt gggc                                           144
```

METHODS AND COMPOSITIONS FOR PLANT PATHOGEN RESISTANCE IN PLANTS

FIELD OF THE INVENTION

The present disclosure relates to the field of biotechnology. More specifically, the disclosure relates to compositions and methods for producing plants that are resistant to *Ca. Liberibacter* infection in plants, such as Huanglongbing (HLB), also known as citrus greening disease.

INCORPORATION OF SEQUENCE LISTING

The sequence listing that is contained in the file named 10457373PC0seqlist_ST25.txt is filed herewith by electronic submission and incorporated herein by reference.

BACKGROUND

Currently available commercial citrus plants lack tolerance or resistance to Huanglongbing (HLB), also known as citrus greening disease. HLB is caused by species of the phloem-limited, gram-negative bacteria of genus *Ca. Liberibacter*. In the U.S., the predominant pathogenic species is *Ca. Liberibacter asiaticus* (Las); whereas, *Ca. Liberibacter africanus* (Laf) and *Ca. Liberibacter americanus* (Lam) are the predominant pathogenic species in South Africa and Brazil, respectively. *Ca. Liberibacter* is a vector-transmitted pathogen. The vector organisms are the Asian citrus psyllid (ACP), *Diaphorina citri*, and African citrus psyllid, *Trioza erytreae*. HLB was first detected in the United States in August 2005 and has rapidly moved into several citrus producing areas. All commercial citrus plants are susceptible to HLB, and infected citrus plants will irrevocably decline. Thus, HLB has resulted in a severe decline in fruit production in Florida, where HLB has become endemic. Currently, HLB management consists of preventing trees from becoming infected, which includes protecting young flush from the *Ca. Liberibacter* vector organisms and destroying infected plant material. However, due to the lack of rapid curative methods that control HLB, new methods to prevent infection are required to stop the spread of infection and further decline of the U.S. citrus industry.

SUMMARY

Certain embodiments of the disclosure relate to increasing plant resistance to infection by a bacterial species from the genus *Ca. Liberibacter*. One aspect of the present disclosure relates to modified citrus plants comprising genomes in which endogenous genes or regulatory elements thereof may be modified, wherein the modification confers resistance to HLB to the modified citrus plant relative to a plant of the same variety lacking the modification. The citrus plant in certain embodiments may be a grapefruit tree, orange tree, sweet orange tree, or mandarin tree. Further provided are plant parts and seeds of the modified citrus plant. Another aspect of the disclosure is a method of producing a commodity plant product, from the modified citrus plant. In certain embodiments this method comprises collecting the commodity plant product from the modified citrus plant. Further provided are commodity plant products produced by this method. In addition to modified citrus plants, other plants known to be infected by *Ca. Liberibacter* such as solanaceous crops may be genomically modified to disrupted to confer resistance to such infection.

In certain embodiments, modified endogenous genes may encode any polypeptide that interacts with any Sec-dependent effector (SDE) secreted by a bacterial species from the genus *Ca. Liberibacter*. In certain embodiments, modified regulatory elements regulate any endogenous gene that may encode any polypeptide that interacts with any SDE secreted by a bacterial species from the genus *Ca. Liberibacter*. An endogenous gene in particular embodiments may encode PP2-B2/12, Lectin, Cysteine protease, Cysteine protease 15 Papain-like cysteine proteases, Myb family transcription factor, YLS9-like, Cell death suppressor protein Lls1, Acd1-Like, Acd1, accelerated cell death 2 (ACD2) protein, red chlorophyll catabolite reductase-like, NDR1/HIN1-like protein 13 (Cs8g01640), PHL5-like E Cs7g01290), and PHL5 (orange1.1t02259). An SDE in particular embodiments may be Las4025, Las470, Las4065, Las5150, or Las4250.

Still a further aspect of the disclosure is a method of generating a modified plant comprising resistance to *Ca. Liberibacter* infection. In one embodiment, the method comprises the following steps: (a) introducing a genetic modification into the genome of a plant cell, wherein the modification is to an endogenous gene or regulatory element thereof, wherein a polypeptide encoded by the endogenous gene interacts with an SDE secreted by a bacteria species from the genus *Ca. Liberibacter*; (b) regenerating the modified plant from the plant cell or a progenitor cell thereof, wherein the plant comprises the modification (i.e. comprises cells that possess the modification); and (c) identifying a plant comprising the modification and the resistance to *Ca Liberibacter* infection. In a specific example, the plant is a citrus plant or a solanaceous crop.

In certain embodiments, modified endogenous genes may encode any polypeptide that interacts with any SDE secreted by a bacterial species from the genus *Ca. Liberibacter*. In certain embodiments, modified regulatory elements regulate any endogenous gene that may encode any polypeptide that interacts with any SDE secreted by a bacterial species from the genus *Ca. Liberibacter*. An endogenous gene in particular embodiments may encodePP2-B2/12, Lectin, Cysteine protease, Cysteine protease 15A-like, Papain-like cysteine proteases, Myb family transcription factor, YLS9-like, Cell death suppressor protein Lls1, Acd1-Like, Acd1, accelerated cell death 2 (ACD2) protein, red chlorophyll catabolite reductase-like, NDR1/HIN1-like protein 13 (Cs8g01640), PHL5-like (Cs701290), and PHL5 (orangeL1.1t02259). An SDE in particular embodiments may be Las4025, Las470, Las4065, Las5150, or Las4250. In certain embodiments, step (a) comprises a genome-editing technique. In certain embodiments, the genome-editing technique comprises a nuclease, wherein the nuclease introduces a single-strand DNA break or a double-strand DNA break. In certain embodiments, the genome-editing technique comprises a TALEN, a ZFN, meganuclease, or a CRISPR/Cas system. The disclosure still further provides a citrus plant produced by this and the foregoing methods.

Still yet another aspect of the disclosure is a method for conferring a plurality of plants with a resistance to *Ca. Liberibacter* infection. In one embodiment, the method comprises the following steps: (a) introducing a genetic modification into a plurality of plants, wherein the modification is to an endogenous gene or regulatory element thereof, wherein a polypeptide encoded by the endogenous gene interacts with an SDE secreted by a bacteria species from the genus *Ca. Liberibacter*; and (b) screening the plurality of plants for the modification and a resistance to *Ca. Liberibacter* infection. The plurality of plants may include citrus plants or solanaceous plants. In certain embodiments, modified endogenous genes may encode any polypeptide that interacts with any SDE secreted by a bacterial species from the genus *Ca. Liberibacter*. In certain embodiments, modified regulatory elements regulate any endogenous gene that may encode any polypeptide that interacts with any SDE secreted by a bacterial species from the genus *Ca. Liberibacter*. An endogenous gene in particular embodiments may encode PP2-B2/12, Lectin, Cysteine protease, Cysteine protease 15A-like, Papain-like cysteine proteases, Myb family transcription factor, YLS9-like, Cell death suppressor protein Lls1, Acd1-Like, Acd1, accelerated cell death 2 (ACD2) protein, red chlorophyll catabolite reductase-like, NDR1/HIN1-like protein 13 (Cs8g01640), PHL5-like (Cs701290), and PHL5 (orange1,1t02259). An SDE in particular embodiments may be Las4025, Las470, Las4065, Las5150, or Las4250. In certain embodiments, step (a) comprises a genome-editing technique. In certain embodiments, the genome-editing technique comprises a nuclease, wherein the nuclease introduces a single-strand DNA break or a double-strand DNA break. In certain embodiments, the genome-editing technique comprises a TALEN, a ZFN, meganuclease, or a CRISPR/Cas system. The disclosure still further provides a citrus plant produced by this and the foregoing methods.

BRIEF DESCRIPTION OF THE DRAWINGS

FIG. 1A shows binary plasmid used for transgenic expression of CLIBASIA_04025 (Las4025) in citrus. CsVMV: Cassava vein mosaic virus promoter; CaMV 35S: cauliflower mosaic virus 35S promoter; 35T: cauliflower mosaic virus terminator; NosT: nopaline synthase gene terminator; LB: left border of the T-DNA region; RB: right border of the T-DNA region; GFP: green fluorescent protein; NptII: coding sequence of neomycin phosphotransferase II; and Mature protein: nucleotide sequence encoding the mature CLIBASIA_04025 (Las4025) protein without its signal peptide. FIG. 1B shows transgenic grapefruit plants transformed with empty vector (control) or the vector that expressed CLIBASIA_04025 (Las4025) (T1, T2, and T3). FIG. 1C shows Western blots that confirmed transgenic grapefruit lines T1, T2, and T3 expressed CLIBASIA_04025. For these Western blots, a CLIBASIA_04025 (Las4025)-specific antibody was used; the polypeptide with SEQ ID NO:1 was the antigen used to produce this antibody.

FIG. 3A shows the interaction between CLIBASIA_04025 (4025) and cysteine protease (CP, Cs4g07410) detected with a Glutathione-S-transferase (GST) pull-down assay. GST/CP was expressed in *E. coli*, immobilized on glutathione sepharose beads, and incubated with *E. coli* lysates containing Maltose-Binding Protein (MBP)-4025. The bound proteins were immunoblotted using anti-GST and anti-MBP antibodies. FIG. 3B shows the interaction between 4025 and CP detected using Bimolecular Fluorescence Complementation (BiFC), in which EYFP fluorescence represents a protein-protein interaction. Expression vectors with 4025 without its signal peptide or CP cloned in-frame with either the N- or C-terminal fragments of EYFP (EYFPN and EYFPC) were synthesized. Citrus protoplasts were co-transformed with combinations of EYFPC or EYFPN with 4025 or CP expression vectors. The co-expression of 4025-EYFPN and EYFPC/CP and the co-expression of EYFPC-4025 and CP-EYFPN produced strong signal in the citrus protoplasts; whereas, no detectable fluorescence signal was produced by the negative control combinations.

FIG. 4A shows expression of MYTL in grapefruit driven by the 35S promoter reduced plant growth. FIG. 4B shows the normal amount of starch particles, red stain, that accumulated in wildtype grapefruit. FIG. 4C shows overexpression of MYTL in grapefruit induced greater starch accumulation than displayed by wild-type grapefruits.

FIG. 5A. Yeast-two hybrid (Y2H) assay. Full-length SDE15 fused to the GAL4 DNA binding domain (BD) was expressed in combination with full-length CtACD2 fused to the GAL4 activation domain (AD) in the yeast strain Y2HGold. Strains were grown on double drop-out medium (DDO) with -Trp and -Leu and screened on quadruple dropout medium (QDO) with -Trp, -Leu, -Ade and -His supplemented with X-α-Gal and Aureobasidin A (QDO/X/A). The empty BD and AD vectors were used as the negative controls. FIG. 5B. Bimolecular fluorescence complementation (BiFC) assay. Coding sequence of SDE15 without signal peptide fused to N-terminal or C-terminal fragments of EYFP vectors pSAT6-nEYFP-C1 and pSAT6-cEYFP-C1-B were co-transformed with full-length CtCtACD2 and CtCtACD1 protein which fused to C-terminal and N-terminal fragments of EYFP vectors pSAT6-nEYFP-C1 and pSAT6-cEYFP-C1-B into citrus protoplasts. The EYFP fluorescence of protoplasts were imaged 1 day after incubation using a Leica fluorescence microscope. For genuine interaction between SDE15 and CtACD2, co-expression of SDE15-$EYFP^N$ and $EYFP^C$-CtACD2 or $EYFP^C$-SDE15 and CtACD2-$EYFP^N$ should give strong fluorescent signals in protoplast. Co-transformations of SDE15-$EYFP^N$ and $EYFP^C$, $EYFP^N$ and $EYFP^C$-SDE15, SDE15-$EYFP^N$ and $EYFP^C$-SDE15, CtACD2-$EYFP^N$ and $EYFP^C$, $EYFP^N$ and $EYFP^C$-CtACD2, CtACD2-EYFP and $EYFP^C$-CtACD2, $EYFP^N$+$EYFP^C$ were used as negative controls which didn't produce any detectable fluorescence signal. FIG. 5C. Glutathione-S-transferase (GST) pull-down assay. GST-SDE15 and GST empty vectors were expressed in *E. coli*, immobilized on glutathione sepharose beads, and incubated with *E. coli* lysate containing MBP-CtACD2. Total cell extract (Input) and eluted protein (Elute) were immunoblotted using the anti-MBP and anti-GST antibody. FIG. 5D. Hypersensitive response (HR) assay. *Agrobacterium tumefaciens* strain GV2260 harboring binary vectors containing SDE15 and CtACD2 were infiltrated into leaves of *N. benthamiana* at the concentration of $10^8$ CFU $ml^{-1}$. Two days later, another *Agrobacterium tumefaciens* strain GV2260 harboring the binary vector containing AvrBsT protein that can trigger HR was infiltrated on the same area of the leaves treated before. HR induction was observed and photographed 2-3 days past-inoculation. All experiments were repeated three times with the similar results, and only one leaf was presented. FIG. 5E. Electrolyte leakage associated with HR induced by AvrBsT 2 days post infiltration. Leaf discs of AvrBsT infiltrated plants were floated on deionized water with shaking. The conductivity of the solution was measured after 4 h shaking. Error bars indicate standard error of mean (n=3). Alphabets represent significant differences in different types of samples.

FIG. 6 Characterization of SDE15, FIG. 6A. Sequence analysis of SDE15. Amino acid sequence of SDE15 (96 aa) with N-terminal signal peptide (highlighted in yellow) predicted using SignalP V4.1. The cleavage site localizes between the $22^{nd}$ and $23^{rd}$ aa (SCG-DT). FIG. 6B. Yellowing and mottling of the leaf were observed in transgenic citrus cultivar 'Duncan' plants constitutively expressing SDE15 compared with the leaf of empty-vector (EV) transgenic citrus. FIG. 6C. SDE15 detection in phloem sap. Phloem sap was isolated from the bark of both healthy and HLB infected citrus. T1: total bark proteins; T2: total bark proteins after phloem sap isolation; P: phloem sap. FIG. 6D. Subcellular localization of SDE15. SDE15-EYFP was co-expressed with the plasma membrane localization-marker PM-CFP or the nucleus localization-marker CFP-nucleus in leaves of *N. benthamiana. Agrobacterium* strains carrying the corresponding expression plasmids were infiltrated at the optical density ($OD_{600}$) of 0.2. Subcellular localization of SDE15-EYFP was inspected and photographed 1 day post infiltration. Scale bars: 10 μm. FIG. 6E, FIG. 6F. qRT-PCR analysis of SDE15 expression in different Las hosts (FIG. 6E) and in different stages of Las infection (FIG. 6F). Relative transcript abundances were determined using gyrase subunit A of Las (CLIBASIA_00325) and citrus house keeping gene encoding glyceraldehyde-3-phosphate dehydrogenase-C (GAPDH-C) as endogenous controls. Bars represent the mean of eight replicates. Asterisks represent significant differences in the transcript abundance between citrus and psyllids (**p-Value<0.01). Alphabets represent significant differences in samples of different Las infection stages. Error bars indicate standard error of mean (n=6). All experiments were repeated three times with the similar results.

FIG. 7. Hypersensitive reaction (HR) was repressed in SDE15-transgenic citrus.

FIG. 9 SDE15-transgenic citrus became more susceptible to citrus canker caused by a virulent strain (XacA 306) of *Xanthomonas citri* pv. *citri*.

FIG. 10. SDE15 interacts with CsACD2 protein. FIG. 10A. Yeast-two hybrid (Y2H) assay using SDE15 as the bait and full-length CsACD2 protein as prey. Full-length SDE15 fused to the GAL4 DNA binding domain (BD) was expressed in combination with full-length CsACD2 fused to the GAL4 activation domain (AD) in the yeast strain Y2HGold. Strains were grown on double dropout medium (DDO) with -Trp and -Leu and screened on quadruple dropout medium (QDO) with -Trp, -Leu, -Ade and -His supplemented with X-α-Gal and Aureobasidin A (QDO/X/A). The empty BD and AD vectors were used as the negative controls. FIG. 10B Bimolecular fluorescence complementation (BiFC) assay. The coding sequence of SDE15 (without its signal peptide) fused to that of the N-terminal or C-terminal fragment of EYFP in vectors pSAT6-nEYFP-C1 and pSAT6-cEYFP-C1-B, respectively, was co-transformed into citrus leaf protoplasts with full-length CsACD2 or CsACD2 protein which fused to the C-terminal or N-terminal fragment of EYFP in vectors pSAT6-nEYFP-C1 and pSAT6-cEYFP-C1-B. The EYFP fluorescence of protoplasts were imaged, 1 day after incubation, using a Leica fluorescence microscope. Co-transformations of SDE15-$EYFP^N$ and $EYFP^C$, $EYFP^N$ and $EYFP^C$-SDE15, SDE15-$EYFP^N$ and $EYFP^N$-SDE15, CsACD2-$EYFP^N$ and $EYFP^C$, $EYFP^N$ and $EYFP^C$-CsACD2, CsACD2-$EYFP^N$ and $EYFP^C$-CsACD2, $EYFP^N$+$EYFP^C$ were used as negative controls, which did not produce any detectable fluorescence signal. FIG. 10C, FIG. 10D, FIG. 10E. Glutathione-S-transferase (GST) pull-down assay. GST-SDE15 and GST empty vectors were expressed in *E. coli*, immobilized on glutathione sepharose beads, and incubated with *E. coli* lysate containing MBP-CsACD2. Total cell extract (Input) and eluted protein (Elute) were immunoblotted using the anti-MBP and anti-GST antibody.

FIG. 12. SDE15 represses the hypersensitive response in tobacco and promotes the RCCR activity of CsACD2 in vitro. FIG. 12A. Hypersensitive response (HR) assay. *A. tumefaciens* strain GV2260 harboring binary vectors that are designed to express SDE15, CsACD2 (Left) or truncated SDE15 (Right) were co-infiltrated into leaves of *N. benthamiana* at the concentration of $10^8$ CFU $ml^{-1}$. Two days later, another *A. tumefaciens* strain GV2260 harboring the binary vector that is designed to express AvrBsT protein, which can trigger an HR was infiltrated on the same area of the leaves. HR induction was observed and photographed 2-3 days past-inoculation. All experiments were repeated three times with the similar results. FIG. 12B. Electrolyte leakage associated with the HR induced by AvrBsT 2 days post infiltration. Leaf discs were floated on deionized water with shaking. The conductivity of the solution was measured after 4 h shaking. Error bars indicate standard error of mean (n=3). Alphabets represent significant differences in different types of samples. FIG. 12C. Coupled PAO/RCCR assay to measure CsACD2 activity. Activity of purified recombinant CsACD2 was assessed in a coupled assay using purified PAO and co-factors. pFCC as the product was measured by HPLC. Purified GST-SDE15, $SDE15^{\Delta N}$ or $SDE15^{\Delta C}$ were added to the reaction mixture to examine whether full-length SDE15 and truncated SDE15 proteins affect the activity of CsACD2. As negative controls, purified GST protein or mock purification of the vector alone without CsACD2 was added to the reaction system. Error bars represent SD (n=3). This experiment was done twice with similar results.

BRIEF DESCRIPTION OF THE SEQUENCES

Figure 1:
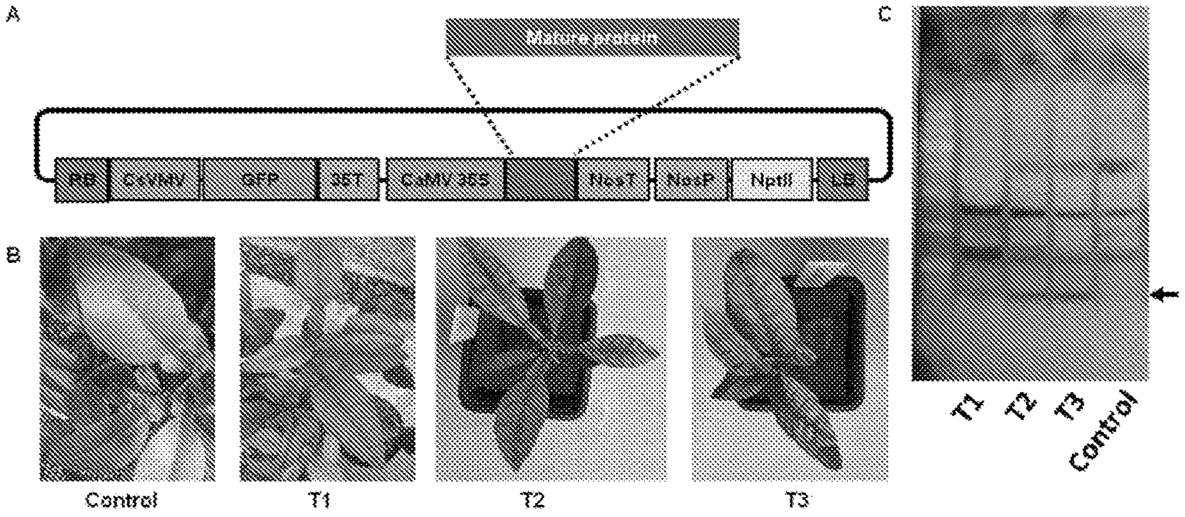
FIG. 1 shows transgenic expression of CLIBASIA_04025 (Las4025) in grapefruit (*Citrus paradisi*) caused HLB-like symptoms.

SEQ ID NO:1 Antigen sequence used to produce CLIBASIA_04025 (Las4025)-specific antibody from *Ca. Liberibacter asiaticus.*

SEQ ID NO:2 CLIBASIA_04025 cDNA sequence from *Ca. Liberibacter asiaticus.*

SEQ ID NO:3 CLIBASIA_00470 cDNA sequence from *Ca. Liberibacter asiaticus.*

SEQ ID NO:4 CLIBASIA_04065 cDNA sequence from *Ca. Liberibacter asiaticus.*

SEQ ID NO:5 CLIBASIA_05150 cDNA sequence from *Ca. Liberibacter asiaticus.*

SEQ ID NO:6 CLIBASIA_04250 cDNA sequence from *Ca. Liberibacter asiaticus.*

SEQ ID NO:7 ACD2 Cs1g22670 gene sequence from *Citrus sinensis* cultivar Valencia.

SEQ ID NO:8 ACD2 Cs1g22670.1 cDNA sequence from *Citrus sinensis* cultivar Valencia.

SEQ ID NO:9 AT4G37000 DNA sequence from *Arabidopsis thaliana.*

SEQ ID NO:10 AT4G37000 protein sequence from *Arabidopsis thaliana.*

SEQ ID NO:11 Cysteine Protease Cs4g07410 gene sequence from *Citrus sinensis* cultivar Valencia.

SEQ ID NO:12 Cysteine Protease Cs4g07410.1 cDNA variant sequence from *Citrus sinensis* cultivar Valencia.

SEQ ID NO:13 Cysteine Protease CS4g07410.2 cDNA variant sequence from *Citrus sinensis* cultivar Valencia.

SEQ ID NO:14 RCCR-like Cs1g22680 gene sequence from *Citrus sinensis* cultivar Valencia.

SEQ ID NO:15 RCCR-like Cs1g22680.1 cDNA sequence from *Citrus sinensis* cultivar Valencia.

SEQ ID NO:16 Lis' Cs9g02990 gene sequence from *Citrus sinensis* cultivar Valencia.

SEQ ID NO:17 Lis' Cs9g02990.1 cDNA sequence from *Citrus sinensis* cultivar Valencia.

SEQ ID NO:18 ACD1-like Cs9g03000 gene sequence from *Citrus sinensis* cultivar Valencia.

SEQ ID NO:19 ACD1-like Cs9g03000.1 cDNA sequence from *Citrus sinensis* cultivar Valencia.

SEQ ID NO:20 ACD1 Cs8g15480 gene sequence from *Citrus sinensis* cultivar Valencia.

SEQ ID NO:21 ACD1 Cs8g15480.1 cDNA sequence from *Citrus sinensis* cultivar Valencia.

SEQ ID NO:22 Cysteine Proteinase 15A-like Cs3g25530 gene sequence from *Citrus sinensis* cultivar Valencia.

SEQ ID NO:23 Cysteine Proteinase 15A-like Cs3g25530.1 cDNA sequence from *Citrus sinensis* cultivar Valencia.

SEQ ID NO:24 Myb orange1.1t02260 gene sequence from *Citrus sinensis* cultivar Valencia.

SEQ ID NO:25 Myb orange1.1t02260.1 cDNA sequence from *Citrus sinensis* cultivar Valencia.

SEQ ID NO:26 YLS9-like Cs2g29120 gene sequence from *Citrus sinensis* cultivar Valencia.

SEQ ID NO:27 YLS9-like Cs2g29120.1 cDNA sequence from *Citrus sinensis* cultivar Valencia.

SEQ ID NO:28 Lectin orange1.1t05126 gene sequence from *Citrus sinensis* cultivar Valencia.

SEQ ID NO:29 Lectin orange1.1t05126.1 cDNA sequence from *Citrus sinensis* cultivar Valencia.

SEQ ID NO:30 PP2-B2/12 orange1.1t04174 gene sequence from *Citrus sinensis* cultivar Valencia.

SEQ ID NO:31 PP2-B2/12 orange1.1t04174.1 cDNA sequence from *Citrus sinensis* cultivar Valencia.

SEQ ID NO:32 NDR1/HIN1-like protein 13 Cs8g01640 gene sequence from *Citrus sinensis* cultivar Valencia.

SEQ ID NO:33 NDR1/HIN1-like protein 13 Cs8g01640.1 cDNA sequence from *Citrus sinensis* cultivar Valencia.

SEQ ID NO:34 PHL5 orange1,1t02259 gene sequence from *Citrus sinensis* cultivar Valencia.

SEQ ID NO:35 PHL5 orange1.1t02259.1 cDNA variant sequences from *Citrus sinensis* cultivar Valencia.

SEQ ID NO:36 PHL5 orange1.1t02259.2 cDNA variant sequences from *Citrus sinensis* cultivar Valencia.

SEQ ID NO:37 PHL5-like Cs7g01290 gene sequence from *Citrus sinensis* cultivar Valencia.

SEQ ID NO:38 PHL5-like Cs7g01290.1 cDNA sequence from *Citrus sinensis* cultivar Valencia.

SEQ ID NO:39 ACD2 LOC102591737 gene sequence from *Solanum tuberosum.*

SEQ ID NO:40 ACD2 NM_001318612.1 CDS sequence from *Solanum tuberosum.*

SEQ ID NO:41 Cysteine Proteinase 3 LOC102578939 gene sequence from *Solanum tuberosum.*

SEQ ID NO:42 Cysteine Proteinase 3 XM_006342320.2 CDS sequence from *Solanum tuberosum.*

SEQ ID NO:43 Lisl LOC102597185 gene sequence from *Solanum tuberosum* (bp 734-7789).

SEQ ID NO:44 Llsl XM_006364374.2 CDS sequence from *Solanum tuberosum.*

SEQ ID NO:45 Llsl/ACD1-like LOC102604461 gene sequence from *Solanum tuberosum.*

SEQ ID NO:46 Llsl/ACD1-like XM_006340026.2 CDS sequence from *Solanum tuberosum.*

SEQ ID NO:47 YLS9-like LOC102602250 gene sequence from *Solanum tuberosum.*

SEQ ID NO:48 YLS9-like NM_001289011.1 CDS sequence from *Solanum tuberosum.*

SEQ ID NO:49 Myb family transcription factor LOC102578723 gene sequence from *Solanum tuberosum.*

SEQ ID NO:50 Myb family transcription factor XM_006362170.2 CDS sequence from *Solanum tuberosum.*

SEQ ID NO:51 Llsl LOC102597185 gene sequence from *Solanum tuberosum* (bp 1-144).

DETAILED DESCRIPTION

Introduction

The disclosure provides a modified plant comprising a genetic modification to an endogenous gene or regulatory element thereof, wherein the polypeptide encoded by said endogenous gene interacts with Sec-dependent pathway effector polypeptides secreted by pathogenic species of *Ca. Liberibacter*. In specific examples, the modified plant is citrus, wherein the citrus plant exhibits increased resistance to HLB as a result of the modification. Also provided are seeds, fruit, and plant parts of such plants. In another embodiment, methods are provided for generating a modified plant that is tolerant to *Ca. Liberibacter* infection, such as citrus plant that is tolerant to HLB. Methods are also provided for conferring plants with resistance to *Ca. Liberibacter* infection, such as conferring citrus plants with a resistance to HLB, and screening that plurality of plants for said resistance. In specific examples this is accomplished using nucleic acid modification techniques, genome recombination techniques, genome editing techniques, or a combination thereof.

Definitions

Expression: The term "expression" as used herein refers to the transcription of a particular nucleic acid sequence to produce sense or antisense RNA or mRNA, and/or the translation of an mRNA molecule to produce a polypeptide, with or without subsequent post-translational events. Expression also encompasses production of a functional nucleic acid (e.g., an RNAi, antisense molecule, ribozyme, aptamer, etc.).

Genome editing: Modifying a genome with techniques that employ targeted mutagenesis to activate DNA repair pathways. These techniques include, but are not limited to, those that utilize endonucleases to generate single-strand and double-strand DNA breaks that activate DNA repair pathways. Genome editing techniques may also comprise systems that enable targeted editing at any genomic locus. These targeting systems include, but are not limited to, polypeptides, such as, Transcription Activator-Like Effectors (TALEs) and zinc fingers (ZFs), or nucleic acids, such as, Clustered Regularly Interspaced Short Palindromic Repeats/Cas (CRISPR/CAS) single guide RNAs or NgAgo (Argonaute) single strand DNAs. As used herein, "genome editing" and "genome-engineering" are interchangeable.

Genetic modification: A DNA sequence difference, epigenetic difference, or combination thereof between two genomes of the same species in which one genome is identified as the modified genome and the other is identified as the unmodified genome and the DNA sequence or epigenetic difference is the result of applying genome modifying techniques to the unmodified genome to yield the modified genome. A genetic modification, as used herein, encompasses any insertion, deletion, or substitution of a nucleotide sequence of any size and nucleotide content, any epigenetic modification to any number of nucleotides, or a combination thereof. A genetic modification, as used herein, may also encompass introduction of one or more exogenous coding nucleic acids that do not integrate into the unmodified genome, yet are capable of autonomous replication. In certain embodiments, a modification to an endogenous gene or regulatory element thereof may be a deletion, a substitution, or an insertion that reduces expression of the endogenous gene or the polypeptide for which it encodes. In specific embodiments, the modification may be an indel, wherein the indel may cause a frameshift mutation, a missense mutation, a nonsense mutation, a neutral mutation, or a silent mutation. In specific embodiments, a modification to a regulatory element of an endogenous gene may alter or eliminate a function of the regulatory element. In further contemplated embodiments, the modification may comprise a nucleic acid sequence that provides exogenous control of endogenous gene, mRNA, or polypeptide expression levels. In specific embodiments, the modification may also disrupt a post-translational process of a polypeptide encoded by an endogenous gene. Post-translational processes in certain embodiments may be post-translational modification, protein sorting, or proteasomal degradation.

Genetically modified cell: A cell in which the endogenous genome has been genetically modified; a cell in which one or more exogenous, coding nucleic acids have been introduced that do not integrate into the genome, yet are capable of autonomous replication; or a combination thereof.

Genetically modified plant: A plant comprising at least one genetically modified cell. A genetically modified plant may be regenerated from a genetically modified cell or plant part comprising genetically modified cells, and thus the genetic modification may be heritable and inherited by progeny thereof. The progeny thereof that inherit the genetic modification are also considered genetically modified plants. A genetically modified plant, as used herein, also refers to a plant in which at least one genetically modified cell is introduced to a plant or arises as a result of genetic modification techniques directly applied to the plant.

Genetic modification techniques: Any technique known to those in the art that can modify the genome of a cell including, but not limited to, genome editing, site-specific genetic recombination, epigenetic modifications, and genetic transformation.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be from another species, organism, plant, tree, or variety, or may be native to the host genome, but be rearranged with respect to other genetic sequences within the host sequence. For example, a regulatory sequence may be heterologous in that it is linked to a different coding sequence relative to the native regulatory sequence. In addition, a particular recombinant DNA molecule may be heterologous with respect to a cell or organism into which it is inserted when it would not naturally occur in that particular cell or organism.

Overexpress: As used herein, "overexpress" refers to increased expression of a gene or coding sequence over that found in nature or a control plant or tissue. In some embodiments, "overexpress" may refer to greater expression of a gene or coding sequence in a genetically modified plant, when compared to a plant lacking the genetic modification.

Plant: As used herein, the term "plant" refers to citrus or solanaceous plant, or any other plant that can be infected by a *Ca Liberibacter* species.

Plant part: The term "plant part" refer to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile. A plant part may be any part of the plant from which another plant may arise.

Promoter: A recognition site on a DNA sequence or group of DNA sequences that provides an expression control element for a structural gene and to which RNA polymerase specifically binds and initiates RNA synthesis (transcription) of that gene.

$R_0$ genetically modified plant: A plant that has been genetically modified or has been regenerated from a plant cell or cells that have been genetically modified.

Reduction of Expression: The term "Reduc(e), (es) or (ing) the expression" of a gene or polypeptide in a plant or a plant cell includes inhibiting, interrupting, knocking-out, or knocking-down the gene or polypeptide, such that transcription of the gene and/or translation of the encoded polypeptide is reduced as compared to a corresponding control plant, plant cell, or population of plants or plant cells in which expression of the gene or polypeptide is not inhibited, interrupted, knocked-out, or knocked-down. "Reduced expression" encompasses any decrease in expression level (e.g., a decrease of 10% or more, 20% or more, 30% or more, 40% or more, 50% or more, 60% or more, 70% or more, 80% or more, 90% or more, or even 100%) as compared to the corresponding control plant, plant cell, or population of plants or plant cells. In some embodiments, reducing expression by 50% or more may be particularly useful. Expression levels can be measured using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting Regeneration: The process of growing a plant from a plant cell (e.g., plant protoplast, callus, or explant).

Rootstock: As used herein, a "rootstock" refers to underground plant parts such as roots, from which new above-ground growth of a plant or tree can be produced. In accordance with the disclosure, a rootstock may be used to grow a different variety through asexual propagation or reproduction such as grafting. As used herein, a "scion" refers to a plant part that is grafted onto a rootstock variety. A scion may be from the same or a different plant type or variety.

Site-specific genome modification: Any genome modification technique that employs an enzyme that can modify a nucleotide sequence in a sequence-specific manner. Site-specific genome modification enzymes include, but are not limited to, nucleases, endonucleases, recombinases, invertases, transposases, methytransferases, demethlylases, aminases, deaminases, helicases, and any combination thereof.

Transformation construct: A chimeric DNA molecule which is designed for introduction into a host cell by genetic transformation. Preferred transformation constructs will comprise all of the genetic elements necessary to direct the expression of one or more exogenous nucleic acid sequences. In particular embodiments of the instant disclosure, it may be desirable to introduce a transformation construct into a host cell in the form of an expression cassette.

Transgene: A segment of DNA which has been incorporated into a host genome or is capable of autonomous replication in a host cell and is capable of causing the expression of one or more nucleic acid sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was modified with the DNA segment.

Vector: A DNA molecule designed for transformation into a host cell. Some vectors may be capable of replication in a host cell. A plasmid is an exemplary vector, as are expression cassettes isolated therefrom.

Tolerance or resistance: Tolerance encompasses any relief from, reduced presentation of, improvement of, or any combination thereof of any symptom of an infection by a *Ca. Liberibacter* species. Resistance encompasses tolerance as well as a reduction of bacteria upon infection or reduction of ability to infect by a *Ca. Liberibacter* species. In specific embodiments of the disclosure, citrus plant may be provided that are defined as comprising a complete or less than complete resistance or tolerance to HLB. This may be assessed, for example, relative to a citrus plant not comprising a genetic modification according to the disclosure.

Hypersensitive Response (or Reaction): The hypersensitive response (or sometimes referred to a hypersensitive reaction) (HR) is plant defense mechanism that protects a plant against infection by a plant pathogen. HR is a form of cell death often associated with plant resistance to pathogen infection to prevent the spread of the potential pathogen from infected to uninfected tissues. Cell death is activated by recognition of pathogen-derived molecules by the resistance (R) gene products, and is associated with the massive accumulation of reactive oxygen species (ROS), salicylic acid (SA), and other pro-death signals such as nitric oxide (NO). *Ca. Liberibacter* species inhibit hypersensitive response, which inhibits the plant from defending itself against the *Ca. Liberibacter, Xanthomonas* species, and other pathogens It is shown herein that secretion of SDEs by a bacterial species inhibit HR. The genomic modifications described herein prevent or minimize inhibition of HR by SDES.

DETAILED DESCRIPTION OF EMBODIMENTS

The disclosure provides a significant improvement over the art due to the lack of agronomically acceptable citrus plants with tolerance or resistance to HLB. HLB is a disease caused by species of the phloem-limited, gram-negative bacteria of genus *Ca. Liberibacter*. In the U.S., the predominant pathogenic species is *Ca. Liberibacter asiaticus* (Las); whereas *Ca. Liberibacter africanus* (Laf) and *Ca. Liberibacter americanus* (Lam) are the predominant pathogenic species in South Africa and Brazil, respectively. *Ca. Liberibacter* is a vector-transmitted pathogen. The vector organisms are the Asian citrus psyllid, *Diaphorina citri*, and African citrus psyllid, *Trioza erytreae*. HLB was first detected in the United States in August 2005 and has rapidly moved into several citrus producing areas. All commercial citrus plants are susceptible to HLB, and infected citrus plants will irrevocably decline. Plant decline is usually preceded by a decline in the quality of the fruit and fruit drop. Fruit from infected plants are smaller, yield less juice, and have higher acidity, lower sugar and greener peel color than those from uninfected plants.

HLB has resulted in a severe decline in fruit production in Florida, where it has become endemic. However, due to the lack of rapid curative methods that control HLB, prevention of new infections is essential in HLB management. Currently, HLB management consists of preventing trees from becoming infected, which includes protecting young flush from HLB vector organisms and destroying infected plant material.

New infections could be prevented, and the disease could be managed, by planting trees that are tolerant or resistant to the disease. However, utilization of resistant germplasm to slow the spread of HLB is difficult due to the lack of commercially available resistant rootstock/scion combinations. Identification and incorporation of resistance traits from tolerant citrus species and relatives is also a potential disease management strategy, but applying conventional plant breeding methods to citrus plants is difficult and time consuming due to their level of nucellar embryony and long juvenile phases.

Genetically modifying citrus plants is a viable alternative to conventional plant breeding. It is a relatively rapid process and some techniques allow for targeted modification of genetic locus without significant off-target effects. In such cases, genetic modification of existing cultivars has been a key component to combat HLB. In some embodiments, the disclosure employs genetic modification to render the modified citrus plant tolerant to pathogenic *Ca. Liberibacter* species. In specific embodiments, the disclosure provides a citrus plant that is tolerant to *Ca. Liberibacter* effector proteins. As will be understood to those of skill in the art, once a genetic modification conferring resistance to HLB is generated this could readily be introduced into any other cultivar by crossing.

Zebra Chip (ZC) is an economically important disease that occurs in commercial potato fields in the United States, Mexico, Central America, and New Zealand (Munyaneza, J. E. Am. J. Pot Res (2012) 89: 329). ZC was first found in Mexico in 1994 then spread to the United States in 2000 (Rondon, S., Schreiber, A., Hamm, P., Olsen, N., Wenninger, E., Wohleb, C., Waters, T., Cooper, R., Walenta, D., and Reitz, S. 2017. Potato Psyllid Vector of Zebra Chip Disease in the Pacific Northwest. A Pacific Northwest Extension Publication. pp. 1-8). Similar to Huanglongbing (HLB), ZC and diseases of other solanaceous crops are associated with a fastidious alpha-proteobacterium belonging to the '*Candidatus*' genus *Liberibacter, Candidatus Liberibacter solanacearum*' (CLso), that is transmitted by a phloem-feeding psyllid vector, *Bactericera cockerelli* (Jagoueix, S., et al. 1994, Int. J. Syst. Bacteriol. 44:379-386; Bove, J. M. 2006, J. Plant Pathol. 88:7-37; Pelz-Stelinski et al. 2010, J. Econ. Entomol. 103:1531-1541). CLso vectored by *B. cockerelli* results in a severe decline of potato, tomato, and pepper production. Current management of CLso consists of chemical controls using insecticides (Rondon et al. 2017). Due to the rapid spread of CLso, new methods to prevent infections are required.

Exemplary *Ca. Liberibacter* effector proteins contemplated by this disclosure are those secreted via the Sec-dependent pathway. Sec-dependent effector (SDE), as used herein, refers to any bacterial effector protein secreted from a bacterium via the Sec-dependent pathway. Pathogenic *Ca. Liberibacter* species secrete SDEs into the phloem of host plants, such as citrus and solanaceous crops. As used herein, the terms "solanaceous crop" or "solanaceous plant" are used interchangeably and are directed plants of the Solanacea family including tomato (*Solanum lycopersicum* and *Solanum pennelli*); potato (*Solanum tuberosum*); eggplant (*Solanum melongena*), bell/chili peppers (*Capsicum annuum, Capsicum baccatum*, and *Capsicum chinense*). These SDEs interact with endogenous proteins and nucleic acids in the phloem and companion cells, disrupting normal physiology and inducing the symptoms of HLB in citrus. Moreover, this same interaction can occur with SDEs related to *Ca. Liberibacter* species (e.g. *Ca. Liberibacter solanacearum*, 'CLso') infection in solanaceous crops such as tomato, pepper eggplant, tamarillo and potato (e.g. zebra chips).

Here we show that one of these secreted proteins, SDE15 also known as Las4025, targets a well-known negative regulator of plant programmed cell death (PCD) to promote infection. Las4025 could be detected in the phloem sap of Las-infected plants. Transgenic expression of Las4025 in citrus promotes Las multiplication and HLB symptom development. SDE15 suppresses not only PCD induced by *Xanthomonas citri* subsp. *citri* (Xcc) in citrus, but also PCD induced by AvrBsT (a PCD-eliciting *Xanthomonas* effector) in tobacco, suggesting that Las4025 is a broad-spectrum bacterial suppressor of plant PCD. Yeast two-hybrid, in vitro protein pull-down and in vivo bimolecular fluorescence complementation assays showed that SDE15 interacts with ACD2 (ACCELERATED CELL DEATH 2), a repressor of plant PCD and that it enhances the red chlorophyll catabolite reductase (RCCR) activity of ACD2 to remove porphyrin-related molecules, accumulation of which causes PCD. Las4025 promotes the chlorophyll break-down in planta and contributes to the development of yellowing symptom associated with HLB. Characterization of Las4025 unravels an elusive aspect of the mechanism of a major plant disease.

In some embodiments, a modified plant no longer expresses endogenous molecules, for example, polypeptides and nucleic acids, capable of interacting with *Ca. Liberibacter* SDEs. In specific embodiments, the SDEs are those secreted by Las. In more specific embodiments, an Las SDE is selected from CLIBASIA_04025 (Las4025), CLIBASIA_00470 (Las470), CLIBASIA_04065 (Las4065), CLIBASIA_05150 (Las5150), and CLIBASIA_04250 (Las4250), which are encoded by the cDNA sequences corresponding to SEQ ID NOs:2-6.

In other embodiments, a modified plant no longer expresses an endogenous molecule, for example, a polypeptide or nucleic acid, capable of interacting with a *Ca. Liberibacter* Sec-dependent effector (SDE). A susceptibility protein or S-protein, as used herein, refers to an endogenous host polypeptide targeted by an SDE. A susceptibility gene or S-gene, as used herein, refers to an endogenous host gene encoding an S-protein. An S-protein-SDE complex, as used herein refers to an S-protein interacting with an SDE. An S-protein-SDE interaction, as used herein refers to a protein-protein interaction between an S-protein and an SDE. In some embodiments, an S-gene is modified such that the encoded S-protein is no longer capable of interacting with an SDE. In other embodiments, an S-gene is modified such that the encoded S-protein may interact with an SDE, but not disrupt normal physiology to an extent that a deleterious mechanism of action is triggered, for a non-limiting example, a modified S-gene that promotes proteasomal degradation of an SDE-S-protein complex before the complex activates a deleterious mechanism of action. In specific embodiments, an S-protein is selected from the group consisting of [accession numbers for citrus provided in parentheses for each S-protein group] PP2-B2/12 (orange1.1t04174), Lectin (orange1.1t05126), Cysteine protease (Cs4g07410), Cysteine protease 15A-like (Cs3g25530), Papain-like cysteine proteases, Myb family transcription factor (orange1.1t02260), YLS9-like (Cs2g29120), Cell death suppressor protein Lls1 (Cs9g02990.1), Acd1-Like Cs9g03000, Acd1 Cs8g15480, accelerated cell death 2 (ACD2) protein (AT4G37000.1, Cs1g22670), red chlorophyll catabolite reductase-like (Cs1g22680), NDR1/HIN1-like protein 13 (Cs8g01640), PHL5-like (Cs7g01290), and PHL5 (orange1.1t02259), for which cDNA examples of the citrus versions are encoded by the cDNA sequences corresponding to SEQ ID NOs:7-29 and SEQ ID NO:31. Potato orthologs are encoded by SEQ ID Nos 39-51. Provided below in Table 1 are accession numbers for select citrus S-protein sequences and S-genes encoding such S-proteins, as well as orthologs in solanaceous plants, that may be modified as taught herein (Cs or orange1=gene id (citrus genome database citrusgenomedb.org); NC or NW=genome sequence (NCBI database); XM=cDNA accession no. (NCBI database); LOC=gene accession no (NCBI database); and XP, NP, PHT or PHU=polypeptide accession no. (NCBI database)):

TABLE 1

| Species | Myb family transcription | Cell death suppressor protein Lls1 | ACD2 | Lectin |
|---|---|---|---|---|
| *Citrus sinensis* | 1. orange1.1t02260<br>LOC102621262<br>XM_025093288<br>XP_024949056<br>NW_006257094.1<br>(602674 . . . 604650)<br>2. XP_024949055<br>3. orange1.1t02259<br>LOC102608693<br>XM_015525401<br>XP_015380887<br>NW_006257094.1<br>(597073 . . . 599506)<br>4. LOC102608059<br>XM_015531655<br>XP_015387141<br>5.XP_015380888.1 | 1. Cs9g02990.1<br>LOC102615553<br>XM_006488849<br>XP_006488912<br>NC_023054.1<br>(1382910 . . . 1386383)<br>2. Cs9g03000<br>XM_006488848<br>LOC102615272<br>XP_006488911<br>NC_023054.1<br>(1390097 . . . 1395026)<br>3. Cs8g15480,<br>XM_006487933<br>XP_006487996<br>NC_023053.1<br>(18675482 . . . 18679902) | 1. Cs1g22680<br>XM_006466545<br>LOC102623285<br>XP_006466608<br>NC_023046.1<br>(25356426 . . . 25358668)<br>2. Cs1g22670<br>NC_023046.1<br>XM_006466544<br>(LOC102622999)<br>XP_006466607<br>NC_023046.1<br>(25352463 . . . 25354069) | 1. orange1.1t05126<br>LOC102630138<br>XM_006495169<br>XP_006495232<br>NW_006257465.1<br>(8465 . . . 9844)<br>2. LOC107177625<br>XM_015531689<br>XP_015387175<br>3. XP_015387176<br>LOC107177626<br>4. XP_015387172<br>LOC107177622<br>6. XP_006475932<br>LOC102628131<br>7. XP_015387174,<br>LOC107177624 |
| *Capsicum annuum* | LOC107843940,<br>XP_016543872,<br>XP_016543873,<br>XP_016576061,<br>PHT77744,<br>XP_016576060,<br>XP_016565589,<br>PHT82561,<br>XP_016565591,<br>XP_016573871,<br>XP_016544890,<br>PHT71362 | PHT80565,<br>XP_016571811,<br>XP_016571812,<br>XP_016571813 | LOC107868112,<br>PHT83236,<br>XP_16570190,<br>NP_001311893,<br>XP_016557361 | PHT71355,<br>PHT71353 |
| *Capsicum baccatum* | PHT37283,<br>PHT44431,<br>PHT52438,<br>PHT48923,<br>PHT33349,<br>PHT60401,<br>PHT39991 | PHT54548,<br>PHT54549,<br>PHT33802,<br>PHT33064,<br>PHT45532 | PHT50387,<br>PHT58680 | PHT37058 |
| *Capsicum chinense* | PHU06047,<br>PHU13451,<br>PHU22243,<br>PHU18686,<br>PHU05798 | PHU16680,<br>PHU16678,<br>PHU16679,<br>PHU03790,<br>PHU02689,<br>PHU01515 | PHU19541 | PHT99312,<br>PHU_05788 |
| *Solanum lycoperiscum* | 1. LOC101251632<br>NC_015447.3<br>(60577349 . . . 60580659<br>complement) | 1. LOC101255583,<br>NC_015441.3<br>(11974361 . . . 11979604)<br>XP_004237332,<br>AAL32300,<br>NP_001234535 | 1. LOC778267<br>NC_015440.3<br>(9353792 . . . 9357403) | N/a |
| *Solanum pennelli* | LOC107032497(XP_015089588),<br>XP_015088029,<br>XP_015088022,<br>XP_015078237,<br>XP_015078236,<br>XP_015076100,<br>XP_015072629,<br>XP_015055275 | XP_015073606,<br>XP_015058211,<br>XP_015072446 | LOC107014711,<br>XP_015070234 | N/a |
| *Solanum tuberosum* | 1. LOC102578723<br>NW_006239309.1<br>(222724 . . . 226103) | 1. LOC102597185<br>NW_006239415.1<br>(360276 . . . 368064)<br>2. LOC102604461<br>NW_006238942.1<br>(19429 . . . 23712) | 1. LOC102591737,<br>NW_006239292.1<br>(123266 . . . 127905<br>complement)<br>NP_001305541 | N/a |

TABLE 1-continued

| Species | Cysteine protease | PP2-B12 | YLS9-like |
|---|---|---|---|
| *Citrus sinensis* | 1. Cs4g07410 LOC102578016 XM_006474664 NM_001288897 NP_001275826 NC_023049.1 (4697175 . . . 4700328) 2. Cs3g25530 XM_006473521 XP_006473584 LOC102608509 NC_023048.1 (27116634 . . . 27118954) | 1. orange1.1t04174 LOC102626181 XM_025094054 XP_024949822 NW_006257165.1 (68010 . . . 79424) | 1. Cs2g29120 LOC102624273 XM_006470378 XP_006470441 NC_023047.1 (28676278 . . . 28677278) 2. Cs2g29120 LOC107174220 NC_023053.1 (385414 . . . 385806 complement) |
| *Capsicum annuum* | XP_016580127, XP_016557040, PHT84613. XP_016539529, PHT90352, XP_016561024, PHT70914 | PHT66823, XP_016552209, XP_016552365, PHT66822, XP_016573353, XP_016552297, XP_016573817 | XP_016552935, XP_016561811, XP_016560224, XP_016563876, PHT87859, XP_016562568, PHT62176, PHT71162, XP_016562568 |
| *Capsicum baccatum* | PHT42963, PHT30454, PHT41774, PHT_57030, PHT_36437, PHT30404, PHT30386, PHT59073 | PHT32781, PHT32780, PHT32035, PHT39101, PHT32776, PHT32782, PHT48962 | PHT59305, PHT54760, PHT27977, PHT53910, PHT29394 PHT43389, PHT36895 |
| *Capsicum chinense* | PHU11729, PHU20763, PHU10453, PHU27226, PHU05443 | PHU01437, PHU01440, PHU00690, PHU21394, PHU01435, PHU18677, PHT98988, PHU10308 | PHU29409, PHU24981, PHT98447, PHU24513, PHU12324, BAD11071 |
| *Solanum lycoperiscum* | 1. LOC101252505 NC_015444.3 (54626241 . . . 54628525 complement) | XP_004239687, XP_004253004, XP_004237494, XP_004237583, XP_010314855, XP_004252380 | 1. LOC101250915 NC_015438.3 (3106210 . . . 3109693 complement) |
| *Solanum pennelli* | XP_015082349, XP_015081027, XP_015074247, XP_015068628, XP_015061093, XP_015058018, XP_015063485, XP_015069437 | XP_015074926, XP_015071726, XP_015059542, XP_015073190, XP_01505954, XP_015084179, XP_015060715 | XP_015084054, XP_015086729, XP_015065001, XP_015067199, XP_015070124, XP_015081836 |
| *Solanum tuberosum* | 1. LOC102578939 NW_006238961.1 (2218619 . . . 2220963 complement) | XP_006349935, XP_006345814, XP_006340500, XP_006366161, XP_015165222, XP_006344703, XP_006361502, XP_006351708 | 1. LOC102602250 NW_006238997.1 (685210 . . . 686001 complement) |

This disclosure also contemplates all embodiments in which a genetic modification anywhere in the genome disrupts an S-protein-SDE interaction from activating a deleterious mechanism of action. In some embodiments, an S-gene or a regulatory element thereof is modified. In some embodiments, a modification may be made elsewhere in the genome, but ultimately disrupts an S-protein-SDE interaction, for a non-limiting example, inserting genetic material encoding a polypeptide capable of disrupting an S-protein-SDE interaction anywhere in the genome. In specific embodiments, an SDE is secreted the *Ca. Liberibacter* species selected from the group consisting of Las, Laf, and Lam. In some specific embodiments, the SDEs are CLIBASIA_0402 (Las4025), CLIBASIA_00470 (Las470), CLIBASIA_04065 (Las4065), CLIBASIA_05150 (Las5150), and CLIBASIA_04250 (Las4250). In specific embodiments, an S-protein is selected from the group consisting of PP2-B2/12 (orange1.1t04174), Lectin (orange1.1t05126), Cysteine protease (Cs4g07410), Cysteine protease 15A-like (Cs3g25530), Papain-like cysteine proteases, Myb family transcription factor (orange1.1t02260), YLS9-like (Cs2g29120), Cell death suppressor protein Lls1(Cs9g02990.1), Acd1-Like Cs9g03000, Acd1 Cs8g15480, accelerated cell death 2 (ACD2) protein (AT4G37000.1, Cs1g22670), red chlorophyll catabolite reductase-like (Cs1g22680), NDR1/HIN1-like protein 13 (Cs8g01640), PHL5-like (Cs7g01290), and PHL5 (orange1.1t02259).

In some cases, a modification is conducted at a target sequence as set forth in Table 1, or at a target sequence that is at least 95 percent (e.g., at least 96 percent, at least 97 percent, at least 98 percent, or at least 99 percent) identical to the sequence set forth in Table 1. In a more specific example, a modification is conducted at a target sequence set forth in SEQ ID Nos 7-38 or 39-51, or at a target sequence that is at least 95 percent (e.g., at least 96 percent, at least 97 percent, at least 98 percent, or at least 99 percent) identical to a sequence set forth in SEQ ID Nos 7-38 or 39-51.

The percent sequence identity between a particular nucleic acid or amino acid sequence and a sequence referenced by a particular sequence identification number may be determined by techniques known in the art. In one example, sequence identity is determined as follows. First, a nucleic acid or amino acid sequence is compared to the sequence set forth in a particular sequence identification number using the BLAST 2 Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the B12 seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences. the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C: \B12seq c:\seq1.txt-j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq2.txt-j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:8), or by an articulated length (e.g., 100 consecutive nucleotides or amino acid residues from a sequence set forth in an identified sequence), followed by multiplying the resulting value by 100. For example, a nucleic acid sequence that has 1200 matches when aligned with the sequence set forth in SEQ ID NO:8 is 83.7 percent identical to the sequence set forth in SEQ ID NO:1 (i.e., 1200÷1434×100=83.7). It is noted that the percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. It also is noted that the length value will always be an integer.

The embodiments described herein are not limited to a particular citrus or solanaceous plant or variety but rather encompass any citrus or solanaceous plant or hybrid thereof that may be useful in accordance with the disclosure. Citrus varieties contemplated by this disclosure include, but are not limited to, cultivated citrus types such as sweet orange, bitter orange, blood orange, grapefruit, pomelo, citron, clementine, naval orange, lemon, lime, mandarin, tangerine, tangelo, or the like.

I. Genome Editing

Certain aspects of the present disclosure relate to methods of modifying the genome of a citrus or solanaceous plant using genome editing techniques. As used herein, "genome editing" and "genome-engineering" are terms used interchangeably and refer to the modification of a genome through mutagenesis. For example, in plant genome engineering. endonucleases may be used to generate double-strand DNA breaks (DSBs) and activate genome repair pathways. These DSB repair pathways may repair the break cleanly, i.e., without altering the starting sequence, or, alternatively, induce a mutation through an error in repair. In some embodiments, genome editing is used to insert, delete, or substitute one or more base pairs at one or any combination of genetic loci. In some embodiments, a genome editing technique is used to create a mutation, for example, a point mutation or single nucleotide polymorphism.

In some embodiments the DSB repair pathway is non-homologous end-joining (NHEJ) or microhomology mediated end joining (MMEJ). During NHEJ, any nucleotide overhangs on the break ends are either resected or filled to form blunt ends that are ligated. During MMEJ, the break ends are processed to reveal overhangs comprising microhomology sequences that are then ligated together. The insertions or deletions resulting from the terminal end processing in both the NHEJ and MMEJ pathways can be referred to as indels. In some embodiments, the NHEJ or MHEJ that occurs can be relied upon to introduce a genome modification including, but not limited to, a silent mutation, a neutral mutation, a missense mutation, a nonsense mutation, or a frameshift mutation.

In other embodiments, the DSB repair pathway is homologous recombination (HR). During HR, a DSB is repaired using a template with sequences with homology to the DNA flanking the break, i.e., a homologous chromosome. In plant genome editing, a linear DNA polynucleotide flanked by sequences (e.g., of 50 base pairs or more) homologous to those flanking a targeted genomic locus, may be introduced into the genome when a DSB is repaired by HR. In some embodiments, this approach is used to introduce, substitute, or delete a DNA sequence at a genomic locus. Any DNA sequence of interest may be introduced, deleted, or substituted. An introduced or substituted DNA sequence may encode an RNA molecule with a specific activity or function, a DNA molecule with a specific activity or function (e.g., encoding a polypeptide, representing a detectable marker, etc.), a DNA molecule comprising cis-regulatory elements, or a DNA molecule encoding a polypeptide, a motif thereof, or domain thereof. In some embodiments, the nucleic acid encoding the linear DNA sequence that will act as the HR template is encoded by an expression vector. In some embodiments, the nucleic acid encoding the linear DNA sequence of interest is encoded by a DNA sequence separate from the expression vector. For example, and without limitation, the nucleic acid encoding a DNA sequence of interest may be a linear DNA polynucleotide that is co-transformed with an expression vector.

In some embodiments, single-strand breaks or "nicks" are introduced into the target DNA sequence. As used herein, the term "single-strand break inducing agent" or "nickase" refers to any agent that can induce a single-strand break (SSB) in a DNA molecule. In some embodiments two SSBs are introduced into the target DNA to generate a DSB. These breaks may also be repaired by HR, NHEJ, or MMEJ. In some embodiments, sequence modifications occur at or near the SSB sites, which can include deletions or insertions that result in modification of the nucleic acid sequence, or integration of exogenous nucleic acids by HR or NHEJ.

In one aspect, a "modification" comprises the insertion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In another aspect, a "modification" comprises the deletion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In a further aspect, a "modification" comprises the inversion of at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the substitution of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the substitution of an "A" for a "C," "G" or "T" in a nucleic acid sequence. In some embodiments, a "modification" comprises the substitution of an "C" for an "A," "G" or "T" in a nucleic acid sequence. In some embodiments, a "modification" comprises the substitution of a "G" for an "A," "C" or "T" in a nucleic acid sequence. In some embodiments, a "modification" comprises the substitution of a "T" for an "A," "C" or "G" in a nucleic acid sequence. In some embodiments, a "modification" comprises the substitution of a "C" for an "U" in a nucleic acid sequence. In some embodiments, a "modification" comprises the substitution of a "G" for an "A" in a nucleic acid sequence. In some embodiments, a "modification" comprises the substitution of an "A" for a "G" in a nucleic acid sequence. In some embodiments, a "modification" comprises the substitution of a "T" for a "C" in a nucleic acid sequence.

In some embodiments, genome editing of a citrus plant as described herein may encompass techniques that employ methods of targeting endonucleases to one or more genetic loci. In some embodiments, synthetic polypeptides, for example, Transcription Activator-Like Effectors (TALEs) and zinc fingers (ZFs), or nucleic acids, for example, Clustered Regularly Interspaced Short Palindromic Repeats/Cas (CRISPR/CAS) single guide RNAs or NgAgo (Argonaute) single strand DNAs, are used to target endonucleases to any genomic locus. The targeted endonucleases may catalyze a DSB at a target locus. Upon detecting these breaks, a cell may initiate any DSB repair pathway. In some embodiments, genome editing is carried out at more than one genomic locus simultaneously (i.e., multiplex genome engineering). In some embodiments, multiplex genome engineering may be used to remove a sequence of any size from the genome. In some embodiments, any combination and number of endonuclease targeting techniques may be used to target one or more genetic loci.

A. RNA- and DNA-Guided Genome Editing Systems

In some embodiments, genome engineering of a citrus plant as described herein may employ RNA-guided endonucleases including, but not limited to CRISPR/Cas systems. CRISPR/Cas systems have been described in U.S. Patent Application Publication Nos. 2017/0191082 and 2017/0106025, each of which are incorporated herein by reference in their entirety. In some embodiments, a targeted genome modification as described herein comprises the use of at least one, at least two, at least three, at least four, at least five, at least six, at least seven, at least eight, at least nine, or at least ten RNA-guided nucleases. In some embodiments, a CRISPR/Cas9 system, a CRISPR/Cpf1 system, a CRISPR/CasX system, or a CRISPR/CasY system are alternatives that may be used to generate modifications to target sequences as described herein.

The CRISPR systems are based on RNA-guided endonucleases that use complementary base pairing to recognize DNA sequences at target sites. CRISPR/Cas systems are part of the adaptive immune system of bacteria and archaea, protecting them against invading DNA, such as viral DNA, by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA.

A prerequisite for cleavage is the presence of a conserved protospacer-adjacent motif (PAM) downstream of the target DNA, which usually has the sequence 5'-NGG-3' but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA. Specificity of the CRISPR/Cas system is based on an RNA-guide that use complementary base pairing to recognize target DNA sequences. In some embodiments, the site-specific genome modification enzyme is a CRISPR/Cas system. In an aspect, a site-specific genome modification enzyme provided herein can comprise any RNA-guided Cas endonuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof); and, optionally, the guide RNA necessary for targeting the respective nucleases.

In some embodiments, an RNA-guided endonuclease is the DNA cleavage domain of a restriction enzyme fused to a deactivated Cas9 (dCas9), for example dCas9-Fok1. As used herein, a "dCas9" refers to a endonuclease protein with one or more amino acid mutations that result in a Cas9 protein without endonuclease activity, but retaining RNA-guided site-specific DNA binding. As used herein, a "dCas9-restriction enzyme fusion protein" is a dCas9 with a protein fused to the dCas9 in such a manner that the restriction enzyme is catalytically active on the DNA.

In some embodiments, genome editing of a citrus or solanaceous plant as described herein may employ DNA-guided endonucleases including, but not limited to, NgAgo systems.

In one aspect, a method and/or composition provided herein comprises one or more, two or more, three or more, four or more, or five or more guide RNAs or DNAs. In another aspect, a CRISPR/CAS system, dCas9-restriction enzyme fusion protein, NgAgo system provided herein is capable of generating a targeted DSB in a target sequence as described herein. In one aspect, vectors comprising nucleic acids encoding one or more, two or more, three or more, four or more, or five or more guide RNAs or DNAs and the corresponding CRISPR/CAS system, dCas9-restriction enzyme fusion protein, NgAgo system are provided to a cell by transformation methods known in the art (e.g., without being limiting, viral transfection, particle bombardment, PEG-mediated protoplast transfection or *Agrobacterium*-mediated transformation).

B. Transcription Activator-Like Effector Nucleases

In some embodiments, genome editing of a citrus plant as described herein may employ Transcription Activator-Like Effector Nucleases (TALENs). TALENs have been described in U.S. Patent Application Publication Nos. 2016/0369301 and 2015/0203871 (both of which are incorporated herein by reference in their entirety) and are well known in the art. TALENs are artificial restriction enzymes generated by fusing the transcription activator-like effector (TALE) DNA binding domain to an endonuclease domain. In one aspect, the nuclease is selected from a group consisting of PvuII, MutH, TevI and FokI, AlwI, MlyI, SbfI, SdaI, StsI, CleDORF, Clo051, Pept071. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

TALEs can be engineered to bind practically any DNA sequence, such as a target sequence as described herein. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

In one aspect, a method and/or composition provided herein comprises one or more, two or more, three or more, four or more, or five or more TALENs. In another aspect, a TALEN provided herein is capable of generating a targeted DSB in a target sequence as described herein. In one aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

C. Zinc Finger Nucleases

In some embodiments, genome engineering of a citrus or solanaceous plant as described herein may employ Zinc Finger Nucleases (ZFNs). ZFNs have been described in U.S. Pat. No. 9,322,006 (incorporated herein by reference in its entirety) and are well known in the art. ZFNs are synthetic proteins consisting of an engineered zinc finger DNA-binding domain fused to the cleavage domain of an endonuclease, for example, Fok1. ZFNs can be designed to cleave almost any long stretch of double-stranded DNA by the modification of the zinc finger DNA-binding domain. ZFNs form dimers from monomers composed of a non-specific DNA cleavage domain of FokI nuclease fused to a zinc finger array engineered to bind a target DNA sequence. The DNA-binding domain of a ZFN is typically composed of 3-4 zinc-finger arrays. The amino acids at positions −1, +2, +3, and +6 relative to the start of the zinc finger co-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art. The FokI nuclease domain requires dimerization to cleave DNA and therefore two ZFNs with their C-terminal regions are needed to bind opposite DNA strands of the cleavage site (separated by 5-7 nt). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

Several embodiments relate to a method and/or composition provided herein comprising one or more, two or more, three or more, four or more, or five or more ZFNs directed to a target sequence as described herein. In another aspect, a ZFN provided herein is capable of generating a targeted DSB. In one aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

D. Meganucleases

In some embodiments, genome engineering of a citrus or solanaceous plant as described herein may employ a meganuclease. Meganucleases, which are commonly identified in microbes, are unique enzymes with high activity and long recognition sequences (>14 nt) resulting in site-specific digestion of target DNA. Engineered versions of naturally occurring meganucleases typically have extended DNA recognition sequences (for example, 14 to 40 nt). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In one aspect, a method and/or composition provided herein comprises one or more, two or more, three or more, four or more, or five or more meganucleases directed to a target sequence as described herein. In some embodiments, a meganuclease provided herein is capable of generating a targeted DSB. In some embodiments, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

II. Site-Specific Genome Modification

Certain aspects of the present disclosure relate to methods of modifying the genome of a citrus plant using site-specific genome modification techniques. In some embodiments, site-specific genome modification of a citrus plant as described herein may employ any site-specific genome modification enzyme. As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme is a recombinase. In some embodiments, a site-specific genome modification enzyme is a transposase. In the present disclosure, site-specific genome modification enzymes include, but are not limited to, nucleases, endonucleases, recombinases, invertases, transposases, methytransferase, demethlylases, aminases, deaminases, helicases, and any combination thereof.

In some embodiments, the site-specific genome modification enzyme is a recombinase. Non-limiting examples of recombinases include a tyrosine and serine recombinases and coupled with a DNA recognition motifs, for example, a Cre recombinase, a Gin recombinase, a Flp recombinase, and a Tnp1 recombinase. In another aspect, a serine recombinase coupled with a DNA recognition motif, for example, a PhiC31 integrase, an R4 integrase, and a TP-901 integrase. In an aspect, a recombinase is tethered to a zinc-finger DNA-binding domain, or a TALE DNA-binding domain, or a Cas9 nuclease.

The Flp-FRT site-directed recombination system comes from the 2μ plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites.

Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, the site-specific genome modification enzyme is a dCas9-recombinase fusion protein. As used herein, a "dCas9-recombinase fusion protein" is a dCas9 with a protein fused to the dCas9 in such a manner that the recombinase is catalytically active on the DNA. In some embodiments, dCas9 may be fused with the catalytic domain of any enzyme such that the catalytic domain is catalytically active on DNA. In another aspect, a DNA transposase is attached to a DNA binding domain for example, a TALE-piggyBac and TALE-Mutator.

Several embodiments relate to promoting DNA recombination by providing a site-specific genome modification enzyme to a plant cell. In some embodiments, recombination is promoted by providing a strand separation inducing reagent. In one aspect, the site-specific genome modification enzyme is selected from an endonuclease, a recombinase, an invertase, a transposase, a helicase or any combination thereof. In some embodiments, recombination occurs between B chromosomes. In some embodiments, recombination occurs between a B chromosome and an A chromosome.

Several embodiments relate to promoting integration of one or more DNAs of interest by providing a site-specific genome modification enzyme. In some embodiments, integration of one or more DNAs of interest is promoted by providing a strand separation inducing reagent. In one aspect, the site-specific genome modification enzyme is selected from an endonuclease, a recombinase, a transposase, a helicase or any combination thereof. Any DNA sequence can be integrated into a target site of a chromosome sequence by introducing the DNA sequence and the provided site-specific genome modification enzymes. Any method provided herein can utilize any site-specific genome modification enzyme provided herein.

Several embodiments relate to a method and/or a composition provided herein comprising at least one, at least two, at least three, at least four, at least five, at least six, at least seven, at least eight, at least nine, or at least ten site-specific genome modification enzymes. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific genome modification enzymes.

III. Plant Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. In some embodiments, a viral vector based on a plant virus such as a Citrus Tristeza Virus may be used in accordance with the disclosure. It is contemplated that utilization of cloning systems with large insert capacities will allow introduction of large genetic sequences comprising more than one selected gene. In accordance with the disclosure, this could be used to introduce genetic material corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes that have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant genetically modified cells resulting in a screenable or selectable trait and/or will impart an improved phenotype to the resulting genetically modified plant. However, this may not always be the case, and the present disclosure also encompasses genetically modified plants incorporating non-expressed transgenes.

In accordance with the disclosure, a nucleic acid vector comprising a coding sequence may be introduced into a plant such as a citrus tree or variety, such that, when the vector is transformed into a citrus variety or plant as described herein, the coding sequence is expressed in the plant. In some embodiments the coding sequence may be expressed in, for example, the phloem or roots of the plant, or any other part of the plant. Expression of the coding sequence in the resulting genetically modified citrus tree or variety results in the tree exhibiting increased tolerance or resistance to HLB when compared to a tree lacking expression of the coding sequence.

A. Proteins and Recombinant DNA Molecules

As used herein, a "protein/Coding DNA molecule" or "polypeptide/Coding DNA molecule" refers to a DNA molecule comprising a nucleotide sequence that encodes a protein or polypeptide. A "coding sequence" or "protein/Coding sequence" or "polypeptide/Coding sequence" means a DNA sequence that encodes a protein or polypeptide. A "sequence" means a sequential arrangement of nucleotides or amino acids. The boundaries of a protein/Coding sequence or polypeptide/Coding sequence are usually determined by a translation start codon at the 5'-terminus and a translation stop codon at the 3'-terminus. A protein/Coding molecule or polypeptide/Coding molecule may comprise a DNA sequence encoding a protein or polypeptide sequence. As used herein, "transgene expression," "expressing a transgene," "protein expression," "polypeptide expression," "expressing a protein," and "expressing a polypeptide" mean the production of a protein or polypeptide through the process of transcribing a DNA molecule into messenger RNA (mRNA) and translating the mRNA into polypeptide chains, which may be ultimately folded into proteins. A protein/Coding DNA molecule or polypeptide/Coding DNA molecule may be operably linked to a heterologous promoter in a DNA construct for use in expressing the protein or polypeptide in a cell transformed with the recombinant DNA molecule. As used herein, "operably linked" means two DNA molecules linked in manner so that one may affect the function of the other. Operably-linked DNA molecules may be part of a single contiguous molecule and may or may not be adjacent. For example, a promoter is operably linked with a protein/Coding DNA molecule or polypeptide/Coding DNA molecule in a DNA construct where the two DNA molecules are so arranged that the promoter may affect the expression of the transgene.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of genome modification, that is the introduction of heterologous DNA into a host cell, in order to produce genetically modified plants and cells, and as such may also be contained in the plastid DNA or genomic DNA of a genetically modified plant, seed, cell, or plant part. As used herein, a "vector" means any recombinant DNA molecule that may be used for the purpose of genetically modifying a plant or plant cell. Recombinant DNA molecules as set forth in the sequence listing, can, for example, be inserted into a vector as part of a construct having the recombinant DNA molecule operably linked to a promoter that functions in a plant to drive expression of the protein encoded by the recombinant DNA molecule. Methods for constructing DNA constructs and vectors are well known in the art. The components for a DNA construct, or a vector comprising a DNA construct, generally include, but are not limited to, one or more of the following: a suitable promoter for the expression of an operably linked DNA, an operably linked protein/Coding DNA molecule, and a 3' untranslated region (3'-UTR). Promoters useful in practicing the present disclosure include those that function in a plant for expression of an operably linked polynucleotide. Such promoters are varied and well known in the art and include those that are inducible, viral, synthetic, constitutive, temporally regulated, spatially regulated, and/or spatio-temporally regulated. Additional optional components include, but are not limited to, one or more of the following elements: 5'-UTR, enhancer, leader, cis-acting element, intron, chloroplast transit peptides (CTP), and one or more selectable marker transgenes.

Recombinant DNA molecules of the present disclosure may be synthesized and modified by methods known in the art, either completely or in part, especially where it is desirable to provide sequences useful for DNA manipulation (such as restriction enzyme recognition sites or recombination-based cloning sites), plant-preferred sequences (such as plant/Codon usage or Kozak consensus sequences), or sequences useful for DNA construct design (such as spacer or linker sequences). The present disclosure includes recombinant DNA molecules and proteins having at least about 80% (percent) sequence identity, about 81% sequence identity, about 82% sequence identity, about 83% sequence identity, about 84% sequence identity, about 85% sequence identity, about 86% sequence identity, about 87% sequence identity, about 88% sequence identity, about 89% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, about 99% sequence identity, or about 100% sequence identity to a coding sequence provided herein, for instance the sequences set forth as SEQ ID NOs: 2-9-11-51. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar, Inc., Madison, Wis.), and MUSCLE (version 3.6) (Edgar, *Nucl. Acids Res.* 32:1792-1797, 2004) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

Proteins in accordance with the disclosure may be produced by changing (that is, modifying) a wild-type protein to produce a new protein with a novel combination of useful protein characteristics, such as altered Vmax, Km, substrate specificity, substrate selectivity, and protein stability. Modifications may be made at specific amino acid positions in a protein and may be a substitution of the amino acid found at that position in nature (that is, in the wild-type protein) with a different amino acid. Proteins provided by the disclosure thus provide a new protein with one or more altered protein characteristics relative to the wild-type protein found in nature. In one embodiment of the disclosure, a protein may have altered protein characteristics such as improved or decreased activity against one or more herbicides or improved protein stability as compared to a similar wild-type protein, or any combination of such characteristics. In one embodiment, the disclosure provides a protein, and the DNA molecule or coding sequence encoding it, having at least about 80% sequence identity, about 81% sequence identity, about 82% sequence identity, about 83% sequence identity, about 84% sequence identity, about 85% sequence identity, about 86% sequence identity, about 87% sequence identity, about 88% sequence identity, about 89% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, about 99% sequence identity, or about 100% sequence identity to a protein sequence such as set forth as SEQ ID NOs: 2-9 and SEQ ID NO:11-51. Amino acid mutations may be made as a single amino acid substitution in the protein or in combination with one or more other mutation(s), such as one or more other amino acid substitution(s), deletions, or additions. Mutations may be made as described herein or by any other method known to those of skill in the art.

B. Regulatory Elements

The plants and methods of the present disclosure can utilize a vector comprising a coding sequence that, when the vector is transfected into a plant, the coding sequence is expressed in the plant. The site and conditions under which the first selected DNA is expressed can be controlled to a great extent by selecting a promoter element in the vector that causes expression under the desired conditions.

In some embodiments, the coding sequence is expressed primarily in the roots of the plant, or in the phloem tissue of the plant. In this case, the coding sequence may be expressed in a greater quantity in roots or phloem than in other tissues of the plant. In some embodiments, more than one copy of an coding sequence may be expressed in a plant such that expression in the roots or phloem may be at least twice as much as in any other individual plant tissue (e.g., leaves, flowers, etc).

Limiting expression of the coding sequence primarily to the roots or phloem of a plant may be accomplished by operably linking the coding sequence to a heterologous promoter active in plant tissues, such as a root-specific or phloem-specific promoter. In other embodiments, a constitutive promoter may be preferred such that the coding sequence is expressed in all tissues of the plant. In some embodiments, a phloem-specific promoter in accordance with the disclosure may comprise an *Arabidopsis* sucrose-proton symporter 2 (AtSUC2) promoter, or a constitutive promoter may comprise a CaMV 35S promoter. Any root-specific or phloem-specific promoter known in the art may potentially be utilized to direct expression of the coding sequence to the roots or the phloem tissue. Examples of these may include, but are not limited to, an RB7, RPE15, RPE14, RPE19, RPE29, RPE60, RPE2, RPE39, RPE61, SHR, ELG3, EXP7, EXP18 or Atlg73160 promoter (Vijaybhaskar et al., 2008; Kurata et al., 2005; PCT Publication WO 01/53502; U.S. Pat. No. 5,459,252; Cho and Cosgrove, 2002).

In some embodiments, a coding sequence as described herein may be expressed at any level in the plant such that it may be detected in the plant using techniques known in the art. A coding sequence may be expressed in a greater quantity in a genetically modified citrus plant or variety than in a plant not expressing the coding sequence as described herein. In some embodiments, the coding sequence is expressed at least twice as much as in a plant not expressing a coding sequence. In further embodiments, the coding sequence is expressed at least three, or four, or five times, or more, as much as in a plant not expressing a coding sequence. In yet another embodiment, there is no detectable expression of the coding sequence in a plant not expressing a coding sequence.

The DNA sequence between the transcription initiation site and the start of the coding sequence, i.e., the untranslated leader sequence, can also influence gene expression. One may thus wish to employ a particular leader sequence with a transformation construct of the disclosure. Useful leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure.

It is contemplated that vectors for use in accordance with the present disclosure may be constructed to include an ocs enhancer element. This element was first identified as a 16-bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

C. Terminators

Transformation constructs prepared in accordance with the disclosure will typically include a 3' end DNA sequence that acts as a signal to terminate transcription and allow for the poly-adenylation of the mRNA produced by coding sequences operably linked to a promoter. In one embodiment of the disclosure, the native terminator of a coding sequence coding sequence may be used. Alternatively, a heterologous 3' end may enhance the expression of coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

D. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a genetically modified plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

E. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Many examples of suitable marker proteins are known to the art and can be employed in the practice of the disclosure. Examples include, but not limited to, neo (Potrykus et al., 1985), bar (Hinchee et al., 1988), bxn (Stalker et al., 1988); a mutant acetolactate synthase (ALS) (European Patent Application 154, 204, 1985) a methotrexate resistant DHFR (Thillet et al., 1988), β-glucuronidase (GUS); R-locus (Dellaporta et al., 1988), β-lactamase (Sutcliffe, 1978), xylE (Zukowsky et al., 1983), α-amylase (Ikuta et al., 1990), tyrosinase (Katz et al., 1983), β-galactosidase, luciferase (lux) (Ow et al., 1986), aequorin (Prasher et al., 1985), and green fluorescent protein (Sheen et al., 1995; Haseloff et al., 1997; Reichel et al., 1996; Tian et al., 1997; WO 97/41228).

Included within the terms "selectable" or "screenable" markers also are genes which encode a "secretable marker" whose secretion can be detected as a means of identifying or selecting for genetically modified cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

IV. Antisense and RNAi Constructs

In the methods and compositions of the present disclosure, endogenous gene activity can be down-regulated by any means known in the art, including through the use of ribozymes or aptamers. Endogenous gene activity can also be down-regulated with an antisense or RNAi molecule.

In particular, constructs comprising a coding sequence, including fragments thereof, in antisense orientation, or combinations of sense and antisense orientation, may be used to decrease or effectively eliminate the expression of the gene in a plant such as a citrus tree or variety. Accordingly, this may be used to "knock-out" the function of the coding sequence or homologous sequences thereof.

Techniques for RNAi are well known in the art and are described in, for example, Lehner et al., (2004) and Downward (2004). The technique is based on the ability of double stranded RNA to direct the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense. and in some aspects RNAi, methodology takes advantage of the fact that nucleic acids tend to pair with "complementary" sequences. By complementary, it is meant that polynucleotides are those which are capable of base-pairing according to the standard Watson/Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the disclosure, such an oligonucleotide may comprise any unique portion of a nucleic acid sequence provided herein. In certain embodiments of the disclosure, such a sequence comprises at least 18, 30, 50, 75, or 100 or more contiguous nucleic acids of the nucleic acid sequence of a gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that an embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., as in a ribozyme) could be designed. Methods for selection and design of sequences that generate RNAi are well known in the art (e.g. Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

V. Methods for Genetic Transformation

Suitable methods for transformation of plant or other cells for use with the current disclosure are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into genetically modified plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Another method for delivering transforming DNA segments to plant cells in accordance with the disclosure is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force.

VI. Production and Characterization of Genetically Modified Plants

After effecting delivery of exogenous DNA to recipient cells, the next steps generally concern first identifying and selecting the transformed cells and from those cells identifying the selecting the genetically modified cells for further culturing and plant regeneration. In order to improve the ability to identify transformed and genetically modified cells, one may desire to employ one or more selectable or screenable marker genes with a transformation vector prepared in accordance with the disclosure. In this case, one would then generally assay the potentially transformed and modified cell population by exposing the cells to a selective agent or agents, or one would screen the cells for the desired marker gene trait.

It is believed that DNA is introduced into only a small percentage of target cells in any one study. In order to provide an efficient system for identification of those cells that are transformed and predisposed to genetic modification one may employ a means for selecting those cells that are stably transformed. One exemplary embodiment of such a method is to introduce, into the host cell, a marker gene which confers resistance to some normally inhibitory agent, such as an antibiotic or herbicide. Potentially transformed cells then are exposed to the selective agent. In the population of surviving cells will be those cells where, generally, the resistance/Conferring gene has been integrated and expressed at sufficient levels to permit cell survival. Cells may be tested further to confirm stable integration of the exogenous DNA.

Cells that survive the exposure to the selective agent, or cells that have been scored positive in a screening assay, may then be selected again using a second, distinct selection paradigm that detects those cells that contain the genetic modification. Cells that survive the exposure to the second selective agent, or cells that have been scored positive in the second screening assay, may be cultured in media that supports regeneration of plants. The genetically modified cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a genetically modified cell is identified, depending on the initial tissue.

To confirm the presence of the genetic modification in the regenerating plants, a variety of assays may be performed. Such assays include, for example, "molecular biological" assays, such as Southern and northern blotting and polymerase chain reaction (PCR); "biochemical" assays, such as detecting the absence or presence of a protein product, e.g., by immunological means (ELIS As and western blots) or by enzymatic function; plant part assays, such as leaf or root assays; and also, by analyzing the phenotype of the whole regenerated plant. Modification of the host genome and the independent identities of genetically modified plants may be determined using, e.g., Southern hybridization or PCR. Genetic modifications that affect, for example, protein or gene expression may then be evaluated by specifically measuring the expression of those affected molecules or evaluating the phenotypic changes brought about by their expression change.

VII. Breeding Plants of the Disclosure

In addition to direct transformation of a particular plant genotype with a construct prepared according to the current disclosure, genetically modified plants may be made by crossing a plant having a selected genetic modification of the disclosure to a second plant lacking the construct. For example, a selected lignin biosynthesis coding sequence can be introduced into a particular plant variety by crossing, without the need for ever directly transforming a plant of that given variety. Therefore, the current disclosure not only encompasses a plant directly modified or regenerated from cells which have been modified in accordance with the current disclosure, but also the progeny of such plants.

As used herein the term "progeny" denotes the offspring of any generation of a parent plant prepared in accordance with the instant disclosure, wherein the progeny comprises a selected DNA construct. "Crossing" a plant to provide a plant line having one or more added transgenes relative to a starting plant line, as disclosed herein, is defined as the techniques that result in a coding sequence of the disclosure being introduced into a plant line by crossing a starting line with a donor plant line that comprises a first selected DNA of the disclosure. To achieve this in a plant such as a citrus tree one could, for example, perform the following steps:

(a) plant seeds of the first (starting line) and second (donor plant line that comprises a first selected DNA of the disclosure) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

In some embodiments, asexual reproduction or propagation may be used to obtain a progeny plant in accordance with the disclosure. Techniques to achieve asexual propagation or reproduction in citrus trees or varieties may include, for example, grafting, budding, top-working, layering, runner division, cuttings, rooting, T-budding, and the like. In some embodiments, one citrus variety into which a coding sequence has been introduced may be grafted onto the rootstock of another variety. In other embodiments, a coding sequence may be introduced into the rootstock. In either of these situations, one or both of the plant varieties may exhibit increased tolerance or resistance to HLB.

EXAMPLES

Example 1

Identification of Las SDEs

Las has been predicted to produce at least 166 SDEs, 36 of which have been shown to be highly expressed in plants. These 36 Las SDEs were stably or transiently expressed in citrus plants and *Nicotiana benthamiana* to determine if they are HLB effectors. Transgenic expression of CLIBASIA_04025 (Las4025), CLIBASIA_00470 (Las470), CLIBASIA_04065 (Las4065), CLIBASIA_05150 (Las5150), and CLIBASIA_04250 (Las4250) induced symptoms consistent with HLB. For example, transgenic expression of CLIBASIA_04025 (Las4025) without its signal peptide stunted leaf growth, delayed plant growth, and induced leaf yellowing (FIG. 1A and FIG. 1B). The CLIBASIA_04025 expression in transgenic lines was confirmed using an antibody against CLIBASIA_04025 (FIG. 1C). Transgenic expression of CLIBASIA_00470 also delayed plant growth.

Example 2

Las SDE and Host Target Proteins Interaction Assays

Yeast two-hybrid (Y2H) screening was performed to identify putative target proteins of the SDEs identified above. A cDNA library was generated from mRNA isolated from 'Valencia' sweet orange plants infected with Las. The mRNA was obtained from these plants during the early stage of infection in which the Las Ct value was between 28-30.

The cDNA library was constructed using the Make Your Own Mate & Plate™ Library System (Clontech) following the manufacturer's instructions and had a titer greater than $3\times10^8$ cfu.

The coding sequences of CLIBASIA_04025 (Las4025), CLIBASIA_00470 (Las470), CLIBASIA_04065 (Las4065), CLIBASIA_05150 (Las5150), and CLIBASIA_04250 (Las4250), without their signal peptides, were cloned in-frame with the GAL4 DNA-binding domain (BD) of the bait vector pGBKT7. The Y2H screen was performed using the Matchmaker® Gold Yeast Two-Hybrid System (Clontech) following the manufacturer's instructions. The SDE target proteins identified in the screen are summarized in Table 1B.

TABLE 1B

Y2H-confirmed Las SDE target proteins.

| SDEs | Target proteins |
|---|---|
| CLIBASIA_04025 (Las4025) | PP2-B2/12 (orange1.1t04174) |
| | Lectin (orange1.1t05126) |
| | Cysteine protease (Cs4g07410) |
| | Cysteine protease 15A-like (Cs3g25530) |
| | Myb family transcription factor (orange1.1t02260) |
| | YLS9-like (Cs2g29120) |
| | Cell death suppressor protein Lls1(Cs9g02990) |
| | Red chlorophyll catabolite reductase; Accelerated cell death 2 (Cs1g22670) |
| | Homolog to Acd2, red chlorophyll catabolite reductase-like (Cs1g22680), which is 64% similar |
| | Homolog to Lls1 - Acd1-Like Cs9g03000, which is 93.4% similar; Acd1 Cs8g15480, which is 51% similar, but is also work in same chlorophyll catabolism pathway to Acd2. |
| | Homologs to Cysteine protease (Cs3g25530) and Cysteine Protease (Cs4g07410), all Papain-like cysteine proteases |
| | Homolog YLS9-like, NDR1/HIN1-like protein 13, Cs8g01640, which is 75% similar |
| | Homologs to Myb family transcription factor, PHL5-like, Cs7g01290, 56% similar; PHL5, orange1.1t02259, which is 76% similar |
| | Galactinol-sucrose galactosyltransferase 2 (Cs9g12460) |
| | Vacuolar protein sorting-associated protein 36 (Cs7g24050) |
| | DnaJ protein homolog (Cs7g23510) |
| | Plastid-specific ribosomal protein 4 (Cs6g08000) |
| | Pathogenesis-related protein 10 (Cs9g03630) |
| | Glucan endo-1,3-beta-D-glucosidase-like protein (orange1.1t00643) |
| | Core-2/I-branching beta-1,6-N-acetylglucosaminyltransferase family protein (Cs7g07430) |
| | Leucyl-tRNA synthetase bacterial/mitochondrial, class Ia (Cs2g02720) |
| | Annexin D1 (Cs3g18360) |
| | Pentatricopeptide repeat-containing protein (Cs5g26120) |
| | Probable fructose-bisphosphate aldolase 2, chloroplastic (Cs8g08710) |
| | Arginine/serine-rich splicing factor, putative, expressed (Cs3g18350) |
| | SVP1-like protein 2 (Cs5g32770) |
| | Alanine aminotransferase 2 (Cs7g09270) |
| | BEL1-like homeodomain protein 1 (Cs6g13660) |
| | AT-rich interactive domain-containing protein 4 (Cs4g06750) |
| | Heat shock factor protein HSF8 (Cs7g24140) |
| | Plasma membrane ATPase 1 (Cs6g03480) |
| | Gag-pol polyprotein (Cs7g14770) |
| | Phospholipid: diacylglycerol acyltransferase (Cs1g17750) |
| | Aconitate hydratase, cytoplasmic (Cs2g21430) |
| | DNA-directed RNA polymerase subunit alpha (orange1.1t03665) |
| | Polyubiquitin 10 (Cs4g11190) |
| | Diacylglycerol kinase theta (Cs4g02800) |
| | Chloroplast methionine sulfoxide reductase B2 (Cs9g05400) |
| | Leucine-rich repeat receptor protein kinase EXS (Cs7g18050) |
| | Lateral organ boundaries-domain 29 (orange1.1t00246.1) |
| | Formamidase (Cs1g21820) |
| | Signal peptidase complex subunit 3B (Cs3g13460) |
| | Probable plastid-lipid-associated protein 8 (Cs7g07440) |
| | Stress responsive gene 6 protein (orange1.1t01091) |
| | UBX domain-containing protein (Cs5g01690) |
| | Protein SRG1 (Cs5g13180) |
| | Thioredoxin H-type (Cs1g24740) |
| | Glycoside hydrolase (Cs8g12020) |
| | Thioredoxin F2 (Cs6g02830) |
| | RNA pseudourine synthase 7 (orange1.1t02625) |
| | Kunitz-type protease inhibitor KPI-D2.2 (Cs5g16850) |
| | Aspartate aminotransferase (Cs4g19830) |
| | UDP-glucuronate decarboxylase 4 (Cs6g05450) |
| | Nitrate transporter 1.5 (orange1.1t00223) |
| | FKBP-like peptidyl-prolyl cis-trans isomerase family protein (orange1.1t00062) |

TABLE 1B-continued

Y2H-confirmed Las SDE target proteins.

| SDEs | Target proteins |
| --- | --- |
| | Zinc-binding alcohol dehydrogenase domain-containing protein 2 (Cs8g05790) |
| | Mannitol dehydrogenase (Cs1g20600) |
| | RNA recognition motif family protein (Cs2g07940) |
| | alpha/beta-Hydrolases superfamily protein (Cs2g21120) |
| | Protein argonaute 1 (Cs5g16710) |
| | Progesterone 5-beta-reductase (Cs3g11840) |
| | NADH dehydrogenase [ubiquinone] 1 alpha subcomplex subunit 6 (Cs1g16240) |
| | Tetratricopeptide repeat (TPR)-like superfamily protein (Cs6g03690) |
| | Mitochondrial carrier domain-containing protein (Cs6g03800) |
| | Cell division control protein 48 homolog C (Cs3g01650) |
| | Subtilisin-like protease (Cs8g02780) |
| | U6 snRNA-associated Sm-like protein LSm6 (orange1.1t02120) |
| | Subtilisin-like protease (Cs8g06090) |
| | Histone H4 (Cs8g18120) |
| | Chromatin-associated protein Dek (Cs4g08790) |
| | Serine carboxypeptidase-like 49 (Cs7g24460) |
| | RING/U-box superfamily protein (Cs8g16720) |
| | Linoleate 13S-lipoxygenase 2-1 (orange1.1t04376) |
| | Isoflavone reductase-like (Cs2g16260) |
| | alpha-like protein (Cs6g16290.1) |
| | THO complex subunit 3 (Cs7g18110) |
| | Uncharacterized protein Sb07g024435 (Cs7g26460) |
| | Ubiquitin-activating enzyme E1 2 (Cs8g20660) |
| | Structure-specific endonuclease subunit SLX1 (Cs2g09350) |
| | Putative uncharacterized protein P0458H05.117 (Cs4g05300) |
| | Aconitate hydratase 1 (Cs1g26040) |
| | DnaJ homolog subfamily B member 13 (Cs3g04780) |
| | Plastocyanin (Cs3g26730) |
| | Putative uncharacterized protein Sb03g000880 (Cs5g31880) |
| | 50S ribosomal protein L14 (orange1.1t04817) |
| | Oligopeptidase A (Cs1g20720) |
| | Maturase K (Cs2g09070) |
| | Protein FRA10AC1 (Cs7g01730) |
| | Putative Uncharacterized protein AlNc14C124G6763 (Cs8g09030) |
| | Putative Uncharacterized protein Sb10g020525 (orange1.1t00482) |
| | Putative Uncharacterized protein OSJNBb0021O11.27 (Cs4g16820) |
| CLIBASIA_00470 (Las470) | Lectin (orange1.1t05126) |
| | Galactinol-sucrose galactosyltransferase 2-like (Cs9g12460) |
| | DnaJ homolog 1 like (Cs1g19720) |
| | YLS9-like (Cs2g29120) |
| | 8-hydroxygeraniol dehydrogenase (XM_006466284.2) |
| CLIBASIA_04065 (Las4065) | Hypothetical protein (orange1.1t00563) |
| CLIBASIA_05150 (Las5150) | Cysteine protease (Cs4g07410) |
| CLIBASIA_04250 (Las4250) | Translation initiation factor IF-3 (orange1.1g044576m) |

Figure 5:
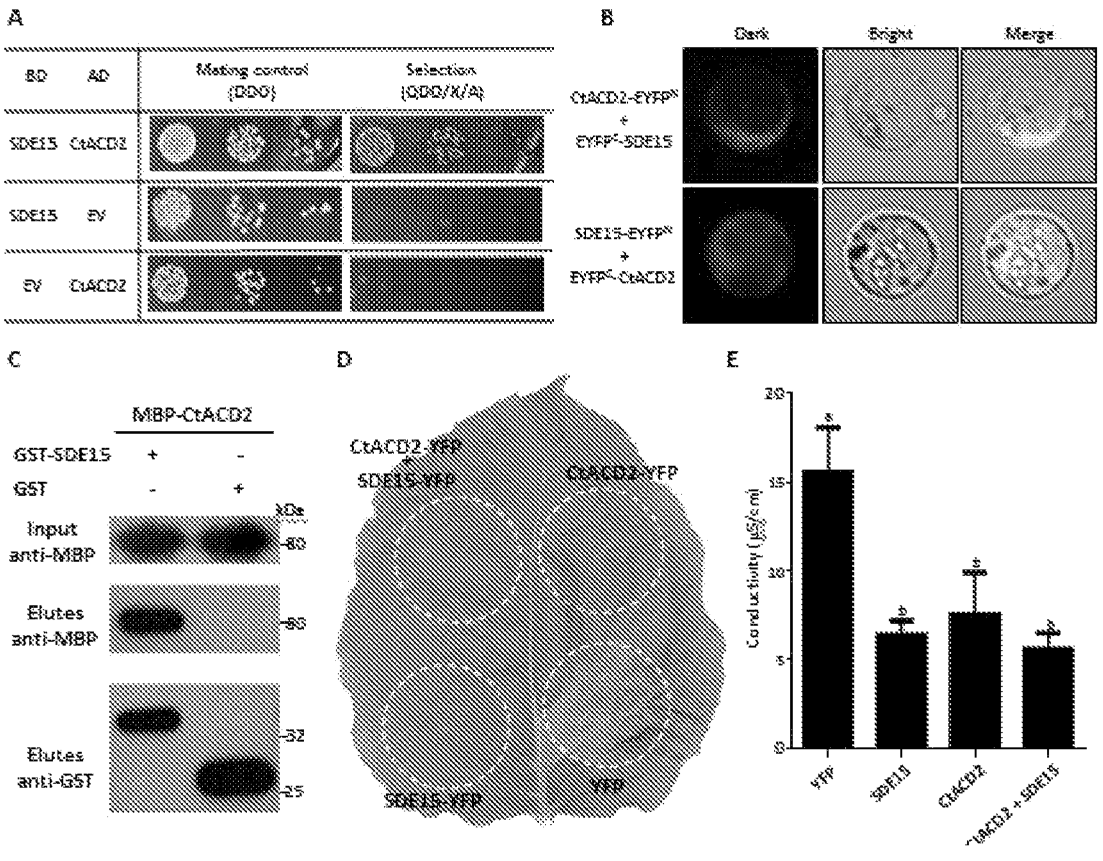
FIG. 5 shows SDE15 (identified as CLIBASIA_04025) interacts with CtACD2 protein, which negatively regulate hypersensitive reaction.

Multiple proteins interacted with CLIBASIA_04025 (Las4025) and CLIBASIA_00470 (Las470); whereas, CLIBASIA_04065 (Las4065), CLIBASIA_05150 (Las5150), and CLIBASIA_04250 (Las4250) each interacted with a single protein. CLIBASIA_04025 (Las4025) interacted with PP2-B2 (orange1.1t04174), a phloem protein. Phloem protein encoding genes are known to be involved in phloem blockage and are suggested to contribute to HLB symptom onset. In addition, SDE15 was shown to interact with the CtACD2 protein by the Y2H assay (FIG. 5A).

Figure 2:
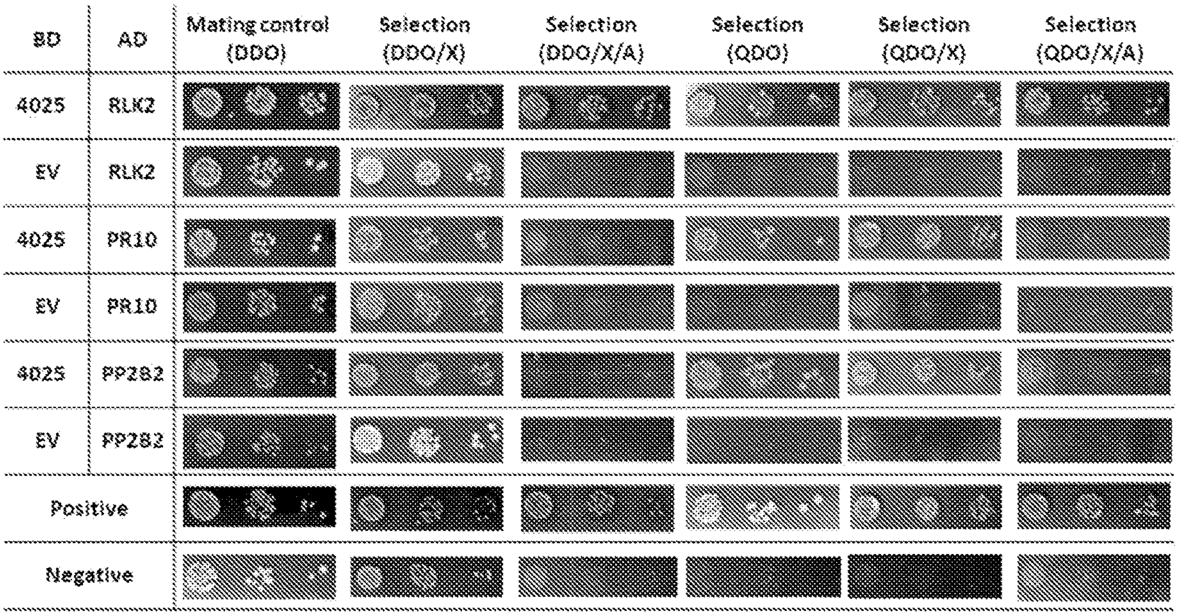
FIG. 2 shows interactions between CLIBASIA_04025 (Las4025) and targets proteins demonstrated by yeast two-hybrid assay. Yeast cells were co-transformed with GAL4 DNA-binding domain (BD) expression vector pGBKT7 and GAL4 activation domain (AD) expression vector pGADT7. The pGBKT7 vector was either empty (EV) or contained CLIBASIA_04025 (Las4025) without its signal peptide cloned in-frame with the BD; and the pGADT7 vector contained either RLK2, Pathogenesis-related protein 10 (Cs9g03630) (PR10), or PP2-B2 (orange1.1t04174) (PP2B2) cloned in-frame with the AD. The negative control was performed with empty-AD and -BD vectors, and the positive control was performed with p53-BD and T-antigen-AD vectors. Cultures of the co-transformed yeast clones were adjusted to an OD600 of 0.2 and then spotted at three dilutions (1/10, 1/100, and 1/1000) on DDO, DDO/X, DDO/X/A, QDO, QDO/X, and QDO/X/A mediums. The images were captured after 4 days of growth. SD: synthetic defined yeast minimal medium; DDO: double dropout media, SD-Leu/-Trp; QDO: quadruple dropout media, SD/-Ade/-His/-Leu/-Trp; X: X-α-Gal; and A: Aureobasidin A.

To confirm the initial Y2H screen results, full-length sequences of the SDE target proteins were cloned in-frame with the GAL4 activation domain (AD) of the prey vector pGADT7. Following the manufacturer's instructions, the Y2HGOLD yeast strain was co-transformed with relevant bait and prey vector pairs. For negative controls, a prey vector co-transformed with an empty bait vector was used. Exemplary results that were achieved in the Y2H assay using the CLIBASIA_04025 (Las4025) bait vector are shown in FIG. 2. CLIBASIA_04025 (Las4025) interacted with PP2-B2 (orange1.1t04174), and Pathogenesis-related protein 10 (Cs9g03630).

Glutathione S-transferase (GST) pull-down and Bimolecular fluorescence complementation (BiFC) assays were performed to further confirm Y2H results. Las genomic DNA was extracted from infected citrus leaves and the coding sequences of CLIBASIA_04025 (Las4025), CLIBASIA_00470 (Las470), CLIBASIA_04065 (Las4065), CLIBASIA_05150 (Las5150), and CLIBASIA_04250 (Las4250) were PCR-amplified for use in both assays. For the GST pull-down assay, the respective fragments were cloned in-frame with Maltose-binding protein (MBP) in the pMAL™/C5X vector (NEB, USA) to generate MBP-SDE fusion proteins. The coding sequences of the SDE target proteins were PCR-amplified using citrus leaf cDNA as a template. The respective fragments were cloned in-frame with GST in the pGEX-4T-1 vector (GE Healthcare, USA) to generate GST-target fusion proteins. For the BiFC assays, the coding sequences of the SDE target proteins were PCR-amplified using citrus leaf cDNA as a template. The respective SDEs and SDE target proteins were cloned in-frame with either N-terminal or C-terminal fragments of EYFP using pSAT6-nEYFP/C1 and pSAT6/CEYFP/C1-B vectors, respectively. This was done with an In-Fusion cloning kit (Clontech, USA) and produced SDE-EYFPN, EYFPC-SDE, SDE target-EYFPN, and EYFPC-SDE target fusion proteins. Citrus protoplasts isolated from grapefruit epicotyl segments were co-transformed with pairs of EYFPC and EYFPN vectors. Additionally, SDE15 was shown to interact with the CtACD2 protein by the GST pull-down assay (FIG. 5C) and the BiFC assay (FIG. 5B).

Figure 3:
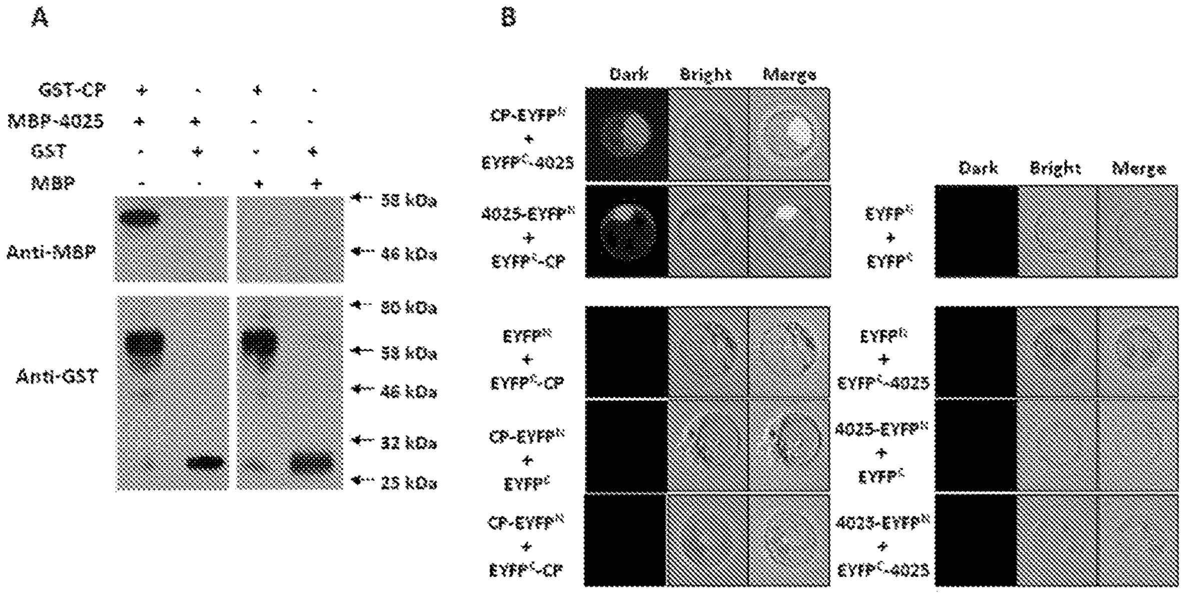
FIG. 3 shows CLIBASIA_04025 interacted with cysteine protease (Cs4g07410).

Exemplary results obtained in the GST pull-down and BiFC assays are provided in FIG. 3. In both assays, the CLIBASIA_04025 (Las4025) directly interacted with cysteine protease (Cs4g07410), therefore confirming the interaction observed between the two proteins in the Y2H assays. No interactions were detected in any of the negative controls (FIG. 3A and FIG. 3B).

SDE15 was also shown to interact with the CtACD2 protein that negatively regulates the hypersensitive reaction by the hypersensitive response (HR) assay (FIG. 5D). The electrolyte leakage associated with HR induced by AvrBsT protein is shown in FIG. 5E.

Example 3

Overexpression of SDE Target Proteins in Citrus Plants

Figure 4:
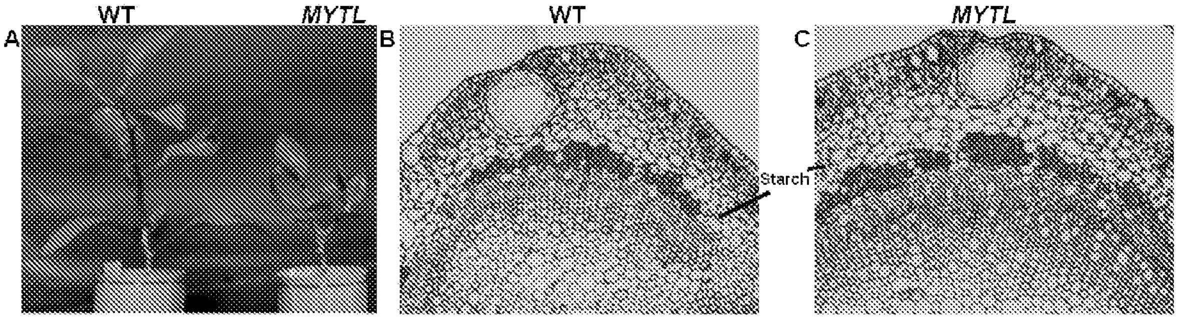
FIG. 4 shows overexpression of Myb family transcription factor (MYTL, XP_015380888.1) in Duncan grapefruit induced HLB-like symptoms.

Overexpression of Myb family transcription factor (orange1.1t02260), a CLIBASIA_04025 (Las4025) target protein, in Duncan grapefruits induced symptoms similar to those observed in citrus plants infected with *Candidatus Liberibacter asiaticus*. Plants that overexpressed MYTL displayed stunted plant growth and greater starch accumulation when compared to wild type controls (FIG. 4A, FIG. 4B, and FIG. 4C).

Example 4

Modification of Susceptibility Genes in Citrus Plants

Based on the identification of susceptibility genes that encode proteins that are targets of SDEs secreted by Las, citrus plants and regulatory elements thereof may be modified to exhibit resistance to infection by Las. In particular, plants may be modified to exhibit reduced expression of one or more of the susceptibility genes identified herein. These susceptibility genes and regulatory elements thereof may themselves be modified using targeted genome editing (e.g., single-stranded oligonucleotide-mediated genome editing, meganucleases, zinc finger nucleases, TALENs, or RNA-guided nuclease (e.g., CRISPR technology). Modified citrus plants may be produced using a plant transformation vector comprising an expression cassette comprising a promoter and 3' UTR operably linked to the coding sequence for a modified target protein. The plant transformation vector may be used with *Agrobacterium tumefaciens* and standard methods for plant transformation known in the art.

Alternatively, plants comprising modified endogenous genes or regulatory elements thereof may be produced by inserting DNA directly into the plant genome at a specified targeted location. Any site or locus within the plant genome may potentially be chosen for site-directed integration of a transgene or construct of the present disclosure. For site-directed integration, a double-strand break (DSB) or nick may first be made at a selected genomic locus with a site-specific nuclease, such as, for example, a zinc-finger nuclease, an engineered or native meganuclease, a TALE-endonuclease, or an RNA-guided endonuclease (e.g., Cas9, Cpf1, CasX or CasY). Any method known in the art for site-directed integration may be used. In the presence of a donor template molecule, the DSB or nick may then be repaired by homologous recombination between the homology arm(s) of the donor template and the plant genome, or by non-homologous end joining (NHEJ), resulting in site-directed integration of the insertion sequence into the plant genome to create the targeted insertion event at the site of the DSB or nick.

Plants having one or more mutations in the genomic susceptibility genes or regulatory elements thereof may be produced using a double-strand break (DSB) or nick made at the genomic locus with a site-specific nuclease, such as, a zinc-finger nuclease, an engineered or native meganuclease, a TALE-endonuclease, or an RNA-guided endonuclease (e.g., Cas9, Cpf1, CasX or CasY). Any method known in the art for genome editing or non-templated editing may be used. Delivery methods for the nuclease and gRNA include, but are not limited to, delivering by *Agrobacterium*-mediated methods, delivering as a protein or RNA using transfection or biolistics, and delivery by expression from a virus. One or more nucleases or gRNA may be used. Donor molecules to deliver the desired changes may include, but are not limited to, double-stranded DNA, single-stranded DNA oligonucleotides, RNA or viral DNA. Donor molecules may be delivered by *Agrobacterium*, virus, biolistic delivery, or transfection. In the presence of a donor template molecule, the one or more DSBs or nicks may then be repaired by homologous recombination between the homology arm(s) of the donor template and the plant genome, by non-homologous end joining (NHEJ), by single-strand annealing pathway or other DNA repair mechanisms resulting in modification of the native sequence in the plant genome to that contained by the donor to create the desired mutation.

Modified citrus plants may be tested for resistance to HLB. Citrus plants that are modified to exhibit reduced expression of one or more of the susceptibility genes identified herein may be inoculated with a strain from the genus *Ca. Liberibacter* and evaluated for symptoms of HLB infection compared to citrus plants that do not comprise modified susceptibility genes or regulatory elements thereof. Modified plants that test negative for HLB may be used for further greenhouse and field testing and breeding of HLB resistant citrus lines.

Example 5

Overexpression of SDE15 in *Nicotiana tabacum* and Citrus

SDE15 (CLIBASIA_04025, 11.17 kDa) is a hypothetical protein. Sequence analysis of SDE15 did not reveal any insights into its function except the presence of a typical signal peptide (amino acids 1-22) predicted by SignalP v 4.1 (FIG. 6A). Interestingly, transgenic expression of SDE15 without the signal peptide (8.68 kDa) in *N. tabacum* caused markedly reduced plant growth and a slightly yellow leaf phenotype, suggestive of biological effects of SDE15 on host biology. These interesting phenotypes, observed in a heterologous plant (*N. tabacum*), prompted us to overexpress SDE15 in the native host plant citrus (cv. Duncan grapefruit) via stable *Agrobacterium* mediated transformation to determine whether SDE15 is involved in inducing HLB-like symptoms, suppressing plant defenses and/or promoting Las growth. Indeed, SDE15-transgenic Duncan grapefruit plants showed some HLB-like symptoms including slight yellowing, smaller leaves, and reduced growth at the early stage of development (FIG. 6 B). Interestingly, these HLB-like symptoms disappeared approximately one year after transgenic plants were grown under greenhouse conditions.

Las-infected plants show characteristic gene expression patterns (Albrecht, U., and Bowman, K. (2008). PLANT SCIENCE 175, 291-306; Kim, J. S., Sagaram, U. S., Burns, J. K., Li, J. L., and Wang, N. (2009). Phytopathology 99, 50-57; Albrecht, U., and Bowman, K. D. (2012). *Plant Sci* 185-186, 118-130; Rawat, N., Kiran, S. P., Du, D., Gmitter, F. G., and Deng, Z. (2015). *BMC Plant Biol* 15, 184). To determine whether SDE15 also modulates host gene expression, we compared the expression patterns of HLB-associated marker genes in SDE15-transgenic and EV (empty vector)-transgenic citrus plants. We found that expression of the genes encoding phloem protein 2 (PP2)-B15, WRKY40, and Zn transporter 5 (ZIPS) was highly induced in SDE15-transgenic citrus, whereas expression of the genes encoding sugar transporter protein Sweet7 and Sweet15 and chalcone synthase were reduced compared to control, resembling those in HLB plants for these marker genes (Albrecht and Bowman, 2008; Kim et al., 2009; Albrecht and Bowman, 2012; Rawat et al., 2015). Taken together, both the partial HLB-like symptom, albeit transient, and the expression pattern of HLB marker genes in the SDE15-transgenic citrus indicate that SDE15 is involved in the outcome of the Las-citrus interaction.

Example 6

Detection of SDE15 Inside Phloem Sap and Subcellular Localization of SDE15

To function as an effector, we expect that SDE15 would be secreted into the cytosol of phloem cells and may be detected in the phloem sap of Las-infected plants. We therefore developed a SDE15-specific antibody and examined whether SDE15 can be detected in the phloem sap by western blot. We could clearly detect SDE15 in the phloem sap extract of Las-infected barks but not in healthy citrus barks by western blot (FIG. 6C). To determine the subcellular locations of SDE15 in the plant cell, we performed subcellular localization of SDE15 by transient expression of SDE15-EYFP fusion protein in *N. benthamiana*. We found that SDE15 is localized to the cytoplasm and the nucleus (FIG. 6D).

We next analyzed the expression pattern of the SDE15 transcript in Las-infected citrus and psyllids using quantitative reverse transcription-PCR (qRT-PCR). SDE15 showed a higher expression level in citrus than in psyllids (FIG. 6E). Furthermore, SDE15 expression level was higher in the early stage (asymptomatic) than the later stage (symptomatic) of Las infection (FIG. 6F), indicating that SDE15 likely functions at a relatively early stage of Las infection before the appearance of visible HLB symptoms.

Example 7

SDE15 Suppresses PCD and Promotes Las Growth in Planta

Figure 7A:
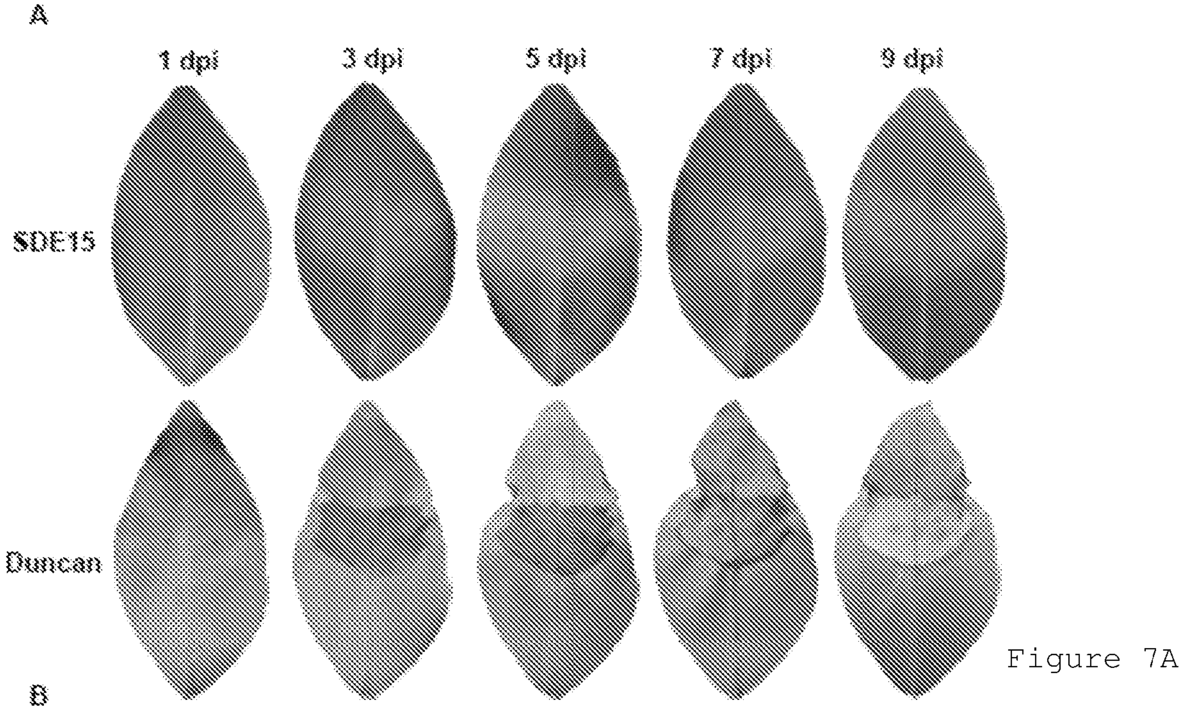
FIG. 7A A strong HR, a form of programmed cell death (PCD), was observed in wild type Duncan grapefruit at 3 days after inoculation with *Xanthomonas citri* subsp. *citri* strain $A^w$ ($XccA^W$). Only slight cell death was observed on the $XccA^W$-infiltrated leaves of SDE15-transgenic citrus at 5 days post inoculation. $XccA^W$ cells were infiltrated into citrus leaves at a concentration of $10^8$ CFU/ml.
Figure 7B:
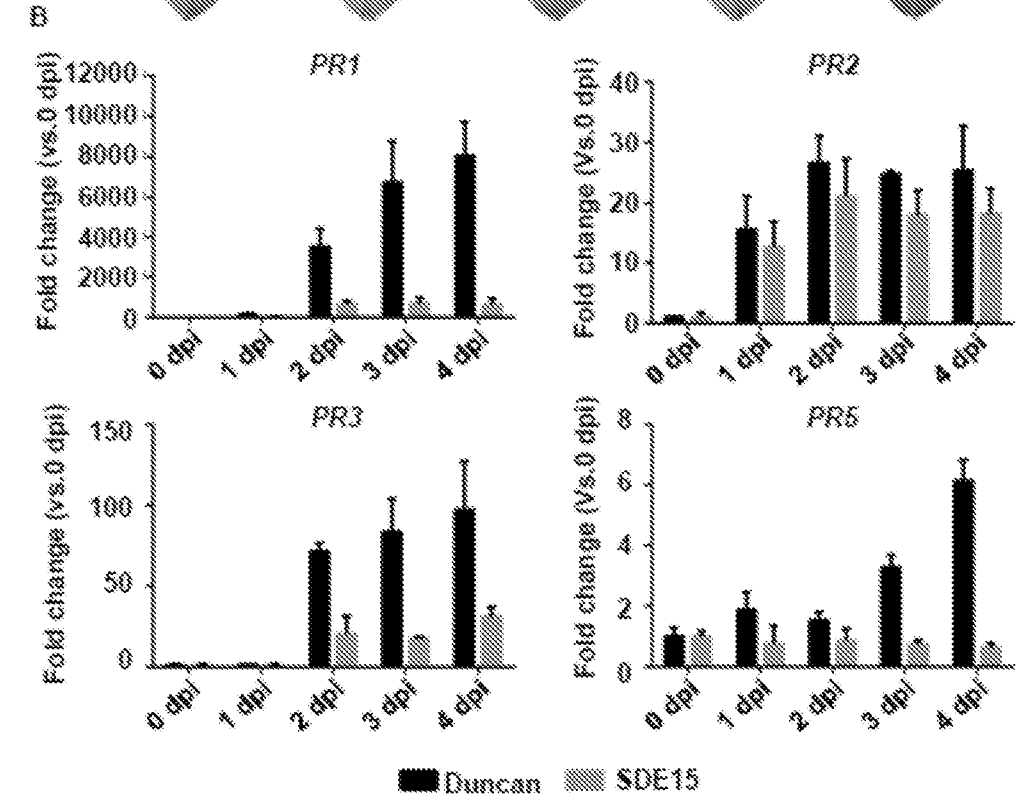
FIG. 7B. qRT-PCR analysis of PR genes. Expression of PR1, PR3 and PR5 was repressed in SDE15-transgenic citrus compared to that in wild type Duncan after HR induction by $XccA^W$. The house keeping gene encoding glyceraldehyde-3-phosphate dehydrogenase-C(GAPDH-C) was used as an endogenous control. Bars represent the mean of four replicates. Error bars indicate standard error of mean. All experiments were repeated three times with the similar results.

Many effectors of extracellular pathogens have been reported to suppress plant defenses (Jones. J. D., and Dangl, J. L. (2006). Nature 444, 323-329; Toruño, T. Y., Stergiopoulos, I., and Coaker, G. (2016). Annu Rev Phytopathol 54, 419-441). To investigate whether SDE15 (from a cytosolic bacterial pathogen) is involved in suppressing plant defenses, we inoculated SDE15-transgenic and nontransgenic Duncan grapefruit with *Xanthomonas citri* subsp. *citri* strain $A^w$ ($XccA^w$), which triggers the immunity-associated hypersensitive reaction (HR, a form of PCD) in Duncan grapefruit. Intriguingly, we found $XccA^w$ did not induce an HR in the leaves of SDE15-transgenic Duncan grapefruit, whereas an HR was observed in the nontransgenic Duncan grapefruit (FIG. 7A). We next examined immunity-associated gene expression in SDE15 transgenic and nontransgenic plants after inoculation with $XccA^w$. The expression of PR1, PR3, and PR5 genes was markedly reduced in the SDE15-transgenic than nontransgenic Duncan grapefruit (FIG. 7B). Taken together, these results suggest that SDE15 is a potent suppressor of PCD in citrus.

Figure 8:
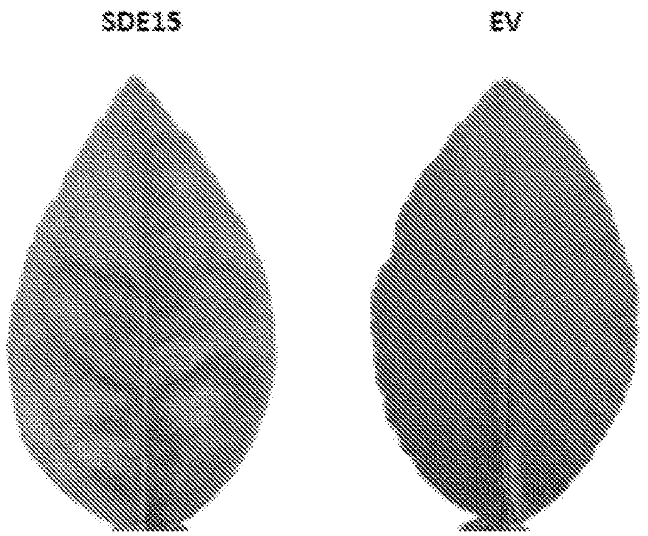
FIG. 8. Transgenic SDE15 citrus plants are more susceptible to HLB. Leaf images taken 3 months post HLB infection via budding grafting. The Las titer in SDE15-transgenic citrus and EV-transgenic control citrus were determined by TaqMan qPCR 0, 1, 2, and 3 months post HLB infection. Each Ct value was represented by Means±standard error ($n_{SDE15}$=7, $n_{EV}$=5). Asterisks represent significant differences in the Las titer between SDE15-transgenic citrus and non-transgenic control (**p-Value<0.01).

The ability of SDE15 to suppress PCD and defense gene expression prompted us to examine whether the SDE15 transgenic plants could promote Las growth. For this purpose, we graft-inoculated SDE15-transgenic and EV-transgenic Duncan grapefruit plants with Las. Significant increase of Las titers was observed over a four-month period in the SDE15-transgenic citrus compared to the EV-transgenic Duncan grapefruit plants, as estimated by qPCR assays (FIG. 8). In accordance, visible HLB symptoms were observed earlier on leaves of SDE15-transgenic citrus than control plants after Las graft-inoculation (FIG. 8).

Figure 9A:
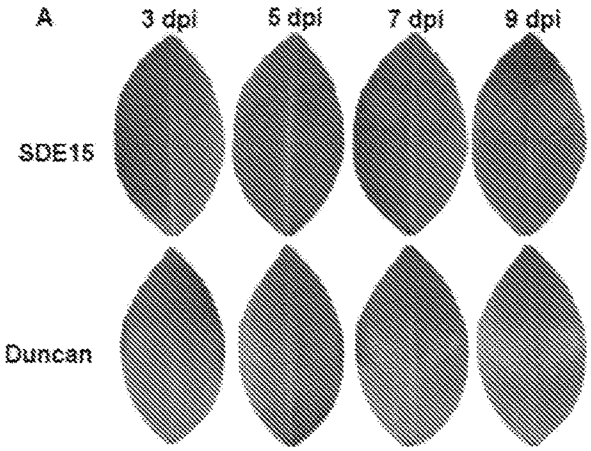
FIG. 9A. Water-soak symptom (grey color) was observed on SDE15-transgenic citrus at 5 days post XacA 306 inoculation.
Figure 9B:
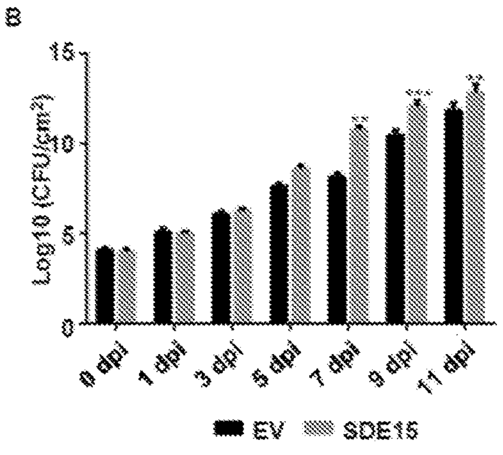
FIG. 9B. Bacterial population increase of XacA 306 in SDE15-transgenic citrus was faster than in non-transgenic Duncan grapefruit. Bacterial cells were infiltrated into citrus leaves at a concentration of $10^6$ CFU/ml. Error bars indicate standard error of mean (n=4). Asterisks represent significant differences in the bacteria population between SDE15-transgenic citrus and non-transgenic control (p-Value<0.01, *p-Value<0.001).

Because SDE15 suppressed PCD triggered by $XccA^w$, we also tested whether SDE15 transgenic plants become more susceptible to virulent Xcc strain XacA 306. Indeed, the canker symptom caused by XacA 306 appeared faster in SDE15 transgenic citrus compared to EV-transgenic plants. In addition, higher XacA 306 populations were detected in SDE15 transgenic grapefruit than that in the EV-transgenic Duncan grapefruit (FIG. 9). Thus, transgenic expression of SDE5 causes broad susceptibility to both HLB and citrus canker, two of the most important diseases in citrus.

Example 8

SDE15 Interacts with the PCD Repressing Protein CsACD2

Because SDE15 does not contain obvious sequence domains that suggest enzymatic activities, we hypothesized that SDE15 might exert its suppressive effect on PCD and defense gene expression via protein-protein interactions. To identify the targets of SDE15, we performed yeast two-hybrid (Y2H) screening with SDE15 without its signal peptide using cDNA libraries generated with mRNAs isolated from the Valencia sweet orange at different Las infection stages (healthy (H), asymptomatic (AS) and symptomatic (S)). We identified 20 SDE15-interacting proteins in the H library, 60 in the AS library and 6 in the S library (Table 1B).

Among the SDE15-interacting proteins identified by Y2H (Table 1B), CsACD2 (Accession No. Cs1g22670) (FIG. 10) was of special interest. It shares 55% similarity with the *Arabidopsis* ACD2 protein (Greenberg et al., 1994; Wüthrich et al., 2000). In *Arabidopsis*, ACD2 protects cells from PCD caused by endogenous porphyrin-related molecules including red chlorophyll catabolite (RCC) or exogenous protoporphyrin IX (Mach, J. M., Castillo, A. R., Hoogstraten, R., and Greenberg, J. T. (2001). T Proc Natl Acad Sci USA 98, 771-776; Yao, N., Eisfelder, B. J., Marvin, J., and Greenberg, J. T. (2004). Plant J 40, 596-610). We hypothesized that SDE15 may target CsACD2 to suppress PCD as a mechanism to promote Las growth in the phloem. We confirmed the SDE15-CsACD2 interaction via pair-wise Y2H assay (FIG. 10A). To further confirm the interaction between SDE15 and CsACD2, we conducted bimolecular fluorescence complementation (BiFC) assay in vivo and glutathione-S-transferase (GST) pull-down assay in vitro. Co-transformation of SDE15-EYFP$^N$ and EYFP$^C$-CsACD2 or EYFP$^C$-SDE15 and CsACD2-EYFP$^N$ into citrus leaf protoplasts displayed strong signals in the cytoplasm, but not in negative controls (FIG. 10B GST pull-down assay confirmed direct interaction between GST-SDE15 and MBP-CsACD2 fusion proteins (FIG. 10C). These results demonstrate a genuine interaction between SDE15 and CsACD2.

Example 9

C-Terminal is Essential for SDE15 to Interact with RCCR Domain of CsACD2

To further define the regions of SDE15 and CsACD2 involved in interaction, truncated proteins GST-SDE15$^{\Delta N}$ (SDE15 protein without the signal peptide and additional 25 aa at the N-terminus), GST-SDE15$^{\Delta C}$ (SDE15 protein without the signal peptide and additional 25 aa at the C-terminus) and MBP-RCCR (the RCCR domain of CsACD2 with deletion of 71 aa at the N-terminus) were expressed in *E. coli*, purified and used in GST pull-down assays (FIG. 10D, E). Results showed that the RCCR domain of CsACD2 was sufficient to interact with GST-SDE15 (FIG. 10D). In addition, deletion of the C-terminal, but not the N-terminal of SDE15 abolished its interaction with CsACD2 (FIG. 10E).

Figure 11:
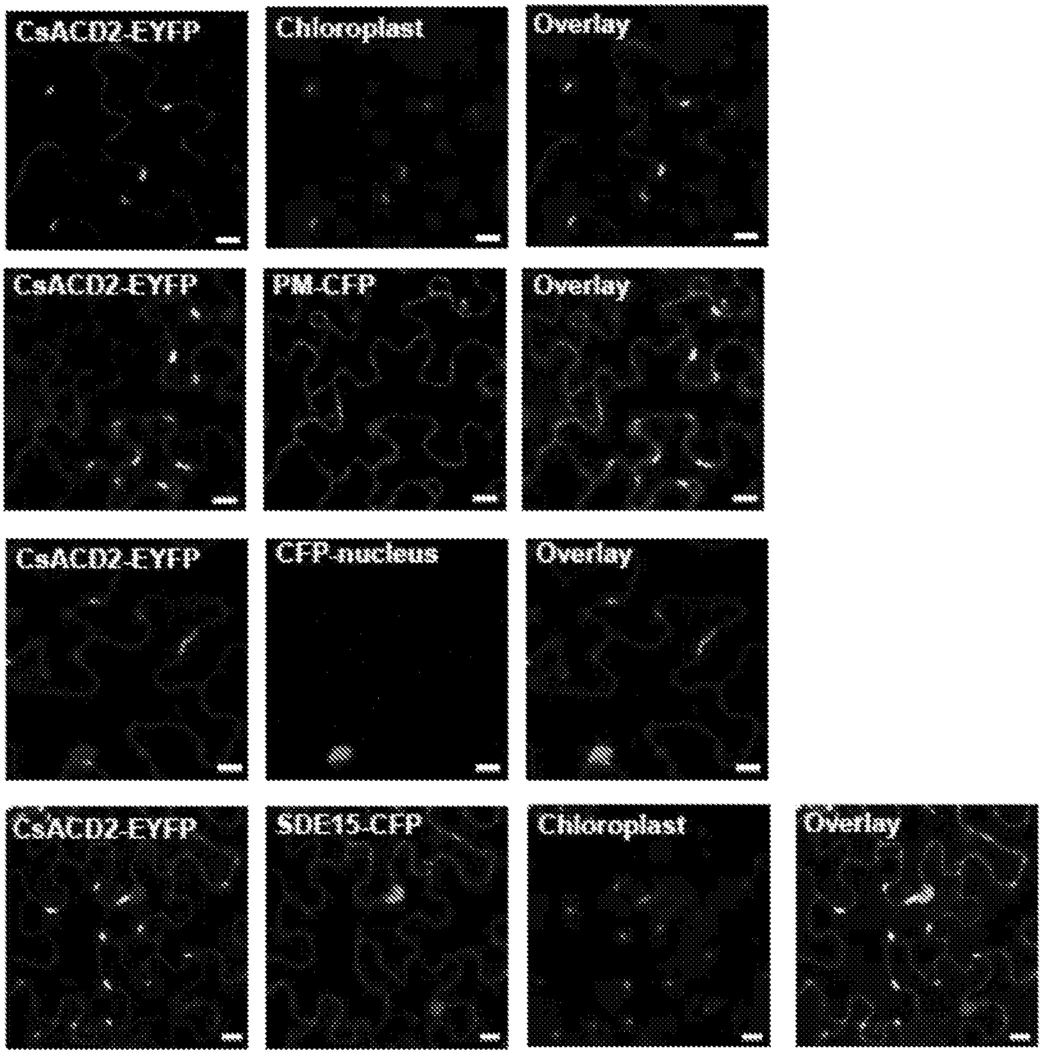
FIG. 11. Subcellular localization of CsACD2 and co-localization of SDE15 and CsACD2. CsACD2-EYFP was co-expressed with the plasma membrane localization-marker PM-CFP, the nucleus-marker CFP-nucleus or SDE15-CFP in leaves of *N. benthamiana. A. tumefaciens* strain GV2260 harboring the corresponding plasmids were infiltrated into leaves at $OD_{600}$ of 0.2. Subcellular localization was inspected and photographed 1 day post infiltration. Scale bars: 10 μm.

Next, we examined the subcellular localization of CsACD2 in *Nicotiana benthamiana* leaf cells. CsACD2 was mostly found in the chloroplast and partially in the cytosol and the nucleus (FIG. 11). Co-localization of SDE15-CFP and CsACD2-EYFP could be detected in the cytoplasm and the nucleus (FIG. 11).

Example 10

SDE15 Promotes the RCCR Activity of CsACD2

It has been shown that ACD2 in *Arabidopsis* represses PCD by functioning as a red chlorophyll catabolite reductase (RCCR) to catalyzing porphyrin-related molecules such as RCC Pruzinská, A., Tanner, G., Aubry, S., Anders, I., Moser, S., Müller, T., Ongania, K. H., Kräutler, B., Youn, J. Y., Liljegren, S. J., and Hörtensteiner, S. (2005). Plant Physiol 139, 52-63). To determine whether CsACD2 is involved in SDE15-mediated suppression of PCD, we infiltrated the leaves of *N. benthamiana* with *Agrobacterium* harboring the binary vector that expresses CsACD2-YFP fusion protein and/or SDE15, followed by infiltration with *Agrobacterium* containing a binary vector that expresses AvrBsT 2 days after CsACD2 infiltration (FIG. 12A, B). As expected, AvrBsT triggered an HR in the absence of SDE15 but that HR was repressed in the presence of SDE15. On the other hand, we found neither SDE15$^{\Delta N}$ nor SDE15$^{\Delta C}$ could repress HR induced by AvrBsT. Intriguingly, however, we found that transient overexpression of CsACD2-YFP protein alone was also sufficient to suppress AvrBsT-elicited HR in *N. benthamiana* (FIG. 12A, B), suggesting that (i) SDE15 could interact with the endogenous homolog of ACD2 in *N. benthamiana* (NbACD2 hereinafter) and (ii) it enhances the stability or activity of CsACD2. To test the first possibility, we performed GST pull-down assays. Indeed, SDE15 interacted strongly with NbACD2. As in the case of CsACD2, the NbACD2-YFP fusion protein alone, when transiently expressed, was sufficient to suppress HR induction by AvrBsT. To examine the second hypothesis, we directly performed RCCR activity assay. SDE15 significantly increased the RCCR activity of CsACD2 to catabolize RCC to primary fluorescent catabolite (pFCC), while SDE15$^{\Delta N}$ and SDE15$^{\Delta C}$ lost the ability to promote the RCCR activity of CsACD2 (FIG. 12C).

Example 11

SDE15 Promotes the Chlorophyll Break-Down in Planta

HLB is associated with tissue chlorosis and vein mottling, both are indicative of chlorophyll break down and previous studies have shown that the levels of chlorophyll a and b were significantly reduced in HLB-diseased citrus trees (Killiny, N., and Nehela. Y. (2017). Mol Plant Microbe Interact 30, 543-556). As ACD2 is critical for alleviating the accumulation of toxic intermediates in the chlorophyll breakdown pathway, we surmise that SDE15 promotes the RCCR activity during Las infection by lowering toxic intermediates that induce PCD. We quantified the concentration of pheophorbide a, which is upstream of RCC in the chlorophyll break-down pathway. The concentration of pheophorbide a was significantly lower in the leaves of SDE15 transgenic citrus than that of the EV transgenic citrus under HLB-free conditions. In addition, the levels of chlorophyll a and chlorophyll b were also lower in SDE15 transgenic citrus than those in the EV transgenic citrus. Furthermore, the concentrations of the three compounds were lower in the leaves of Las-infected citrus (both SDE15 and EV transgenic plants) than those in the healthy EV transgenic plants. Our results suggest that, by promoting the RCCR activity of CsACD2, SDE15 likely prevents accumulation of PCD-eliciting intermediates during the break-down of chlorophylls. This activity also likely contributes to the development of yellowing symptom associated with HLB and explained the yellowing symptoms observed in the SDE15 transgenic citrus (FIG. 6B).

Example 12

Methods For Examples 5-11

Vectors Construction

To generate the construct for plant transformation, Las genomic DNA was isolated from HLB diseased citrus leaf by CTAB method. The coding sequence of SDE15 (222 bp) without signal peptide was PCR-amplified using gene-specific primers (Table S2). A BamHI recognition sequence and a KpnI recognition site with two protecting nucleotides were added to the 5' end of primers. The PCR product was purified and cloned into pGEM-T Easy vector (Promega, Madison, Wis., USA) and then cloned into the binary vector erGFP-1380N at the BamHI and KpnI sites to generate SDE15-overexpression vector. The resulting binary vector was transferred into *Agrobacterium tumefaciens* strain EHA105 and LBA4404 for citrus and tobacco transformation. Empty Vector (EV) without SDE15 fragment was used for citrus and tobacco transformation as negative controls.

For Y2H, the coding region of SDE15 (minus the putative signal peptide) was amplified and cloned in-frame with the GAL4 DNA-binding domain (BD) of the bait vector pGBKT7 to generate BD-SDE15 for Y2H library screening and co-transformation in yeast. The 996 bp coding sequence of CsACD2 was PCR-amplified from citrus leaf cDNA and cloned in-frame with the GAL4 DNA-activating domain (AD) of the prey vector pGADT7 to generate AD-CsACD2 for co-transformation with bait vector in yeast to confirm the interaction. BD and AD vectors were constructed by using the In-Fusion cloning kit (Clontech, Mountain View, Calif., USA).

Transient expression in citrus protoplast were used for subcellular localization and BiFC assays. For the subcellular localization assay, the coding region of SDE15 without signal peptide was inserted into EcoRI-digested C-terminal EYFP containing vector pSAT6-EYFP-N1 by using In-Fusion cloning kit to generate SDE15-EYFP fusion proteins. For the BiFC assay, SDE15 and CsACD2 were inserted into SalI-digested BiFC vectors pSAT6-nEYFP-C1 and pSAT6-cEYFP-C1-B by using In-Fusion cloning kit to produce SDE15-EYFP$^N$, EYFP$^C$-SDE15, CsACD2-EYFP$^N$ and EYFP$^C$-CsACD2 fusion proteins. All the vectors were subsequently used for citrus protoplast transformation.

To generate recombinant protein constructs for GST pull-down assay and red chlorophyll catabolite reductase (RCCR) assay, the coding region of SDE15 (without signal peptide) was inserted between EcoRI and XhoI sites of pGEX-4T-1 vector (GE Healthcare, Chicago, Ill., USA) to generate GST-SDE15 fusion protein vector as bait. The coding sequence of CsACD2 was inserted between BamHI and EcoRI sites of pMAL™-c5X vector (NEB, Ipswich, Mass., USA) to generate MBP-CsACD2 fusion protein vector as prey and source of RCCR for enzyme assay. The truncated sequences of SDE15 fragments (SDE15$^{\Delta N}$ and SDE15$^{\Delta C}$) were inserted into EcoRI-digested pGEX-4T-1 vector by using In-Fusion cloning kit to generate GST-SDE15$^{\Delta N}$ and GST-SDE15$^{\Delta C}$ fusion protein vectors as bait. The coding sequence of RCCR domain of CsACD2 was amplified and inserted between BamH I and EcoRI sites of pMAL™-c5X vector by using In-Fusion cloning kit to generate MBP-RCCR fusion protein vector as prey.

To generate the constructs for agro-infiltration assay in *N. benthamiana*, modified pCambia1380 vectors were constructed by inserting cauliflower mosaic virus promoter (CaMV 35S) and EYFP/CFP coding sequence to create the transient expression vectors with C-terminal EYFP reporter protein (pCambia1380-35S-EYFP) or C-terminal CFP reporter protein (pCambia1380-35S-CFP). The coding sequence of SDE15 without signal peptide was PCR-amplified and inserted between BamH I and Kpn I sites of pCambia1380-35S-EYFP and pCambia1380-35S-CFP to generate 35S-SDE15-EYFP and 35S-SDE15-CFP individually. The truncated sequences of SDE15 fragments (SDE15$^{\Delta N}$ and SDE15$^{\Delta C}$) were inserted between BamH I and Kpn I sites of pCambia1380-35S-EYFP by using In-Fusion cloning kit to generate 35S-SDE15$^{\Delta N}$-EYFP and 35S-SDE15$^{\Delta C}$-EYFP. The coding sequence of CsACD2 was inserted between BamH I and Kpn I sites of pCambia1380-35S-EYFP to generate 35S-CsACD2-EYFP vector. The coding sequence of NbACD2 was inserted between BamH I and Kpn I sites of pCambia1380-35S-EYFP by using In-Fusion cloning kit to generate 35S-BenACD2-EYFP vector. All the vectors were then transferred into *Agrobacterium tumefaciens* strain GV2260 for agro-infiltration assay.

All the primers used for vector construction were listed in Table S2.

TABLE S2 primers used for vector construction

| | Forward (5'-3') | Reverse (5'-3') |
|---|---|---|
| SDE15-OE | GGGGATCCATGGATACTCTCTCTGACTC | GGGGTACCTCTTTCCCATTCTCTAAC |
| BD-SDE15 C | ATGGAGGCCGAATTCATGGATACTCTCTCTGACTC | GGATCCCCGGGAATTCTCTTTCCCATTCTCTAAC |
| AD-CsACD2 | GGAGGCCAGTGAATTCATGGCTGTGAACCACTTATG | CACCCGGGTGGAATTCGGCAGTAAAAACCTTCTGTA |
| SDE15-BiFC | GAATTCTGCAGTCGACATGGATACTCTCTCTGACTC | CCGCGGTACCGTCGACTCTTTCCCATTCTCTAAC |
| CsACD2-BiFc | GAATTCTGCAGTCGACATGGCTGTGAACCACTTATG | CCGCGGTACCGTCGACGGCAGTAAAAACCTTCTGTA |
| GST-SDE15 | GGGAATTCATGGATACTCTCTCTGACTC | GGCTCGAGTCTTTCCCATTCTCTAAC |
| GST-SDE15$_{\Delta N}$ | TGGATCCCCGGAATTCATGGACGACTCCCATAATCAA | GTCGACCCGGGAATTCTCTTTCCCATTCTCTAAC |
| GST-SDE15$_{\Delta C}$ | TGGATCCCCGGAATTCATGGATACTCTCTCTGACTC | GTCGACCCGGGAATTCTATATTGTTCTTTATCTTTAT |
| MBP-CsACD2 | TATCGTCGACGGATCCATGGCTGTGAACCACTTATG | TACCTGCAGGGAATTCGGCAGTAAAAACCTTCTGTA |
| MBP-RCCR | TATCGTCGACGGATCCATGCCTGTTAGGCAGCTGAT | TACCTGCAGGGAATTCGGCAGTAAAAACCTTCTGTA |
| MBP-NbACD2 | TATCGTCGACGGATCCATGGCTATTTCAATATCCT | TACCTGCAGGGAATTCAGCATTGTAGATTTCCC |
| SDE15-YFP | TTGGATCCATGGATACTCTCTCTGACTC | GGGGTACCTCTTTCCCATTCTCTAAC |
| SDE15-CFP | TTGGATCCATGGATACTCTCTCTGACTC | GGGGTACCTCTTTCCCATTCTCTAAC |
| SDE15$_{\Delta N}$-EYFP | GGACTCTAGAGGATCCATGGACGACTCCCATAATCAA | CCCTTGCTCACCATGGTACCTCTTTCCCATTCTCTAAC |
| SDE15$_{\Delta C}$-EYFP | GGACTCTAGAGGATCCATGGATACTCTCTCTGACTC | CCCTTGCTCACCATGGTACCTATATTGTTCTTTATCTTTAT |
| CsACD2-YFP | TTGGATCCATGGCTGTGAACCACTTATG | GGGGTACCGGCAGTAAAAACCTTCTGTA |
| NbACD2-YFP | GGACTCTAGAGGATCCATGGCTATTTCAATATCCT | CCCTTGCTCACCATGGTACCAGCATTGTAGATTTCCC |

*Nucleotides underline is the restriction enzyme cutting site

Transient Gene Expression in Citrus Protoplasts

Protoplasts were isolated from etiolated Duncan grapefruit epicotyl segments by following the protocol of transient gene expression in *Arabidopsis* mesophyll protoplasts with modifications (Yoo, S. D., Cho, Y. H., and Sheen, J. (2007). Nat Protoc 2, 1565-1572). Briefly, epicotyl segments of Duncan grapefruit cultured in dark were cut to small pieces and digested in Cellulose "Onozuka" R-10 and MACEROZYME R-10 (Yakult Pharmaceutical, Japan) enzyme solution overnight. Protoplasts were harvested and used for plasmid transformation. Plasmids were transformed into citrus protoplasts by the polyethylene glycol 4000 (PEG4000)-mediated transformation method (Citovsky, V., Lee, L. Y., Vyas, S., Glick, E., Chen, M. H., Vainstein, A., Gafni, Y., Gelvin, S. B., and Tzfira, T. (2006). J Mol Biol 362, 1120-1131; Lee, L. Y., Fang, M. J., Kuang, L. Y., and Gelvin, S. B. (2008). Plant Methods 4, 24). For the BiFC assay, the coding sequence of SDE15 without signal peptide and full-length CsACD2 were cloned into either N-terminal or C-terminal fragments of EYFP vectors pSAT6-nEYFP-C1 and pSAT6-cEYFP-C1-B (Citovsky et al., 2006). The combinations of SDE15-$EYFP^N$/$EYFP^C$-CsACD2 and CsACD2-$EYFP^N$/$EYFP^C$-SDE15 were transiently co-transformed into protoplasts. Other combinations, such as SDE15-$EYFP^N$/$EYFP^C$, $EYFP^N$/$EYFP^C$-SDE15, SDE15-$EYFP^N$/$EYFP^C$-SDE15, CsACD2-$EYFP^N$-/$EYFP^C$, $EYFP^N$/$EYFP^C$-CsACD2, CsACD2-$EYFP^N$/$EYFP^C$-CsACD2, $EYFP^N$/$EYFP^C$ were also transformed into citrus protoplasts as controls. After incubation in dark overnight, the EYFP signals were examined and photographed under a fluorescence microscope for BiFC assay with excitation wavelength 514 nm (Olympus, Tokyo, Japan).

Plant Transformation and Pathogen Inoculation

*Agrobacterium* mediated transformation of etiolated epicotyl segments of Duncan grapefruit were carried out as described previously (Orbović, V., and Grosser, J. W. (2015). Methods Mol Biol 1224, 245-257). *Agrobacterium tumefaciens* EHA105 harboring the recombinant plasmid was used for citrus transformation. Transgenic lines showing kanamycin-resistance and erGFP-specific fluorescence were selected and then micro-grafted in vitro onto 1-month old Carrizo citrange nucellar rootstock seedlings. After a month of growth in vitro, the grafted shoots were potted into a peat based commercial potting medium and acclimated under greenhouse conditions.

*N. tabacum* cv. Petite Havana SR1 seeds were sown on MS medium (Sigma-Aldrich, St. Louis, Mo., USA) containing 3% sucrose and 0.8% agar and allowed to germinate at 22±1° C. (16 h light and 8 h darkness). Subsequently, plants were grown and maintained in MS medium. Fresh tobacco leaf discs were infected with *A. tumefaciens* strain LBA4404 harboring the recombinant plasmid. The regenerated shoots were maintained on MS medium supplemented with 0.2 mg $L^{-1}$ NAA and 3 mg $L^{-1}$ 6-BA along with 100 mg $L^{-1}$ kanamycin and 500 mg $L^{-1}$ cephotaxime. Kanamycin-resistant, erGFP and PCR positive shoots of T0 transgenic plants were selected, transferred to the greenhouse and maintained up to T2 generations, which were used for phenotype inspection and further analysis.

For the HLB pathogenicity assay, the SDE15-transgenic and EV-transgenic trees was inoculated with Las via grafting as previously reported (Li, J., Pang, Z., Trivedi, P., Zhou, X., Ying, X., Jia, H., and Wang, N. (2017). Mol Plant Microbe Interact 30, 620-630). Midrib DNA was isolated from the grafted trees monthly after grafting up to 4-month post grafting and used to quantify Las by Taqman qPCR with Primer/probe combination (CQULA04F-CQULAP10-CQULA04R) as described previously (Wang, Z., Yin, Y., Hu, H., Yuan, Q., Peng, G., and Xia, Y. (2006). Plant Pathology 55, 630-638). The Ct value of each amplicon represents the Las genomic copy numbers in 100 ng citrus midrib DNA. The test was repeated three times.

For the *Xanthomonas citri* subsp. *citri* (Xcc) pathogenicity and hypersensitive reaction (HR) assays in citrus, SDE15-transgenic and non-transgenic Duncan grapefruit plants were used for inoculation in a quarantine greenhouse. The wild-type strain Xac306 causes disease on grapefruit whereas the Xcc $A^w$ strain triggers hypersensitive reaction in grapefruit leaves[7]. Xcc strains were grown with shaking overnight at 28° C. in NB, centrifuged down, and suspended in sterile tap water, and the concentrations were adjusted to $10^6$ CFU/ml (for Xac306) and $10^8$ CFU/ml (for Xcc $A^w$) individually. Bacterial solution was infiltrated into fully expanded, immature leaves with needleless syringes (Yan, Q., and Wang, N. (2012). Mol Plant Microbe Interact 25, 69-84). The tests were repeated three times with similar results. Disease symptoms and HR phenotype were photographed at 3, 5, 7, 9 and 11 days post inoculation. Growth curve assay of Xac 306 was conducted at 0, 1, 3, 5, 7, 9 and 11 days post inoculation.

Agro-Infiltration Assay in *N. benthamiana*

*A. tumefaciens* strain GV2260 cells containing binary vectors were cultured overnight in LB medium with 50 μg $ml^{-1}$ of rifampicin and 50 μg $ml^{-1}$ kanamycin and re-suspended in induction medium (10 mM MgCl2, 10 mM MES pH 5.6, 200 uM acetosyringone), and incubated at 25° C. with shaking for 4 h. The cultures were diluted to OD600 of 0.1 or 0.2. For each vector, three leaves of young *N. benthamiana* plants were infiltrated with diluted *A. tumefaciens* suspension as triplicates.

For the HR assay, young leaves of *N. benthamiana* were first infiltrated with *A. tumefaciens* cells containing binary vectors for SDE15-EYFP and/or CsACD2-EYFP by using a needleless syringe, kept in a greenhouse for 2 days and then infiltrated with another *A. tumefaciens* strain harboring the binary vector carrying the AvrBsT protein which can trigger HR as reported previously Kim, N. H., Choi, H. W., and Hwang, B. K. (2010). Mol Plant Microbe Interact 23, 1069-1082). Agro-infiltrated plants were kept in a greenhouse and HR were examined and photographed at 3 days post AvrBsT inoculation. For the electrolyte leakage assay, leaf discs of AvrBsT infiltrated plants at 2 days post infiltration were floated on deionized water with shaking. The conductivity of the solution was measured 4 h later using an Oakton™ Conductivity Benchtop Meters (Thermo Fisher, Waltham, Mass., USA). The *A. tumefaciens* transformant cells harboring an empty vector were infiltrated into the leaves of *N. benthainiana* as controls.

For the localization and co-localization assay, CsACD2-EYFP was co-expressed with the plasma membrane localization-marker PM-CFP, the nucleus-marker CFP-nucleus or SDE15-CFP in leaves of *N. benthamiana. A. tumefaciens* strain GV2260 harboring the corresponding plasmids were infiltrated into leaves at OD600 of 0.2. Subcellular localization was inspected and photographed 1 day post infiltration.

Extraction of Phloem Sap Proteins

An optimized method of protein extraction from phloem sap was performed by combining two methods reported before (Hijaz, F., and Killiny, N. (2014). Collection and chemical composition of phloem sap from *Citrus sinensis* L. Osbeck (sweet orange). PLoS One 9, e101830; O'Leary, B. M., Rico, A., McCraw, S., Fones, H. N., and Preston, G. M. (2014). J Vis Exp.). Briefly, 10-20 cm (0.5 cm diameter)

stems from Las infected and uninfected trees were collected. The bark area was stripped into two pieces and was manually removed from the twig. The inner part of the bark was rinsed with deionized water and dried with Kim wipes. Then the bark strips were cut into about 1-cm pieces using a sterile razor blade and placed in a 60-mL syringe filled with distilled water. Vacuum was applied for 5-15 seconds repeatedly to let water penetrated barks. Then the barks were dried with Kim wipes and placed in a 20-mL syringe, centrifuged in 50 mL falcon tube for 10 min at 4,000 g, at 4° C. The collected phloem sap was centrifuged at 15,000 g for 5 min. The supernatant was heating for 5 min at 95° C. in SDS gel-loading buffer for SDE15 detection with specific antibody.

RNA Isolation and Expression Analysis of HLB Associated Genes qRT-PCR was performed to detect the expression of SDE15 in SDE15-transgenic plants (both in citrus and tobacco) and in non-transgenic citrus plants and psyllids. We also examined the expression of HLB marker genes in the SDE15-transgenic citrus and PR genes in SDE15-transgenic plants after HR induction. Total RNA of transgenic citrus, transgenic tobacco and psyllids were extracted by Trizol reagent (Thermo Fisher) and digested with DNase I (Promega) followed by the manufacturers' instructions. First-strand cDNA was synthesized from purified RNA with ImProm-II™ Reverse Transcription System (Promega) and diluted 10 times for RT-qPCR to detect related genes with specific primers (Table S3). 20 μl of qPCR reaction consisted of 10 μl of 2×KiCqStart® SYBR® Green qPCR ReadyMix™ (Sigma-Aldrich), 1 μl of each primer (5 μM), 2 μl of diluted cDNA template, and 6 μl of DNase/RNase free water. The PCR cycling consisted an initial activation step at 95° C. for 3 min, followed by 40 cycles of 95° C. for 15 s and 60° C. for 40 s. All cDNA samples were run in triplicates. Citrus GAPDH gene, tobacco Actin gene and Las gyrA gene were used as endogenous controls wherever appropriate.

The qPCR primer sequences of specific genes and endogenous control genes are listed in Table S3.

TABLE S3 primers used for qRT-PCR and Taqman probe PCR analysis

| | Forward (5'-3') | Reverse (5'-3') |
|---|---|---|
| qSDE15 | ACTCCCATAATCAAAAGCCTACG | CGTATCTTTCACCATTCCATCCTC |
| qCsACD2 | GGCTAAATCAGTGTGCTTGTG | ATCAACCCATCCCTCTTTTCC |
| PR1 | AAATGTGGGTGAATGAGAAAGC | ATTATTGTTGCACGTCACCTTG |
| PR2 | TTCCACTGCCATCGAAACTG | GTAATCTTGTTTAAATGAGCCTCTTG |
| PR3 | GGCTCAAACTTCACATGAAACTAC | GTTGACAATAATCTCCAGGGTTTC |
| PR5 C | ACCATTGCCAATAACCCTAATG | GGGACAGTTACCGTTAAGATCAG |
| PP2-B15 | TCGTTGCCATCAGAAGTATCAC | CCAACGCAAATAAACTGTCCC |
| WRKY40 | CTCCTGTTCCAAATGCCAAG | CCGAGGTGAGGGATTATCTTTAG |
| ZIP5 | TGAATATGCTGGTGAATCGGAG | GCTGCAACCAAAGGCTTAATAG |
| Sweet7 | GCTAACCCTACTTCACTCCAC | GGCATATACTCCACGCTCTTG |
| Sweet15 | GTGTTGCCGTTTCTGTTAGTG | GCGAACCACATAATTGCACTC |
| Chalcone synthase | GCGTTCTAGTCGTATGCTCTG | GCCAATGATTAAAGCTGCGG |
| CsGAPDH | GGAAGGTCAAGATCGGAATCAA | GGAAGGTCAAGATCGGAATCAA |
| NbActin | CCTGAGGTCCTTTTCCAACCA | GGATTCCGGCAGCTTCCATT |
| gryA | CAATGTGCTGGTCAATGGTG | AATCTCCATCAAGGCATCCAG |
| CQULA04 (β operon primer) | TGGAGGTGTAAAAGTTGCCAAA | CCAACGAAAAGATCAGATATTCCTCTA |
| CQULAP10 (β operon probe, 5'-3') | FAM ATCGTCTCGTCAAGATTGCTATCCGTGATACTAG-TAMRA | |

Yeast Two-Hybrid Library Screening and Interaction Analysis

Total RNA was extracted from leaves of Valencia sweet orange (HLB symptomatic (S, Las Ct value 25~26 per 100 ng DNA), HLB asymptomatic (AS, Las Ct value 28~30 per 100 ng DNA) and healthy (H, Las free)) by Trizol reagent (Thermo Fisher), digested by DNase I (Promega). mRNA samples were purified using the NucleoSpin® RNA kit (Clontech). ALL three types of mRNA samples were used to construct yeast two-hybrid libraries in the pGADT7-Rec vector using the Make Your Own "mate and plate" library system (Clontech) following the manufacturer's instructions and transformed in the yeast strain Y187 by using Yeastmaker™ Yeast Transformation System 2 (Clontech). The titer of each constructed library is more than $3\times10^8$ which represents the good transformation efficiency. BD:SDE15 construct was transformed into Y2HGOLD yeast strain (Clontech) Library screening was performed according to the Matchmaker Gold yeast two-hybrid system protocol (Clontech). Standard positive controls (pGBKT7-53 and pGADT7-T; Clontech) and standard negative control (pGBKT7-Lam and pGADT7-T) were included. After mating between the Gold strain transformed with BD:SDE15 and the Y187 libraries, diploid yeasts were plated on synthetic dropout (SD)/-Leu/-Trp (DDO), SD/-Leu/-Trp/-Ade/-His (QDO) and SD/-Leu/-Trp/-Ade/-His plus X-α-gal and Aureobasidin A (AbA) (QDO/A/X) agar plates to detect the activation of reporter genes HIS3, ADE2, MEL1 (for α-galactosidase activity) and $AbA^r$ (for Aureobasidin A resistance). The fragments of positive diploid yeast were amplified by colony PCR with Matchmaker® Insert Check PCR Mix 2 (Clontech) and analyzed by electrophoresis on a 0.8% TAE Agarose/EtBr gel. The PCR products with single band were purified and sent for sequencing. The PCR products with multiple bands indicate the presence of more than one prey plasmid in a heterozygote cell. For this situation, plasmids were isolated from the heterozygote cells with multiple plasmids with Easy Yeast Plasmid Isolation Kit (Clontech) and transferred into *E. coli* for sequencing. BLAST was used to compare the inserts nucleotide sequences to the genome of sweet orange to identify corresponding proteins which interact with SDE15.

Recombinant Proteins Expression and GST Pull-Down Assay

*E. coli* cells expressing GST or GST fusion proteins were washed in PBS buffer and suspended with CelLytic B Cell Lysis Reagent (Sigma-Aldrich) to generate the cell lysates. After centrifugation, the cell lysates were incubated with glutathione agarose beads in accordance with the GST Protein Interaction Pull-Down Kit instructions (Thermo Scientific). The beads were washed to remove the unbound proteins and incubated with *E. coli* cell lysates expressing either MBP or MBP fusion protein for 1 to 2 h at 4° C. After washing four times, the beads were eluted with 10 mM glutathione, and the eluates were collected and immunoblotted using anti-MBP (NEB) and anti-GST (Abcam, Cambridge, UK) antibodies.

Enzyme Assays

Coupled Pheophorbide a oxygenase (PaO)/RCCR assay was performed to test CsACD2 activity according to published procedures (Hortensteiner, S., Vicentini, F., and Matile, P. (1995). Chlorophyll breakdown in senescent cotyledons of rape, *Brassica napus* L.: Enzymatic cleavage of phaeophorbide a in vitro. New Phytol. 129, 237-246; Wüthrich, K. L., Bovet, L., Hunziker, P. E., Donnison, I. S., and Hortensteiner, S. (2000). Plant J 21, 189-198; Pruzinská et al., 2005). Thylakoids containing PaO were isolated and solubilized from senescent citrus leaves as described previously (Hortensteiner et al., 1995). PaO was partially purified from solubilized membranes and used for enzyme assay (Rodoni, S., Vicentini, F., Schellenberg, M., Matile, P., and Hortensteiner, S. (1997). Plant Physiol 115, 677-682). MBP-CsACD2 fused protein was expressed and purified with the pMAL protein fusion & purification system (NEB) as the source of RCCR. Briefly, assays (total volume of 50 μl) contained different combinations of PaO (equivalent to 0.5 g of tissue), *E. coli* (50 μl) protein extracts as a source of RCC-forming factor (RFF), and purified MBP-CsACD2 (1.5 μg) as the source of RCCR. The assays were supplemented with 0.5 mM pheide a, 10 μg ferredoxin (Fd), and a Fd-reducing system consisting of 2 mM Glc-6-P, 1 mM NADPH, 50 milliunits of Glc-6-P dehydrogenase, and 5 milliunits of Fd-$NADP^+$ oxidoreductase. After 1 hour incubation at 25° C., reactions were terminated by the addition of 80 mL methanol. Formation of primary fluorescent chlorophyll catabolite (pFCC) was followed by reversed-phase HPLC with 36% (v/v) 50 mM potassium phosphate buffer, pH 7.0, in methanol as solvent. Activities are determined as integrated fluorescence units (320/450 nm) of pFCCs.

Quantification of Compounds Participating Chlorophyll Break-Down Pathway

Three compounds (chlorophylls a, b and pheophorbide a) in Chlorophyll break-down pathway were extracted and quantified as previously descripted (Garrido, J. L., Rodríguez, F., Campaña, E., and Zapata, M. (2003). J Chromatogr A 994, 85-92), with modification. Briefly, leaf samples of SDE15 transgenic citrus, EV transgenic citrus, SDE15 transgenic citrus infected with HLB and EV transgenic citrus infected with HLB were collected and homogenized with 8 ml of 90% acetone and left for 16 hours at −10° C. All extracts were filtered through 25 mm, 0.2 μm GHP Acrodisc filters (Sigma-Aldrich) prior to injection. All sample preparations were done under subdued light. The standards of chlorophylls a, b and pheophorbide a were obtained from Sigma-Aldrich. All the standards and samples were followed by reversed-phase HPLC. Mobile phase consisted of (A) methanol, (B) 0.025M ammonium acetate and (C) acetone. A linear gradient from A-B (80:20, v/v) to A-C (80:20, v/v) was pumped during 15 min, followed by an isocratic hold at A-C (80:20, v/v) during a further 5 min. The flow-rate was 1 ml/min.

What is claimed is:

1. A plant comprising plant cells comprising a modification to an endogenous gene, wherein the polypeptide encoded by the endogenous gene interacts with a Sec-dependent effector (SDE) secreted by a bacterial species from the genus *Ca. Liberibacter*, wherein the modification interrupts interaction of the polypeptide with an SDE and confers resistance or tolerance to *Ca. Liberibacter* infection in the plant relative to a plant of the same variety lacking the modification, wherein the SDE is SDE15, and wherein the endogenous gene is accelerated cell death 2 (ACD2) comprising a red chlorophyll catabolite reductase (RCCR) domain and the modification comprises;

insertion of an indel that disrupts expression of the RCCR domain, a deletion of at least 1 nucleotide of RCCR domain, and/or a substitution of at least 1 nucleotide of the RCCR domain resulting in an amino acid substitution relative to that found in nature.

2. The plant of claim 1, wherein the plant is citrus.

3. The plant of claim 1, wherein the modification is made to at least one of SEQ ID NO: 7-9, or a sequence comprising at least 95% identity therewith.

4. The plant of claim 1, wherein the plant is a solanaceous plant.

5. The plant of claim 4, wherein the plant is *Solanum tuberosum*.

6. The plant of claim 1, wherein said modification comprises a deletion, a substitution, or an insertion.

7. The plant of claim 1, wherein the plant is a grapefruit tree, an orange tree, a sweet orange tree, a lime tree, citrumelo tree, trifoliate tree, reticulata tree, aurantiuma tree, lemon tree, a papeda tree, a pummelo tree or a mandarin orange tree.

8. A seed that produces the plant of claim 1.

9. A plant part of the plant of claim 1, wherein the plant part comprises the modification.

10. A method of generating a modified citrus plant comprising resistance or tolerance to infection by a bacterial species from the genus *Ca. Liberibacter*; the method comprising the steps of:

(a) modifying an RCCR domain of an ACD2 gene of a citrus plant cell such that interaction of the polypeptide encoded by said ACD2 gene with a Sec-dependent effector (SDE) secreted by a bacteria species from the genus *Ca. Liberibacter* is reduced, wherein the SDE comprises Las4025; and (b) regenerating the modified plant from said plant cell or a progenitor cell thereof, wherein said the plant comprises said modification.

11. The method of claim 10, wherein the plant is citrus.

12. The method of claim 10, wherein a modification to the RCCR domain minimizes inhibition of a hypersensitive response by the SDE in the plant relative to a plant of the same variety lacking the modification to the RCCR domain.

13. A plant comprising resistance to *Ca. Liberibacter* infection produced by the method of claim 10.

* * * * *